US005457195A

United States Patent [19]
Sessler et al.

[11] Patent Number: 5,457,195
[45] Date of Patent: Oct. 10, 1995

[54] SAPPHYRIN DERIVATIVES AND CONJUGATES

[75] Inventors: Jonathan L. Sessler; Brent L. Iverson; Vladimir Král; Kevin Shreder, all of Austin, Tex.; Hiroyuki Furuta, Mitsuyoshi, Japan

[73] Assignee: Board of Regents, The University of Texas System, Austin, Tex.

[21] Appl. No.: 964,607

[22] Filed: Oct. 21, 1992

Related U.S. Application Data

[63] Continuation-in-part of Ser. No. 454,298, Dec. 21, 1989, Pat. No. 5,159,065.
[51] Int. Cl.$^6$ ............................................. C07D 487/22
[52] U.S. Cl. ...................................... 540/472; 540/145
[58] Field of Search ................................. 540/472, 474, 540/465; 536/28.1, 28.2

[56] References Cited

U.S. PATENT DOCUMENTS

| | | | |
|---|---|---|---|
| 4,833,790 | 11/1989 | Levy et al. | 540/145 |
| 4,935,498 | 6/1990 | Sessler et al. | 534/15 |
| 5,041,078 | 8/1991 | Matthews et al. | 604/4 |
| 5,162,509 | 11/1992 | Sessler et al. | 540/465 |
| 5,252,720 | 10/1993 | Sessler et al. | 540/465 |

FOREIGN PATENT DOCUMENTS

| | | |
|---|---|---|
| 0196515 | 3/1986 | European Pat. Off. . |
| 0233701 | 1/1987 | European Pat. Off. . |
| WO90/10633 | 9/1990 | European Pat. Off. . |

OTHER PUBLICATIONS

International Search Report, mailed Feb. 3, 1994.
Aoyama, et al., "Multi-Point Interaction of Phosphates with Protonated Pyridylporphyrin. Discrimination of Monoalkyl and Dialkyl Phosphates," *Chemistry Letters*, 1991, 1241–1244.
Bauer et al., "Sapphyrins: Novel Aromatic Pentapyrrolic Macrocycles," *J. Am. Che. Soc.*, 1983, 105:6429–6436.
Broadhurst and Grigg, "18– and 22–π–Electron Macrocycles Containing Furan, Pyrrole, and Thiophen," *Chemical Communications*, 1969, 1480–1482.
Broadhurst and Grigg, "The Synthesis of 22 π–Electron Macrocycles. Sapphyrins and Related Compounds," *J.C.S. Perkin*, 2111–2116, 1972.
Claude et al., "Binding of Nucleosides, Nucleotides and Anionic Planar Substrates by Bis–Intercaland Receptor Molecules," *J. Chem. Soc, Chem. Commun.*, 1991, 17:1182–1185.
Cramer et al., "Synthesis and Structure of the Chloride and Nitrate Inclusion Complexes of [16–Pyrimidinium crown–4]," *J. Am. Chem. Soc.*, 1991, 113:7033–7034.
Cuellar and Marks, "Synthesis and Characterization of Metallo and Metal–Free Octaalkylphthalocyanines and Uranyl Decaalkylsuperphthalocyanines," *Inorg. Chem.*, 1981, 20:3766–3770.
Dietrich et al., "Proton Coupled Membrane Transport of Anions Mediated by Cryptate Carriers," *J. Chem. Soc.*

*Chem. Comm.*, 1988, 11:691–692.
Dixon et al., "Molecular Recognition: Bis–Acylguanidiniums Provide a Simple Family of Receptors for Phosphodiesters," *J. Am. Chem. Soc.*, 1992, 114:365–366.
Furuta et al., "Phosphate Anion Binding: Enhanced Transport of Nucleotide Monophosphates Using a Sapphyrin Carrier," *Journal of the American Chemical Society*, 1991, 113:6677–6678.
Furuta et al., "Enhanced Transport of Nucleosides and Nucleoside Analogues with Complementary Base–Pairing Agents," *Journal of the American Chemical Society*, 1991, 113:4706–4707.
Galán et al., "A Synthetic Receptor for Dinucleotides," *J. Am. Chem. Soc.*, 1991, 113:9424–9425.
Galán et al., "Selective Complexation of Adenosine Monophosphate Nucleotides By Rigid Bicyclic Guanidinium Abiotic Receptors," *Tetrahedron Letters*, 32(15):1827–1830, 1991.
Harriman et al., "Metallotexaphyrins: A New Family of Photosensitisers for Efficient Generation of Singlet Oxygen," *J. Chem. Soc. Chem. Commun.*, 1989, 314–316.
Hisatome et al., "Porphyrins Coupled with Nucleoside Bases. Synthesis and Characterization of Adenine– and Thymine–Porphyrin Derivatives," *Chemistry Letters*, 1990, 2251–2254.
Hosseini et al., "Multiple Molecular Recognition and Catalysis. A Multifunctional Anion Receptor Bearing an Anion Binding Site, an Intercalating Group, and a Catalytic Site for Nucleotide Binding and Hydrolysis," *J. Am. Chem. Soc.*, 1990, 112:3896–3904.
Hosseini et al., "Multiple Molecular Recognition and Catalysis. Nucleotide Binding and ATP Hydrolysis by a Receptor Molecule Bearing an Anion Binding Site, an Intercalator Group, and a Catalytic Site," *J. Chem. Soc. Chem. Commun.*, 1988, 9:596–598.
Kimura et al., "A Study of New Bis(macrocyclic polyamine) Ligands as Inorganic and Organic Anion Receptors," *J. Org. Chem.*, 1990, 55(1):46–48.

(List continued on next page).

Primary Examiner—Mukund J. Shah
Assistant Examiner—P. K. Sripada
Attorney, Agent, or Firm—Arnold, White & Durkee

[57] ABSTRACT

The present invention provides various covalently modified sapphyrin derivatives and conjugates, and also, polymers including sapphyrin or derivatives thereof. Disclosed are water soluble sapphyrins, including polyhydroxysapphyrins and sapphyrin-sugar derivatives; sapphyrin-metal chelating conjugates; sapphyrin nucleobase conjugates; and polymer supported sapphyrins. Novel sapphyrin dimers, trimers, oligomers and polymers are also described, which polymers may include repeating units of sapphyrin or sapphyrin derivatives alone, or may further incorporate other units such as nucleobases.

26 Claims, 29 Drawing Sheets

OTHER PUBLICATIONS

Kimura, "Macrocyclic Polyamines as Biological Cation and Anion Complexones—An Application to Calculi Dissolution," 113–141. 1990.

Král et al., "Synthetic Sapphyrin–Cytosine Conjugates: Carriers for Selective Nucleotide Transport at Neutral pH," *Journal of American Chemical Society*, 1992, 114:8704–8705.

Li and Diederich, "Carriers for Liquid Membrane Transport of Nucleotide 5'-Triphosphates," *J. Org. Chem.* 1992, 47:3449–3454.

Marks and Stojakowvic, "Large Metal Ion–Centered Template Reactions. Chemical and Spectral Studies of the Superphthalocyanine Dioxocyclopentakis (1–iminoisoindolinato)uranium(VI) and Its Derivatives," *J. Am. Chem. Soc.*, 1978, 1695–1705.

Rexhausen and Gossauer, "The Synthesis of a New 22 π–Electron Macrocyle:Pentaphyrin," *Che. Soc. Che. Commun.*, 1983, 6:275.

Schmidtchen, "A Non–Macrocyclic Host for Binding Organic Phosphates in Protic Solvents," *Tetrahedron Letters*, 1989, 30(34):4493–4496.

Seel and Vogtle, "Molecular Recognition and Transport of Nucleobases—Superiority of Macrobicyclid Host Molecules," *Angew, Chem. Int. Ed. Engl.*, 1991, 30(4):442–444.

Sessler et al., "Anion Binding: A New Direction in Prophyrin–Related Research," *Pure & Applied Chem.*, 65(3):393–398, 1993.

Sessler et al., "Cytosine Amine Derivatives," *J. Org. Chem.*, 1992, 47:826–834.

Sessler et al., "Enhanced Transport of Fluoride Anion Effected Using Protonated Sapphyrin as a Carrier," *J. Chem. Soc. Chem. Commun.*, 1991, 1732–1735.

Sessler et al., "In vitro photodynamic activity of diprotonated sapphyrin: a 22–π–electron pentapyrrolic prophyrin–like macrocycle," *Chemical Abstracts*, 1990, 112:348–349, 112:194584t.

Sessler et al., "A water–stable gadolinium (III) complex derived from a new pentadentate expanded porphyrin ligand," *Chemical Abstracts*, 1989, 11:720, 11:125716e.

Sessler et al., "Synthetic and Structural Studies of Sapphyrin, a 22–π–Electron Pentapyrrolic Expanded Porphyrin," *J. Am. Chem. Soc.*, 1990, 112:2810–2813.

Sessler et al., "An Expanded Porphyrin: The Synthesis and Structure of a New Aromatic Pentadentate Ligand," *J. Am. Chem. Soc.*, 1988, 110:5586–5588.

Shionoya et al., "Diprotonated Sapphyrin: A Fluoride Selective Halide Anion Receptor," *Journal of the American Chemical Society*, 1992, 114:5714–5722.

Tabushi et al., "Lipophilic Diammonium Cation Having a Rigid Structure Complementary to Pyrophosphate Dianions of Nucleotides. Selective Extraction and Transport of Nucleotides," *J. Am. Chem. Soc.*, 1981, 103:6152–6157.

Tohda et al., "Liquid Membrane Electrode for Guanosine Nucleotides Using a Cytosine–Pendant Triamine Host as the Sensory Element," *Analytical Chemistry*, 1992, 64(8):960–964.

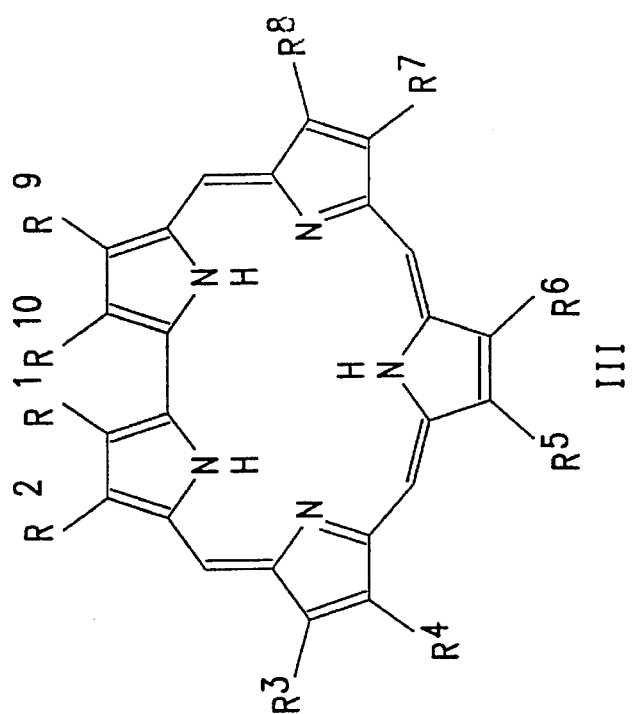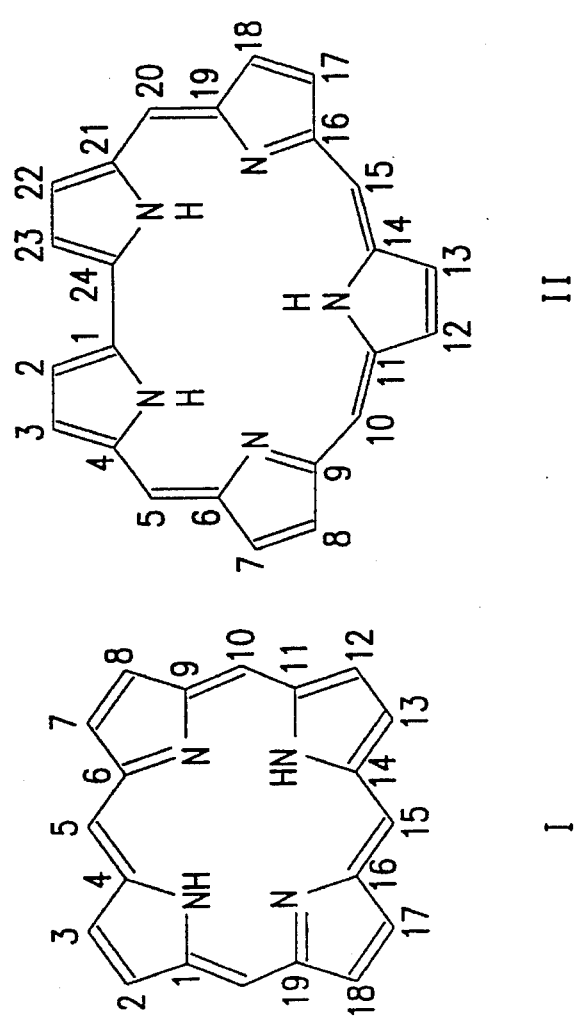
FIGURE 1C
FIGURE 1B
FIGURE 1A

III

1. $R^4$ or $R^7 = CH_2CH_2CON(CH_2CH_2OH)_2$

2a. $R^4$ or $R^7 = CH_2CH_2CO_2H$    2b. $R^4$ or $R^7 = CH_2CH_2CO_2CH_3$

3. $R^4$ or $R^7 = CH_2CH_2CONH-C(CH_2OH)_3$

4a. R = Ac   4b. R = Bz   4c. R = H

5. $R^4$ or $R^7 = CH_2CH_2CH_2OH$

6a. R = Ac   6b. R = H

7a. $R^5$ = $CH_2CH_2CO_2H$
7b. $R^5$ = $CH_2CH_2CO_2CH_3$

STRUCTURE 8

11 R = Bz

12

13 R = Bz
14 R = H

15

III

STRUCTURE IV

25

STRUCTURE V

STRUCTURE 27

$n = 1-200$
$R = H$ or ALKYL

POLYMER SUPPORTED SAPPHYRIN

GENERAL STRUCTURE VI

STRUCTURE VII

5,457,195

SAPPHYRIN DERIVATIVES AND CONJUGATES

The government owns rights in the present invention pursuant to NIH grant AI 28845.

This application is a continuation-in-part application of U.S. Ser. No. 07/454,298, filed Dec. 21, 1989, since issued as U.S. Pat. No. 5,159,065 on Oct. 27, 1992, the entire contents of which is incorporated by reference herein.

BACKGROUND OF THE INVENTION

1. Field of the Invention

The present invention relates generally to macrocyclic expanded porphyrin compounds, and particularly, to novel sapphyrin derivatives and conjugates, and polymers thereof. The covalently modified sapphyrin monomer derivatives of this invention include water soluble sapphyrins, such as polyhydroxysapphyrins and sapphyrin-sugar derivatives, sapphyrinmetal chelating derivatives, and sapphyrin nucleobase conjugates. The present invention also concerns polymer supported sapphyrins, and oligomers and polymers comprising sapphyrin or novel sapphyrin derivatives, either alone, or in combination with other units such as nucleobases.

2. Description of the Related Art

Expanded porphyrins are large pyrrole-containing macrocyclic analogues of the porphyrins (e.g. porphine, structure I, FIG. 1A). A number of expanded porphyrin systems are now known. However, only a few fully conjugated examples have been reported that contain more that four pyrrolic subunits, namely the smaragdyrins, sapphyrins, pentaphyrins, hexaphyrins, and superphthalocyanines[1] (Sessler & Burrel, 1991). Sapphyrin, in its generalized substituent-free form, is represented by structure II (FIG. 1B). Structure III (FIG. 1C) provides a generalized representation of β-substituted sapphyrins.

Sapphyrin, first discovered serendipitously by Woodward[2] is one of the more intriguing products to emerge from initial studies directed towards the synthesis of Vitamin $B_{12}$.[2,3] It is a 22 pi-electron pentapyrrolic macrocycle which exhibits an intense Soret-like band at about 450 nm ($CHCl_3$) along with weaker Q-type transitions in the 620 to 690 nm region. These optical properties, along with the presence of a large central cavity which serves for metal binding, renders sapphyrin useful for certain biomedical applications, including photodynamic therapy (PDT) and magnetic resonance imaging enhancement (MRI).

In addition to the above, certain expanded porphyrins, including especially those of the sapphyrin series, have been found to act as halide anion chelating agents in both solution and the solid state[4]. This finding, along with an appreciation, that the diprotonated form of 3,8,12,13,17,22-hexaethyl-2,7,18,23-tetramethylsapphyrin acts as an efficient carrier for the through-dichloromethane-membrane transport of nucleotide monophosphates, such as e.g. guanosine-5' monophosphate, and related entities at acidic pH[5], led the inventors to consider that the basic sapphyrin structure and related compounds such as the rubyrins, if suitably modified, could be used to bind, recognize, and transport phosphorylated entities at or near neutral pH.

Unfortunately, all sapphyrins known at the time of this invention were known both to be essentially insoluble in water and also known to be ineffective as through membrane carriers for phosphate monoesters including those specifically that define the class of compounds known as nucleotides and nucleotide analogues[5]. These two deficiencies limited the potential utility of sapphyrins for any applications associated with their use at or near neutral pH and, more generally, any conditions involving partial or complete association with an aqueous environment.

In addition, the sapphyrins known prior to the present invention were all of such simple character in terms of peripheral substituents, such that only hydrogen, alkyl and carboxy alkyl were known[1,6] that said systems, even if they were to demonstrate binding to nucleotides or nucleotides, would be expected to do so without any degree of specificity with regards the nature of the nucleic acid base ("nucleobase") attached to the phosphate core. Thus, at the time of this invention, it was considered that the development of a sapphyrin-derived species capable of binding, recognizing, and/or transporting a mononucleotide (or related entity) at or near neutral pH would represent a significant advance, especially if such system or systems could be made to achieve this binding, transport, or recognition in a nucleobase specific manner.

Furthermore, it was recognized that the synthesis of one or more water soluble sapphyrins would represent a considerable advantage, not only in terms of phosphate entity recognition and transport, but also because it would allow for a detailed study of the basic binding phenomena in aqueous media. This latter would be particular true if said water soluble sapphyrin were neutral in character.

A considerable number of ionic (e.g. phosphorylated) nucleotide analogues are known that exhibit antiviral activity in cell-free extracts and yet are inactive in vivo due to their inability to cross lipophilic cell membranes[7,8]. The anti-herpetic agent, acyclovir, is typical in that it enters the cell only in its uncharged nucleoside-like form. However, this compound is phosphorylated in the cytoplasm resulting in the active, ionic triphosphate species. In contrast, many other potential antivirals, including the anti-HIV agent, Xylo-G, are not phosphorylated intracellularly and are therefore largely or completely inactive[9]. If, however, the active monophosphorylated forms of these putative drugs could be transported into cells, it would be possible to fight viral infections with a large battery of otherwise inactive materials.

At present, no general set of nucleotide transport agents exists[10]. In early work, Tabushi was able to effect adenosine nucleotide transport using a lipophilic, diazabicyclooctane-derived, quaternary amine system[10a]. However, this same system failed to mediate the transport of guanosine 5'-monophosphate (GMP) or other guanosine-derived nucleotides. Since then, considerable effort has been devoted to the generalized problem of nucleic acid base ("nucleobase") recognition, and various binding systems have been reported.

Currently known nucleotide binding systems include various acyclic, macrocyclic, and macrobicyclic polyaza systems[10a–10n]; nucleotide-binding bis-intercalands[10k]; guanidinium-based receptors[10f,10n]; and various rationally designed H-bonding receptors[10o–10u]. These latter H-bonding receptors have been shown to be effective for the chelation of neutral nucleobase and/or nucleoside derived substrates but, without exception, have all proved unsatisfactory for the important task of charged nucleotide recognition. Thus, despite intensive efforts in this field, there is currently no synthetic system capable of effecting the recognition, or through-membrane transport, of phosphate-bearing species such as anti-viral compounds. Furthermore, there are presently no rationally designed receptors which are "tunable" for the selective complexation of a given nucleobase-derived system.

Not surprisingly, the transport of larger polyphosphorylated compounds across cellular membranes also poses significant problems. The difficulties in transporting oligonucleotides across the plasma membrane and into mammalian cells is one of the factors currently limiting the successful application of antisense technology to human therapy. Further limitations may also result from the dynamics of oligonucleotide recognition, binding and functional inhibition which occurs intracellularly, subsequent to any import that does occur.

There is clearly, therefore, a major need for novel drug delivery systems to be developed. Compounds which would allow negatively-charged (anionic) structures, particularly phosphate-bearing compounds, including nucleotides and nucleotide derivatives such as anti-viral compounds and anti-sense oligonucleotides, to be transported across naturally lipophilic cellular membranes would represent an important scientific and medical advance.

In addition to the delivery of compounds to cells, there still remains, obviously, considerable scope for the design of improved chemotherapeutic compounds which act upon DNA once inside a target cell. Since currently available chemotherapeutic agents have complex structures, or complicated modes of interaction with their targets that preclude systematic improvement, the development of a novel class of DNA binding compounds would open up new avenues for the design of improved therapeutics. In this regard, a class of compounds that can be modified in a number of different ways whilst maintaining their overall monomeric, or preferably polymeric, structure would be particularly advantageous. The same is true for compounds that can be activated by light, or other means, to produce singlet oxygen or hydroxyl radicals, once bound to DNA. These considerations provided the present inventors with further impetus for the design and synthesis of improved sapphyrins such as those embodied by the present invention.

SUMMARY OF THE INVENTION

The present invention addresses these and other shortcomings in the prior art through the synthesis of several novel monomeric and polymeric sapphyrin derivatives and other monomeric and polymeric compounds, based generally upon the sapphyrin molecule.

This invention encompasses new sapphyrin derivatives and conjugates and polymers thereof. In a general and overall sense, included within the novel compounds of the invention are covalently modified sapphyrin monomers of the following general types: water soluble sapphyrins, sapphyrin-metal chelating derivatives, sapphyrin nucleobase conjugates, polymer supported sapphyrins and sapphyrin polymers and oligomers. Oligomers and polymers will typically comprise sapphyrin or sapphyrin derivatives alone, or sapphyrin in combination with other units such as nucleobases, as well as complexes of sapphyrin-nucleobase polymers with oligonucleotides.

In general terms, sapphyrin derivatives of the present invention can be defined by the following general structure:

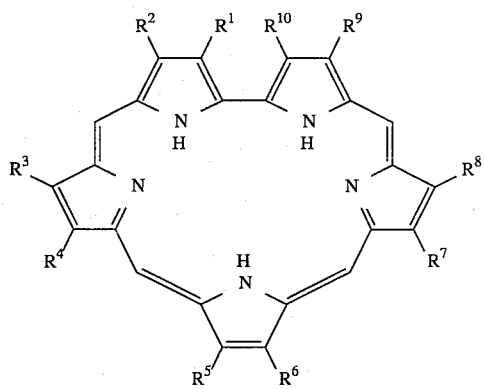

wherein each of $R^1$-$R^{10}$ is separately or collectively an H, alkyl, alkene, alkyne, halide, alkyl halide, hydroxyalkyl, glycol, polyglycol, thiol, alkyl thiol, aminoalkyl, carboxyalkyl, alkoxyalkyl, aryloxyalkyl, alkyloxycarbonyl, aryloxycarbonyl, aldehyde, ether, ketone, carboxylic acid, phosphate, phosphonate, sulfate, phosphate substituted alkyl, phosphonate substituted alkyl, or sulfate substituted alkyl, such that the total number of carbon atoms in each substituent R is less than or equal to 10.

The novel aspect of the foregoing structure is the fact that in the context of the present invention, at least one R group substituent of the foregoing general structure will be of the general formula X-B, wherein X is any sapphyrin compound and B is a substituent that 1) confers water solubility, 2) is a metal chelating compound, 3) is a nucleobase compound, 4) is a polymeric matrix or solid support, or 5) is a polymer or oligomer of sapphyrin or one of the foregoing sapphyrin derivatives.

The novel aspects of the invention may most readily be denoted through the use of the structure X—(CH$_2$)$_n$—A—(CH$_2$)$_m$—B, wherein X is any sapphyrin macrocycle, and A is CH$_2$, O, S, NH or NR$^{11}$, wherein R$^{11}$ is alkyl, alkene, alkyne, halide, alkyl halide, hydroxyalkyl, glycol, polyglycol, thiol, alkyl thiol, substituted alkyl, phosphate, phosphonate, sulfate, phosphate substituted alkyl, phosphonate substituted alkyl, sulfate substituted alkyl, COO, CONH, CSNH, or CONR$^{11}$.

The B substituent can include any alkene, alkyne, halide, alkyl halide, hydroxyalkyl, glycol, polyglycol, thiol, alkyl thiol, substituted alkyl, phosphate, phosphonate, sulfate, phosphate substituted alkyl, phosphonate substituted alkyl, sulfate substituted alkyl, hydroxyalkyl, sugar, sugar derivative, polysaccharide, metal chelating group, nucleobase, modified nucleobase, oligonucleotide, sapphyrin, sapphyrin derivative, polymeric sapphyrin, alkylating agent, steroid, steroid derivative, amino acid, peptide or polypeptide, polymeric matrix or solid support, and n is 0 to 10 and m is 0 to 10.

Certain particular embodiments of the invention relate to sapphyrin derivatives that are polyhydroxylated and therefore water-soluble. Water soluble sapphyrins are particularly desirable where one would like to exploit the various surprising properties of the sapphyrin macrocycle in connection with human or animal applications. The nature of the polyhydroxylation is not particularly critical to achieving water solubility of the sapphyrin derivative, so long as at least three or four hydroxyl groups per sapphyrin macrocycle are incorporated into the structure. The inventors have found that the introduction of at least 3 hydroxyl groups per macrocycle will be sufficient to achieve some degree of water solubility.

One means for introducing hydroxyl groups into the sapphyrin macrocycle structure is simply through the addition of alkyl substituents to the basic sapphyrin macrocycle unit, wherein the added substituents include one or more hydroxyl groups within their structures. Thus, exemplary polyhydroxylated sapphyrins will be those that are modified to include structures such as hydroxymethyl, hydroxyethyl, hydroxypropyl, hydroxybutyl, dihydroxyalkyl, trihydroxyalkyl, or the like, at one or more R positions of the basic sapphyrin structure shown above. Exemplary polyhydroxylated, water soluble sapphyrins are set forth in FIG. 2B, and are denoted as structures 1 and 3.

An alternative means of achieving polyhydroxylation is through the addition of sugar moieties such as a saccharide, polysaccharide, saccharide derivative or aminosaccharide, to the sapphyrin macrocycle structure. In such cases, it has been found that the addition of a single saccharide molecule to a sapphyrin macrocycle will achieve a degree of water solubility. These structures are referred to broadly herein as simply sapphyrin-sugar compounds, conjugates or derivatives. The nature of the sugar is not particular critical to the achievement of water solubility, and a non-exhaustive, exemplary list of useful sugars in this regard are set forth in Table I. Of course, any sugar or modified sugar may be employed including sugars having additional phosphate, methyl or amino groups and the like. Moreover, the use of both D- and L- forms, as well as the $\alpha$ and $\beta$ forms are also contemplated. Particularly preferred are sugars such as glucose, galactose, galactosamine, glucosamine and mannose. Exemplary structures in this category are denoted as structures 4, 4a, 4b, 4c, 6, 6a and 6b of FIG. 2B.

In other aspects, the invention concerns sapphyrin derivatives which incorporate a metal chelator moiety at the B position. It has been found that the addition of a chelator moiety confers exciting new properties onto the sapphyrin macrocycle, including most notably an ability to cleave DNA through an as yet unknown mechanism. This is exciting because it allows one to prepare sapphyrin macrocycles that have the ability to both bind to and cleave DNA. Thus, not only will such molecules have clear in vitro uses, such as for DNA shearing or cleaving, but it opens the door for in vivo uses. For example, it is quite possible that sapphyrin-chelator complexes will have the ability to bind to, and cleave, the DNA of blood-borne viruses. Alternatively, it is possible that these structures will be useful in disrupting enzymatic action, by competing for requisite metal cofactors or by cleaving proteins. It is posited that due to their strong attraction for charged phosphate groups, the sapphyrins of the present invention will be particularly useful in selectively cleaving phosphorylated proteins, which are known to play a role in expression and activation of gene products including oncogene products. These structures may also be useful in an in vivo context through their introduction into cells, where they would be expected by the present inventors to effect cleavage of intracellular DNA or RNA. It may even be possible to effect a base or sequence specific cleavage through modification of the sapphyrin macrocycle structure, such as by substituent modification.

In particular embodiments relating to chelator conjugates, the sapphyrin-chelator derivative will include a metal chelating group such as 1,10-phenanthralene, EDTA, EGTA, DTPA, DOTA, crown ether, azacrown, catecholate or ethylene diamine. An exemplary structure is set forth as structure 8 of FIG. 3B, wherein the conjugated chelating group is EDTA. This particular molecule has been found to cleave DNA in a fashion that results in a "ladder" effect upon gel electrophoresis of the fragments that are generated.

In still other embodiments, the present invention relates to what are referred to as sapphyrin-nucleobase conjugates. As used herein, the term "sapphyrin-nucleobase conjugate" is intended to refer broadly to any conjugate formed by the covalent conjugation of any sapphyrin macrocycle to any nucleobase. Moreover, as used herein the term "nucleobase" is intended to refer broadly to any moiety that includes within its structure a purine or pyrimidine, a nucleic acid, nucleoside, nucleotide, or any derivative of any of these. Thus, the term nucleobase includes adenine, cytosine, guanine, thymidine, uridine, inosine, or the like, bases, nucleotides or nucleosides, as well as any base, nucleotide or nucleoside derivative based upon these or related structures. A particular example of a useful nucleobase are the so-called antimetabolites that are based upon the purine or pyrimidine structure. These structures typically exert their biological activity as antimetabolites through competing for enzyme sites and thereby inhibiting vital metabolic pathways. However, in the context of the present invention, the inventors are employing the term "antimetabolite nucleobase" quite broadly to refer to any purine or pyrimidine-based molecule that will effect an anticellular, antiviral, antitumor or antienzymatic effect, regardless of the underlying mechanism. Exemplary structures are shown in Table 2, including preferred conjugates such as purine or pyrimidine antimetabolites such as FU, AraC, AZT, ddI, xylo-GMP, Ara-AMP, PFA or LOMDP.

In still further embodiments, the nucleobase component of sapphyrin-nucleobase conjugates will include a protected nucleobase having attached substituents that protect the nucleobase from inappropriate or undesirable chemical reaction. Examples include substituents such as 9-fluorenylmethyl carbonyl, benzyloxycarbonyl, 4-methoxyphenacyloxycarbonyl, t-butyl oxycarbonyl, 1-adamantyloxycarbonyl, benzoyl, N-triphenylmethyl, N-di-(4-methoxyphenyl)phenylmethyl, and the like.

It is contemplated that sapphyrin-nucleobase conjugates will have a wide variety of applications, ranging from their use as agents for selectively delivering an associated, biologically active nucleobase to a particular body or even subcellular locale. For example, in the case of antimetabolite nucleobases, it is contemplated that the sapphyrin-nucleobase conjugates will act to deliver the antimetabolite to subcellular sites through the DNA binding activity of the sapphyrin portion of the conjugate. Perhaps more importantly, it is recognized that many, many nucleobase antimetabolites can not be readily employed in therapy due to the fact that their charged nature inhibits their uptake by target cells, or otherwise inhibits or suppresses their unencumbered movement across biological membranes. Typically, this shortcoming is due to the presence of charged structures such as phosphates, phosphonates, sulfates or sulfonates on the nucleobase, which due to their charged nature prevents or inhibits their crossing of a biological membrane. It is proposed that sapphyrins of the present inventions can be employed as transport agents for carrying such nucleobases across membranes, (whether the nucleobase is directly conjugated to the macrocycle or simply complexed with it).

Generally speaking, in the context of sapphyrin-nucleobase constructs designed for drug delivery it will usually be the case that one will employ only one nucleobase-containing substituent for each sapphyrin macrocycle, however this is in no way a limitation upon the invention. For example, sapphyrin-nucleobase conjugates of the present invention may have any number of nucleobases or nucleobase oligomers or polymers attached.

The foregoing can be most readily appreciated through consideration of other embodiments and utilities that are contemplated by the inventors. For example, it has been surprisingly discovered by the inventors that sapphyrin-nucleobases which include a selected nucleotide nucleobase conjugate will serve to selectively bind, through hydrogen bonding interactions, the complementary nucleotide. Thus, a sapphyrin-nucleobase conjugate such as sapphyrin-adenine will selectively bind thymidine, presumably through a hydrogen bonding of the two nucleotides that is stabilized through the interaction of the charged phosphate groups of the hydrogen bonded nucleotide with the macrocycle structure. Such structures will likely have a wide variety of applications, such as intracellular carriers for nucleobases that are hydrogen bonded rather than being covalently attached. Furthermore, as discussed in more detail below, it is contemplated that polymers of sapphyrin-nucleobase conjugates can be employed to carry hydrogen bonded poly- or oligo-nucleotides into target cells through complementarity with the sequence of bases "encoded" on the sapphyrin-nucleobase polymer.

The foregoing general structure could be exemplified by the formulas:

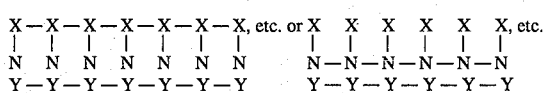

wherein X is the sapphyrin macrocycle, N is the conjugated nucleobase structure, and Y is the hydrogen bonded poly- or oligonucleotide.

Alternatively, it is contemplated that sapphyrins of the present invention may serve as a carrier for polymers of nucleobases, wherein the nucleobase polymers are attached covalently to the sapphyrin macrocycle, such as might be exemplified through the structural designation:

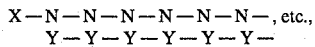

wherein X is a single sapphyrin macrocycle, and N is a selected oligomeric or polymeric nucleotide or other nucleobase, and Y is a hydrogen bonded poly- or oligonucleotide. Such a structure would be useful in a number of contexts, such as a specific carrier for complementary nucleotides such as antisense molecules.

Chemically speaking, any number of nucleobase structures can be attached to the sapphyrin macrocycle. The ultimate number of such residues that are attached will, of course, depend upon the application. Where one intends to employ such a structure to carry complementary nucleotides, one may well desire to employ a structure having a polymer of at least 10 or so bases attached. However, for other applications, such as for intracellular delivery of the nucleobase or other charged compounds of non-polymeric size, it may be convenient to design and employ sapphyrin-nucleobase constructs employing from one to three nucleobases per single macrocycle. Moreover, the nature of the intended use will dictate the number of attachment points there are on the sapphyrin macrocycle for attaching nucleobase moieties. Thus, it may typically be the case that a single attachment site will suffice for most applications, for certain particular applications those of skill may find it particularly advantageous to attach various nucleobases at various of the subcomponents of the macrocycle.

A number of the simpler sapphyrin-nucleobase conjugates contemplated by the inventors are set forth in FIG. 3, and serve as simple examples of the overall concept. Thus, for example, one may wish to refer to structures 9, 10, 11, 12, 13, 14, 15, 16, 17, 18, 19, and 20 of FIG. 3A and 3B.

As mentioned above, a particular aspect of the present invention involves the realization that novel sapphyrin structures may be prepared through the construction of sapphyrin polymers or oligomers. As used herein, the terms "sapphyrin polymer" or "polysapphyrin" are intended to refer to any compound which includes at least two sapphyrin macrocycles joined covalently. Moreover, the term "sapphyrin oligomer" or "oligosapphyrin" is intended to refer to sapphyrin-containing structures having a more defined length, such as from 2 or 3 up to 20, 30 or, at most, 40, sapphyrin units/molecule.

In still further embodiments, the invention concerns compositions which are composed of a sapphyrin derivative in accordance with any one of the embodiments discussed above complexed to a second compound, wherein the second compound includes within its structure a negatively charged phosphate, phosphonate, sulfate, or sulfonate moiety. More particularly, the second compound will be one that will bind to the sapphyrin by means of its negative charge, afforded by a sulfate, sulfonate, an ester of sulfate or sulfonate, a phosphate, a phosphate mono or diester, a phosphonate or phosphonate ester moiety.

In particular embodiments, the second compound will include a purine or pyrimidine, or an analog of either, within its structure. Exemplary structures include purine or pyrimidine antimetabolites such as FU, AraC, AZT, ddI, xylo-GMP, Ara-AMP, PFA or LOMDP. In other embodiments, the second compound of the composition will simply be DNA or RNA.

In still further embodiments, the invention concerns a method for forming a complex between a sapphyrin derivative and a second compound which includes within its structure a negatively charged phosphate, phosphonate, sulfate or sulfonate moiety, wherein the method involves preparing a sapphyrin derivative as described above; obtaining the second compound; and contacting the sapphyrin derivative with the second compound under conditions effective to allow the formation of a complex between the sapphyrin derivative and the second compound.

It will be appreciated by those of skill in the art that the invention is also generally applicable to the introduction of a sapphyrin molecule, alone or complexed with a second molecule, into an organism or, more generally, a cell contained within an organism. This may be employed as a means, for example, of successfully introducing the second compound (typically a charged compound) into the cell. An example might be introduction of a complex which includes an antimetabolic or antienzymatic compound such as an antiviral antimetabolic or antienzymatic compound, which one desires to introduce into a virally infected target cell. Another example would be the introduction of an antimetabolic or antienzymatic antitumor or antiproliferative compound that is introduced into a targeted tumor or proliferating cell. Of course, it is contemplated that the target cell may be located within an animal or human patient, in which case the complex is administered in effective amounts in an effective manner to the patient.

Generally speaking, it is contemplated by the inventors that useful pharmaceutical compositions of the present invention will include the selected sapphyrin derivative (which preferably incorporates a water soluble sapphyrin macrocycle) in a convenient amount that is diluted in a physiological buffer, such as phosphate buffered saline. The route of administration and ultimate amount of material that is administered to the patient or animal under such circumstances will depend upon the intended application and will be apparent to those of skill in the art in light of the examples which follow. Preferred routes of administration will typically include parenteral or topical routes.

In still further embodiments, the invention concerns a method of cleaving DNA comprising preparing a sapphyrin-chelator derivative and contacting DNA with said sapphyrin under conditions effective to promote cleavage of the DNA.

BRIEF DESCRIPTION OF THE DRAWINGS

Throughout all the figures and text of the present specification roman numerals are employed to indicate a general structure for which alternative substituents are possible, whereas arabic numbers are employed when referring to a specific compound.

In Structure III: $R^1$–$R^{10}$ may be H, alkyl, alkene, alkyne, halide, alkyl halide, hydroxyalkyl, glycol, polyglycol, thiol, alkyl thiol, aminoalkyl, carboxyalkyl, alkoxyalkyl, aryloxyalkyl, alkyloxycarbonyl, aryloxycarbonyl, aldehyde, ether, ketone, carboxylic acid, phosphate, phosphonate, sulfate, phosphate substituted alkyl, phosphonate substituted alkyl, or sulfate substituted alkyl; such that the total number of carbon atoms in each substituent, R, is less than or equal to 10. The novelty of these sapphyrin derivatives lies in the fact that at least one of the R ($R^1$–$R^{10}$) will be of the formula $(CH_2)_n$—A—$(CH_2)_m$—B; wherein A may be $CH_2$, O, S, NH or $NR^{11}$, wherein $R^{11}$ is alkyl, alkene, alkyne, halide, alkyl halide, hydroxyalkyl, glycol, polyglycol, thiol, alkyl thiol, substituted alkyl, phosphate, phosphonate, sulfate, phosphate substituted alkyl, phosphonate substituted alkyl, sulfate substituted alkyl, COO, CONH, CSNH, $CONR^{11}$; and wherein B may be alkene, alkyne, halide, alkyl halide, hydroxyalkyl, glycol, polyglycol, thiol, alkyl thiol, substituted alkyl, phosphate, phosphonate, sulfate, phosphate substituted alkyl, phosphonate substituted alkyl, sulfate substituted alkyl, hydroxyalkyl, sugar, sugar derivative, polysaccharide, metal chelating group, nucleobase, modified nucleobase, oligonucleotide, sapphyrin, sapphyrin derivative, polymeric sapphyrin, polymeric matrix, solid support, alkylating agent, steroid, steroid derivative, amino acid, peptide or polypeptide, and n and m are integers <10 or zero.

Figure 2A:
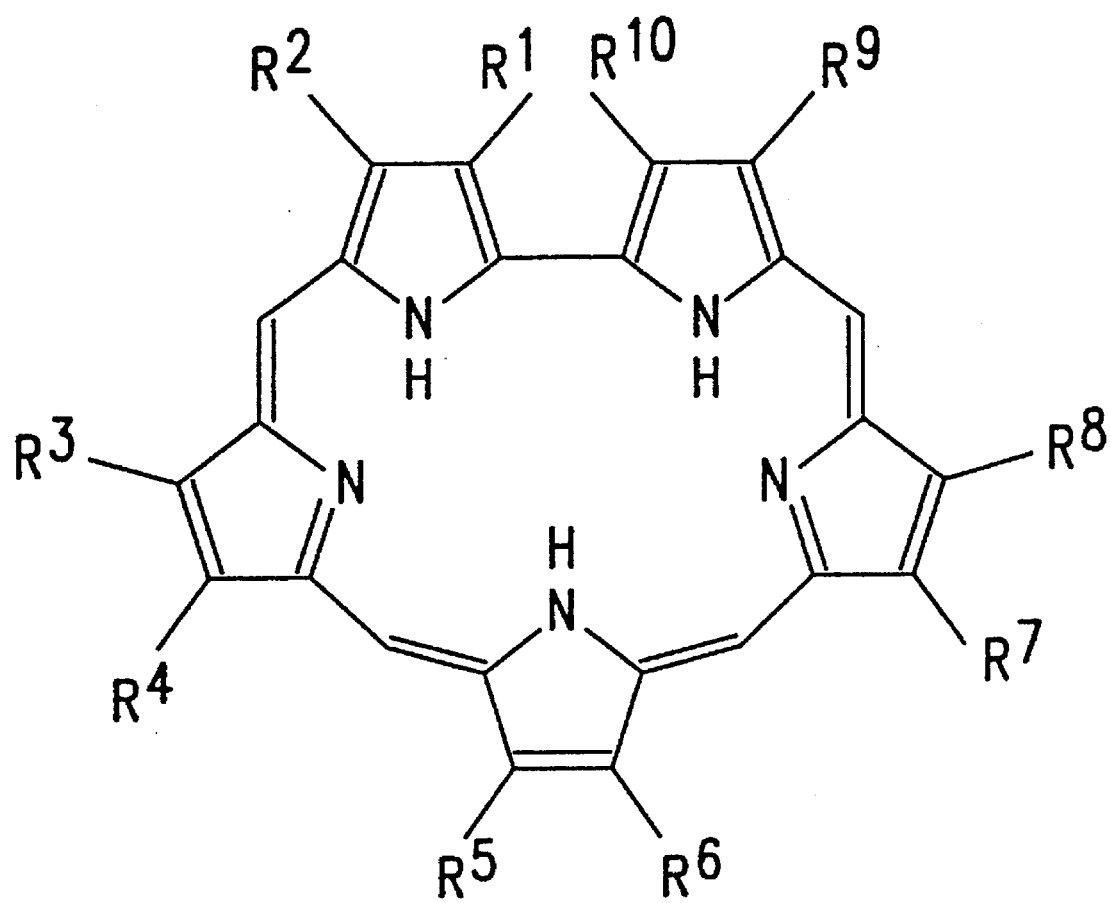
Figure 2B:
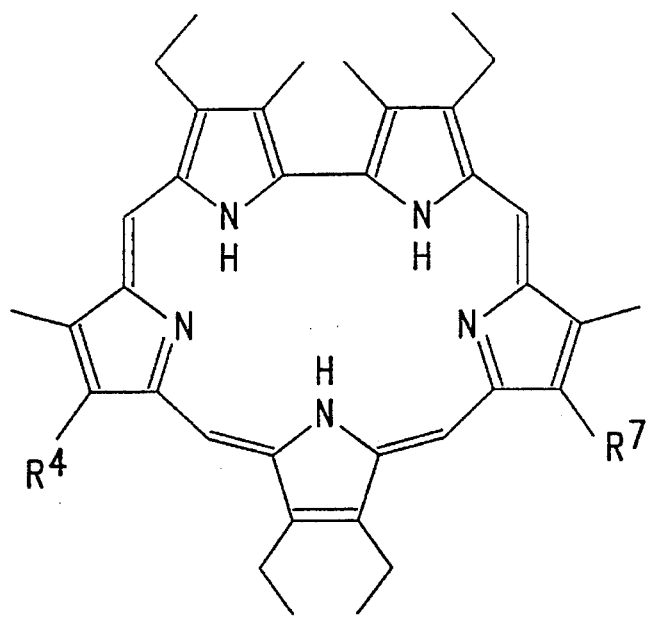
Figure 2B:
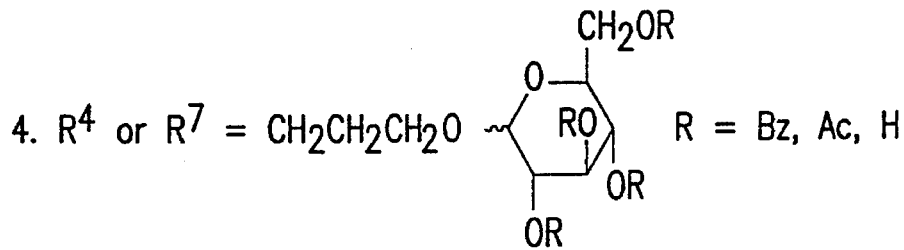
Figure 2B:
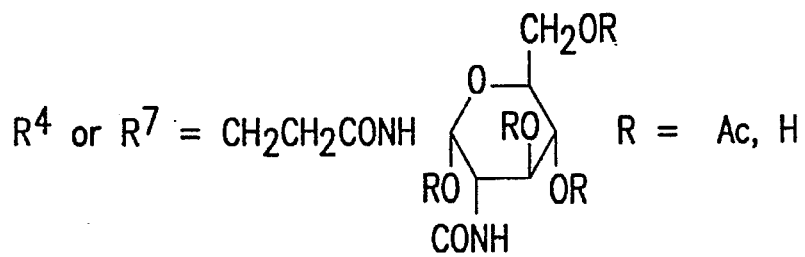

FIGS. 2A and 2B. Water-soluble sapphyrins. FIGS. 2A and 2B represent examples of the two categories of water-soluble sapphyrins, namely, polyhydroxysapphyrins and sapphyrin-sugar derivatives. In that these structures are generally based upon structure III, it will be understood that $R^1$–$R^{10}$ may include any of the groups listed above, and that at least one of the R ($R^1$–$R^{10}$) will be of the formula $(CH_2)_n$—A—$(CH_2)_m$—B; wherein, again, A may include any of the groups listed above and B will provide the water-soluble polyhydroxy moiety (sugar or non-sugar).

Specific examples of water-soluble polyhydroxysapphyrins include, but are not limited to, compounds such as 1 and 3, which were synthesized from the starting compounds 2a and 2b. Specific examples of water-soluble sapphyrin-sugar derivatives include, but are not limited to, compounds such as 4a–4c and 6, which were synthesized from the starting compounds 2 and 5. Any sugar or sugar derivative, such as those listed in Table 1, may be coupled to sapphyrin to form a water-soluble sapphyrin-sugar derivative in accordance herewith.

Figures 1, 4A:
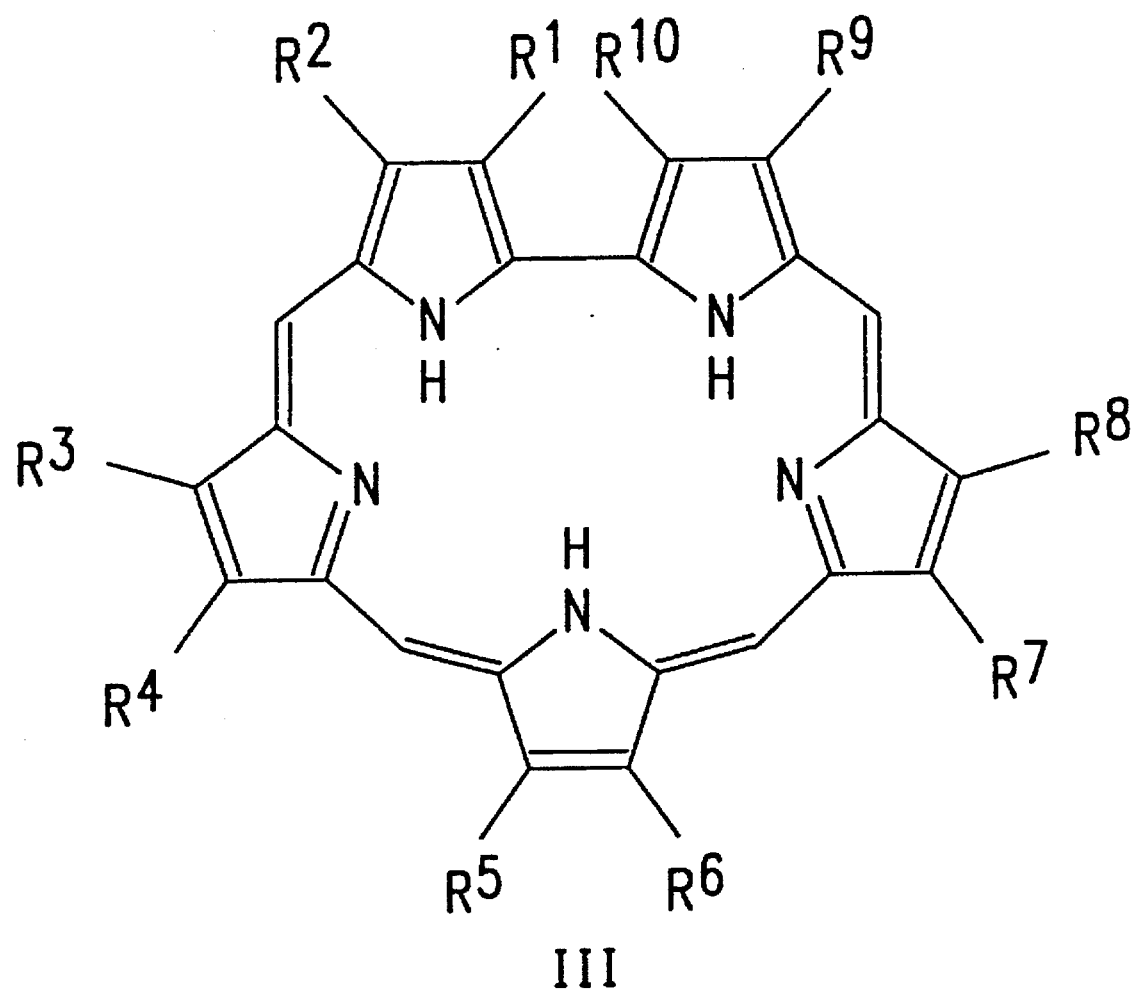
Figures 2, 4A:
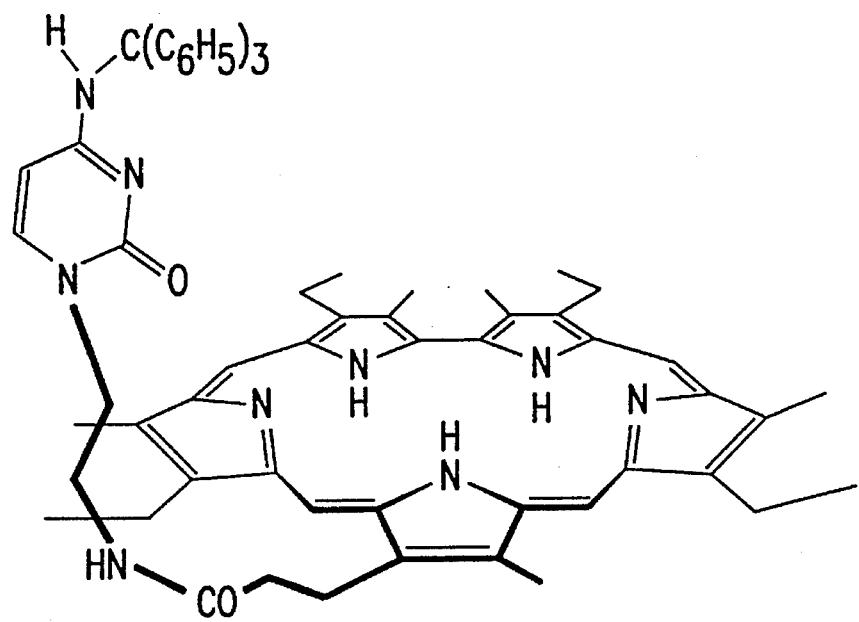
Figures 3, 4A:
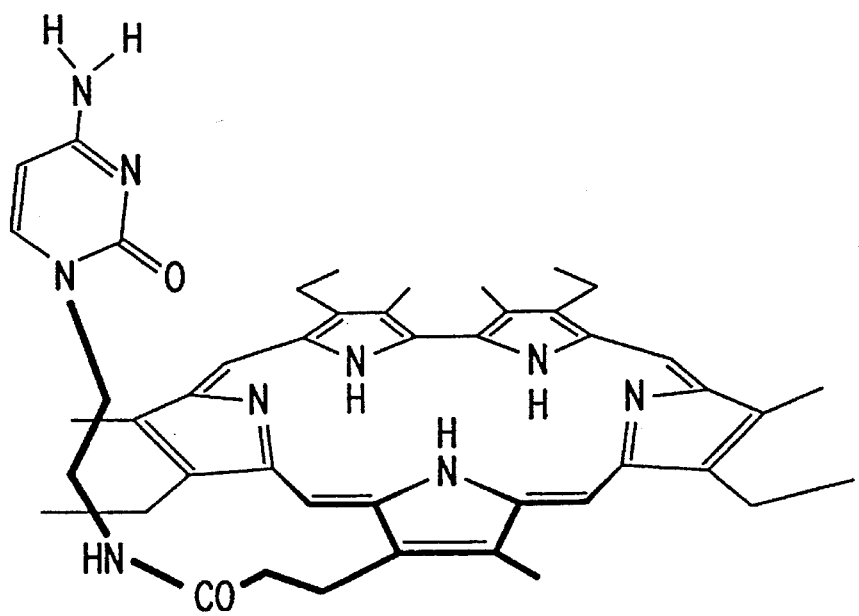

FIG. 3. Sapphyrin-metal chelating group conjugates. Sapphyrin may be conjugated to a metal chelating moiety such as, for example, EDTA, EGTA, DTPA, DOTA, ethylene diamine, bipyridine, 1,10-phenanthralene, crown ether, aza crown, catechols, and the like. $R^1$–$R^{10}$ may include any of the groups listed above, and at least one of these R groups will be of the formula $(CH_2)_n$—A—$(CH_2)_m$—B; wherein A may include any of the groups listed above and B will be a metal chelating moiety, for example, one of those listed above, such as EDTA, ethylene diamine or 1,10-phenanthralene.

Structure 8 is a specific example in which sapphyrin is conjugated to EDTA (the precursors for which compound are represented by structures 7a and 7b).

Figures 4, 4A:
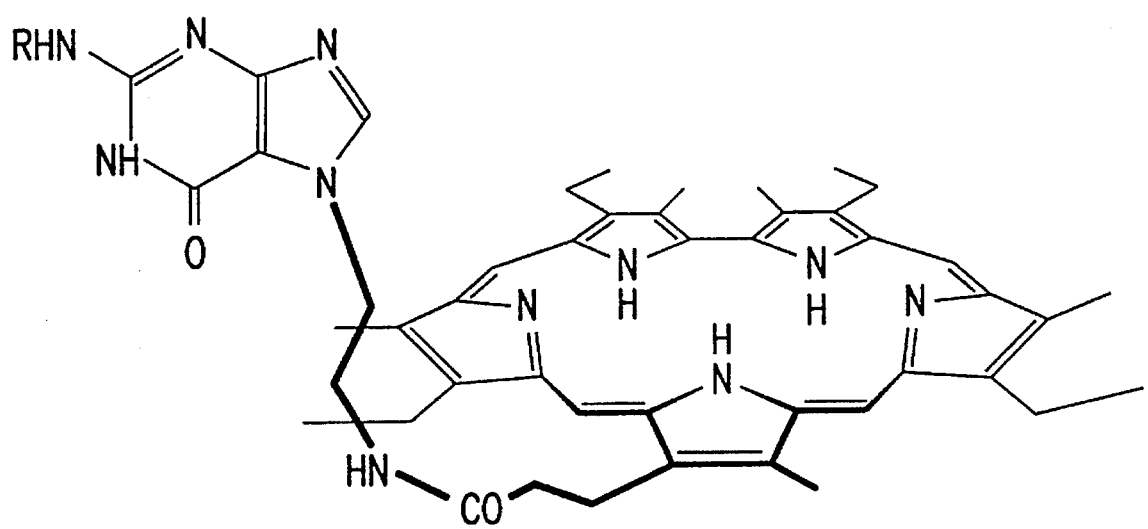

FIG. 4. Sapphyrin nucleobase derivatives. The sapphyrin nucleobase monomer derivatives of the present invention include both ditopic and tritopic sapphyrin receptors in which one or two nucleobases, respectively, are appended to the sapphyrin core. Again, $R^1$–$R^{10}$ may include any of the groups listed above, and at least one of these R groups will be of the formula $(CH_2)_n$—A—$(CH_2)_m$—B; wherein A may include any of the groups listed above and B will be one or more nucleobases, nucleobase derivatives or protected nucleobases. Conjugation of a nucleobase to a sapphyrin derivative to form a mononucleobase sapphyrin conjugate may be via any of the R groups $R^1$–$R^{10}$. Conjugation of the two separate nucleobases to a sapphyrin derivative to form a dinucleobase sapphyrin conjugate may also be via any two of the R groups $R^1$–$R^{10}$. However, it is contemplated that the creation of a symmetrical molecule, such as by substitution on $R^4$ and $R^7$, or $R^5$ and $R^6$, will be generally be preferred. The sapphyrin nucleobase derivatives may include any of the naturally-occurring purine or pyrimidine nucleobases, namely, cytosine, guanine, thymidine, adenine or uridine. Alternatively, they may include modified versions of any of these, such as those listed in Table 2; or chemically modified nucleobases such as "protected" bases including, for example, a protecting group on the amino group of the nucleobase, such as, for example, 9-fluorenylmethylcarbonyl, benzyloxycarbonyl, 4-methoxyphenacyloxycarbonyl, t-butyloxycarbonyl, 1-adamantyloxycarbonyl, benzoyl, N-triphenylmethyl, N-di-(4-methoxyphenyl)phenylmethyl.

FIG. 4A-1 through 4A-7: Sapphyrin mononucleobase derivatives. Specific examples of sapphyrin mononucleobase derivatives include, but are not limited to, structures 9–15; for example, the cytosine-containing compound, 10; and the guanine-containing compounds 12, 14 & 15.

FIG. 4B-1 through 4B-5: Sapphyrin dinucleobase derivatives. These sapphyrin derivatives may also include any of the naturally-occurring purine or pyrimidine nucleobases in any combination (fifteen possible combinations), or any nucleobase derivatives or chemically modified nucleobases, such as those listed above. Specific examples of sapphyrin dinucleobase conjugates include, but are not limited to, structures 16–20; for example, compound 20, containing two cytosine groups; compound 18, containing two guanine groups; and compound 16, a heteronucleobase sapphyrin conjugate.

Figures 4, 4A, 5:
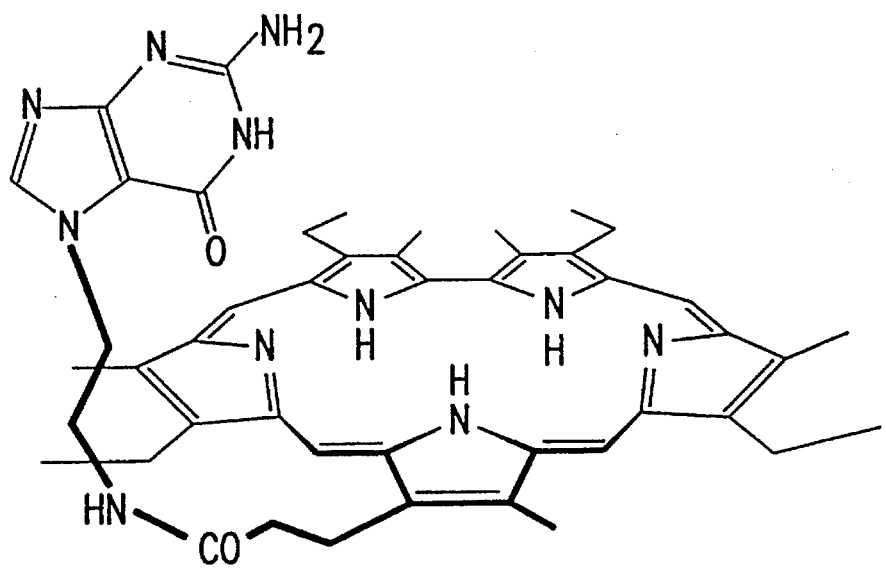
Figures 4, 4A, 5, 6:
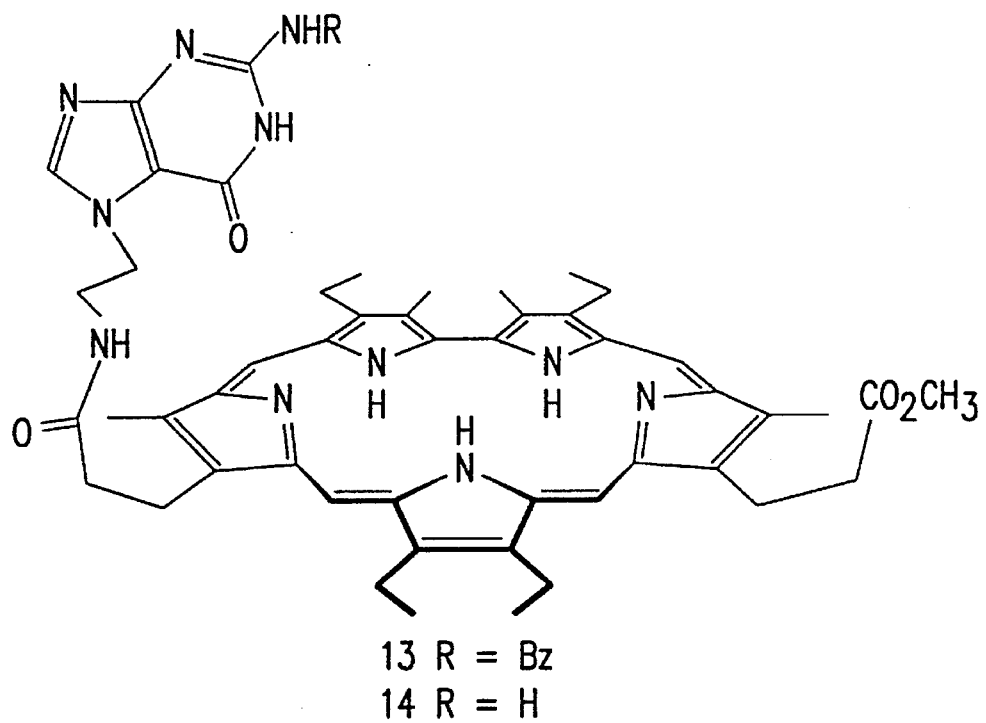
Figures 4, 4A, 5, 6, 7:
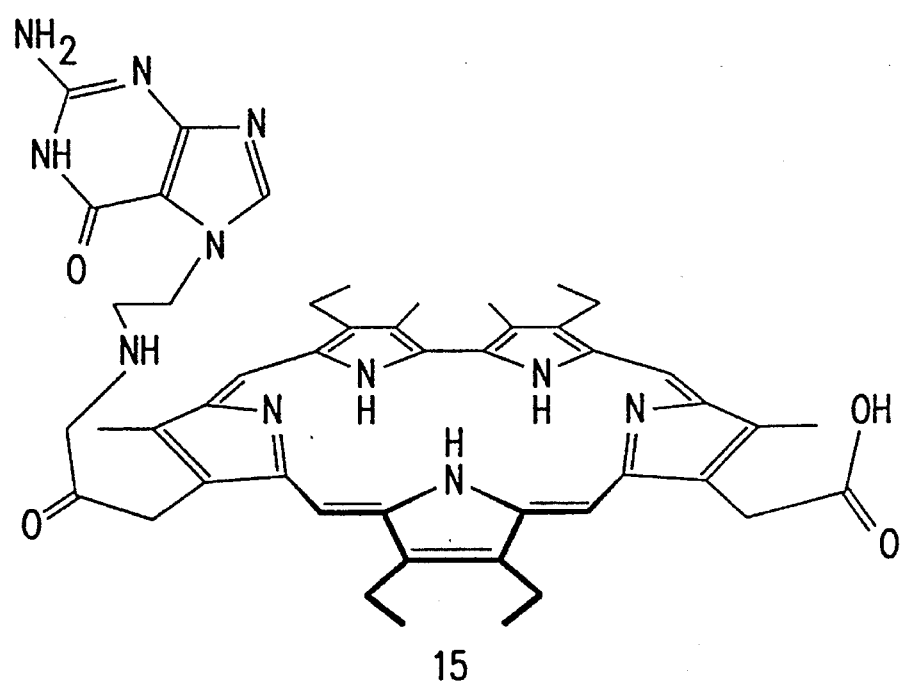
Figures 1, 4B:
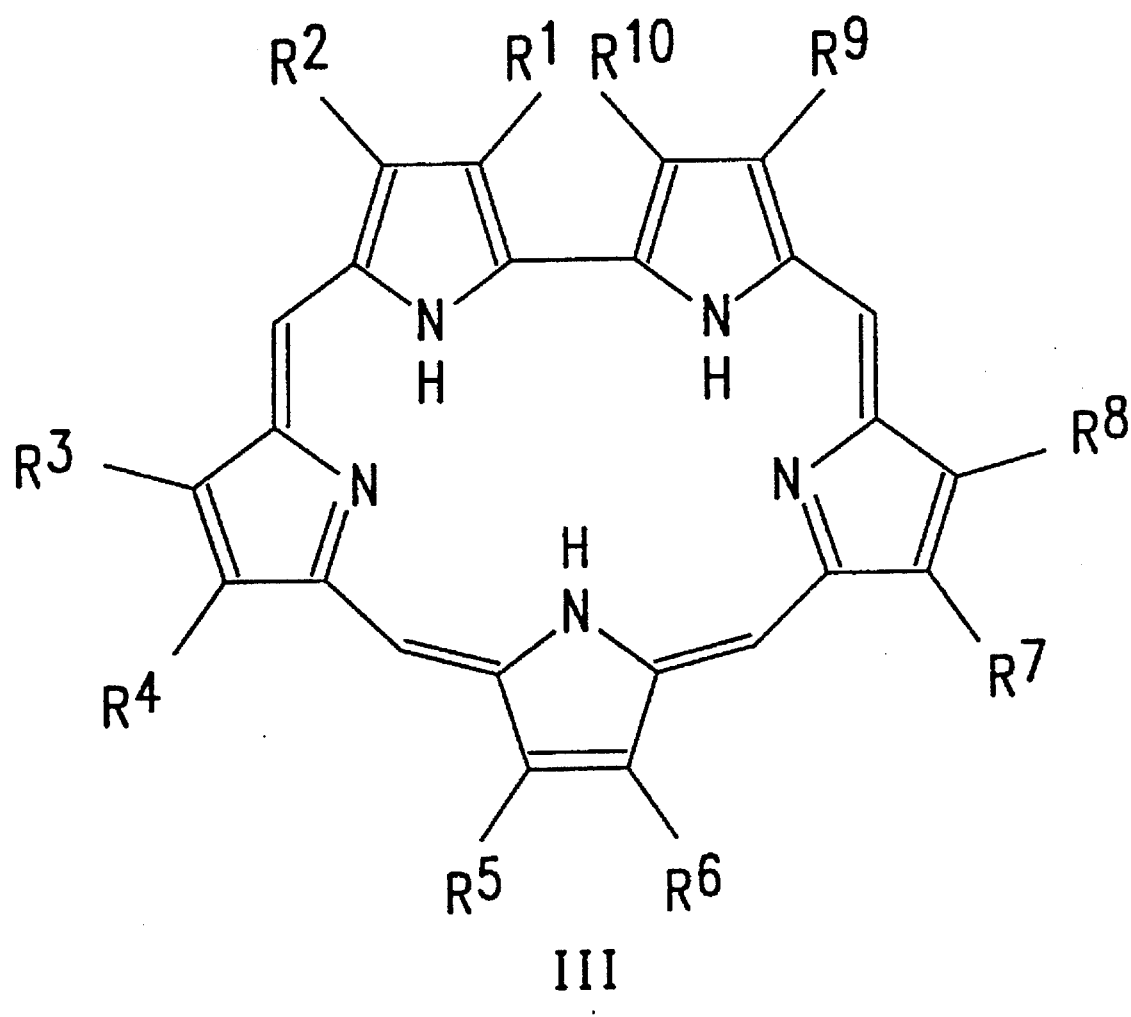
Figures 2, 4B:
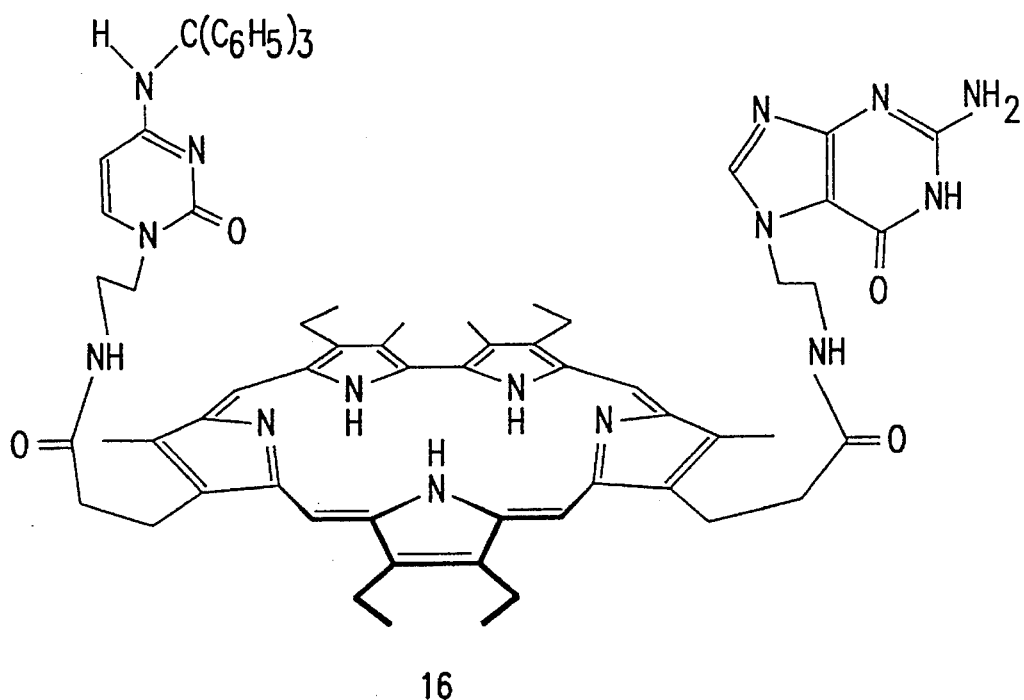
Figures 3, 4B:
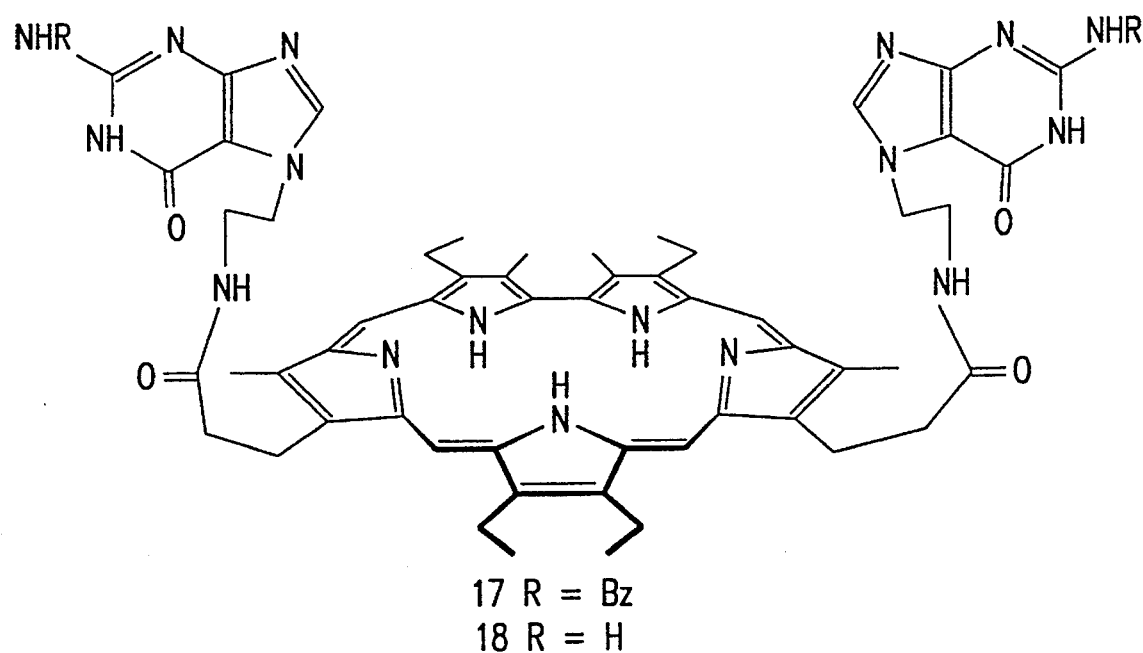
Figures 4, 4B:
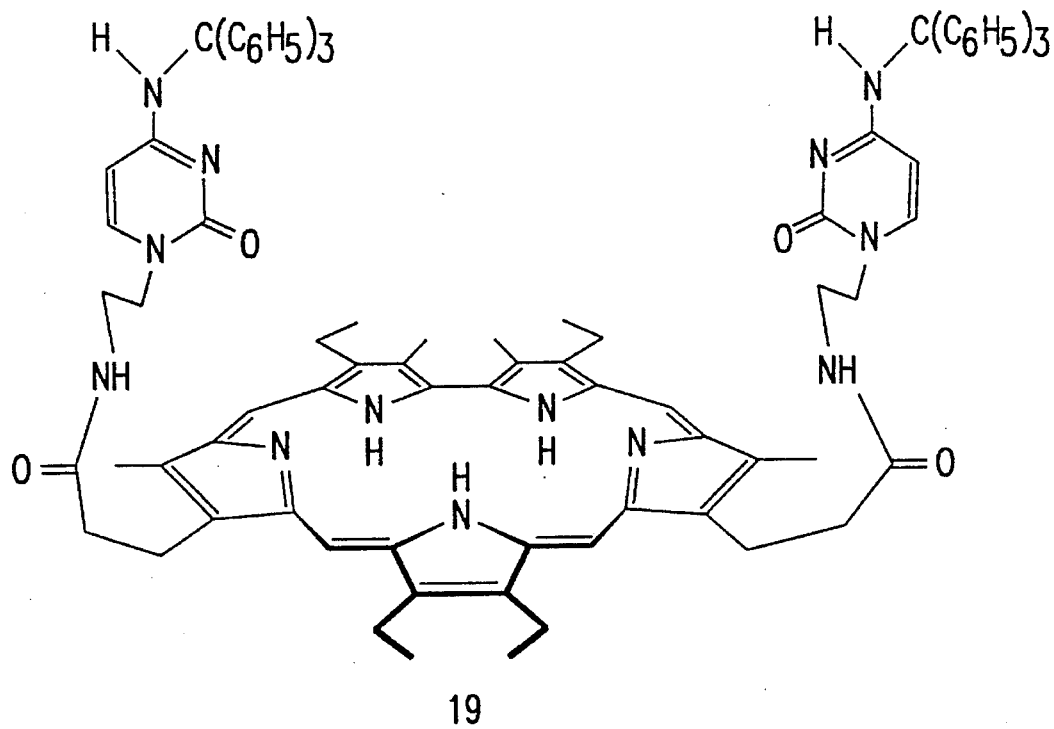
Figures 4, 4B, 5:
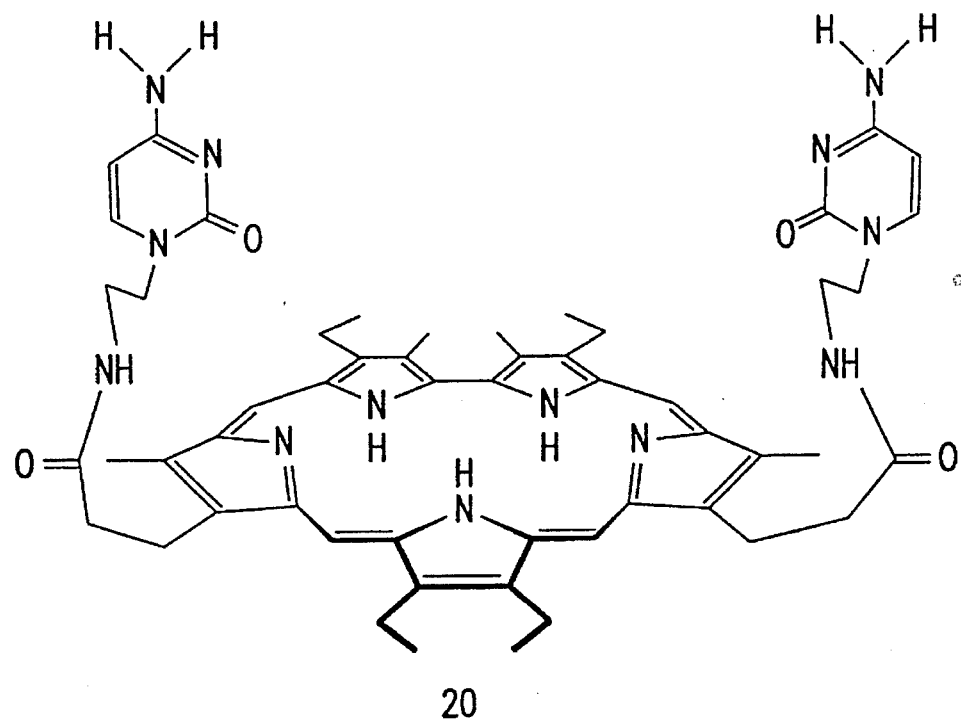
Figure 4C:
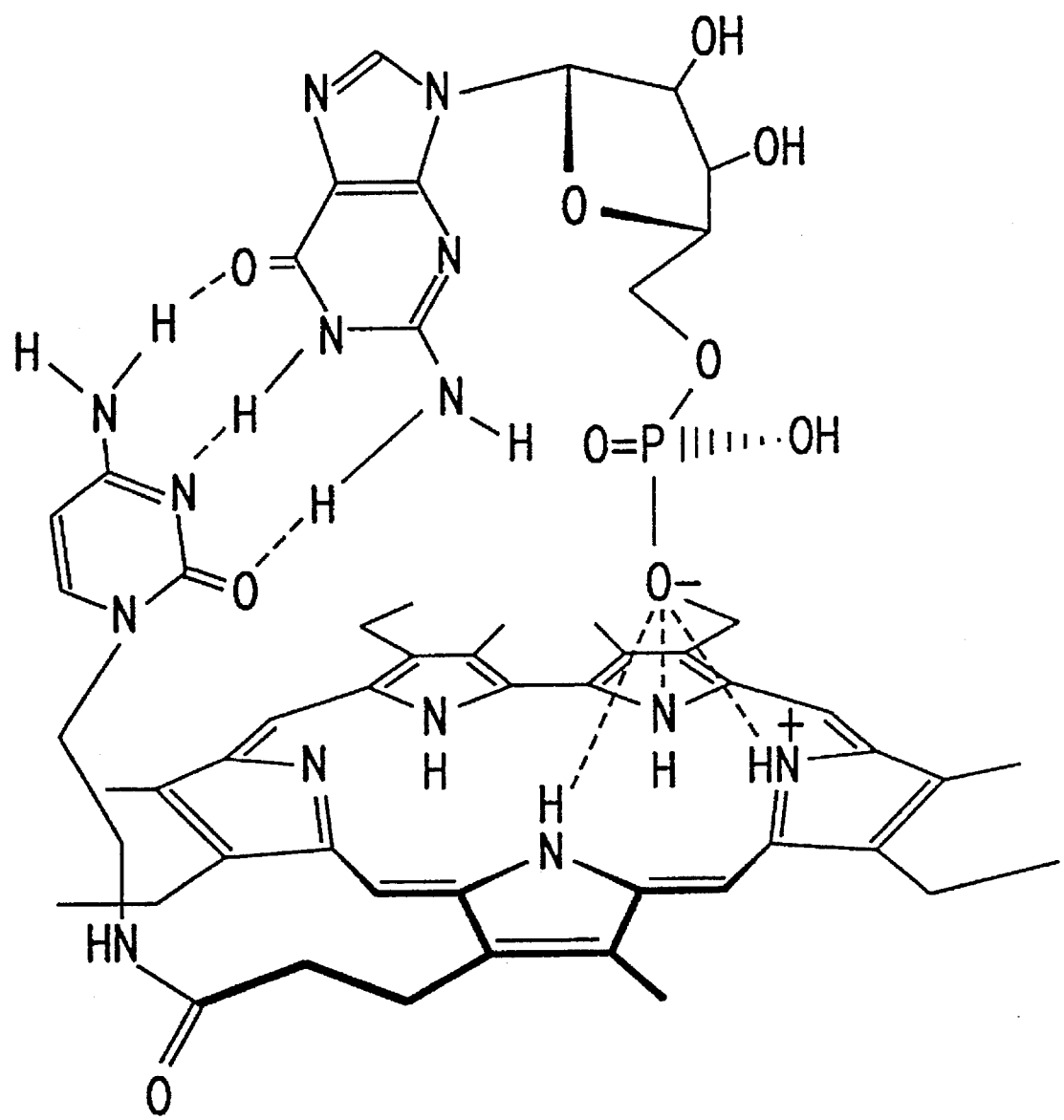

FIG. 4C. A possible structure for the proposed supramolecular complex formed between conjugate 10 and monobasic GMP.

FIG. 5. Sapphyrin oligomers and polymers.

Figure 5A:
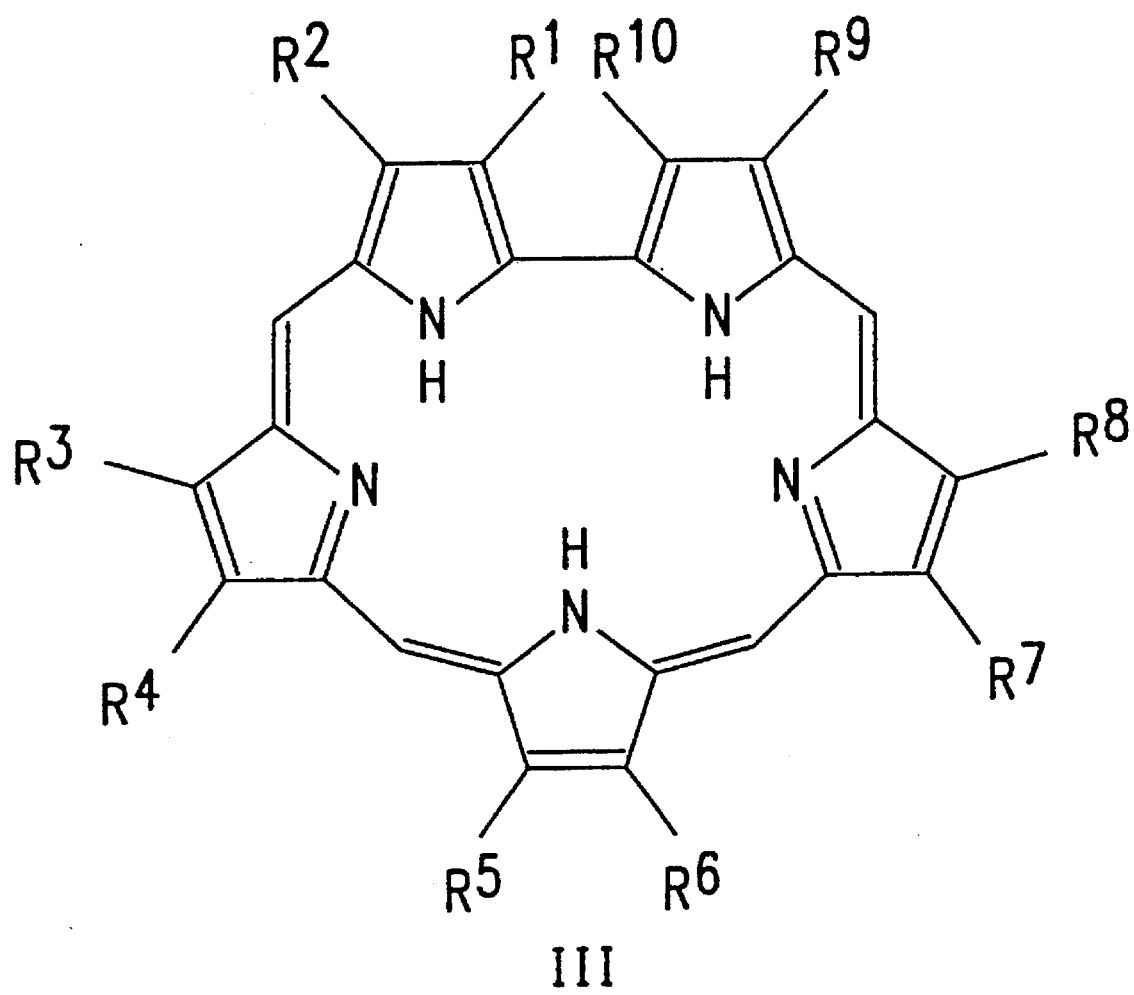

FIG. 5A: The sapphyrin molecules of the general structure III may be derivatized to include further sapphyrins or sapphyrin derivatives, oligosapphyrin derivatives, oligonucleotides or polymeric matrices, thus creating sapphyrin oligomers and polymers. As with the other novel sapphyrins, $R^1$–$R^{10}$ may include any of the groups listed above, wherein at least one of these R groups will be of the formula $(CH_2)_n$—A—$(CH_2)_m$—B, with A being any of the groups listed above. In these cases, B will be a sapphyrin, sapphyrin derivative, oligosapphyrin, polysapphyrin, oligonucleotide or any polymer, polymeric matrix or solid support. Conjugation of further derivatives to form a sapphyrin oligomer or polymer may be via any of the R groups $R^1$–$R^{10}$, with $R^4$, $R^5$ and $R^7$ being preferred targets. Conjugation at more than one point is also contemplated and may be via any two, or more, of the R groups $R^1$–$R^{10}$, such as $R^4$ and $R^7$, $R^3$ and $R^8$, or $R^5$ and $R^6$.

FIG. 5B-1 through 5B-6: Structure IV represents the general structure for the oligomeric sapphyrins of this invention, and is an example of structure III, wherein a further sapphyrin derivative has been added. Structure IV includes $R^1$–$R^{18}$, which may be any of the groups listed above, and also "C" which is a spacer group which may be H, O, S, NH, $NR^{19}$, wherein $R^{19}$ is alkyl, alkene, alkyne, halide, alkyl halide, hydroxyalkyl, glycol, polyglycol, thiol, alkyl thiol, substituted alkyl, phosphate, phosphonate, sulfate, phosphate substituted alkyl, phosphonate substituted alkyl, sulfate substituted alkyl, COO, CONH, CSNH, $CONR^{11}$; alkyl, alkene, polyene, alkyne, aryl, alkyl halide, hydroxyalkyl, glycol, polyglycol, sulfide, disulfide, alkyl thiol, aminoalkyl, carboxyalkyl, alkoxyalkyl, aryloxyalkyl, alkyloxycarbonyl, aryloxycarbonyl, aldehyde, dialkyl, ether, ketone, ester, phosphate, phosphonate, sulfate, phosphate substituted alkyl, phosphonate substituted alkyl, or sulfate substituted alkyl. Specific examples of sapphyrin oligomers include, but are not limited to, the dimeric sapphyrin structures 21–23, and the trimeric sapphyrin structure 24. Structure 25 represents a sapphyrin derivative which was employed as a precursor in sapphyrin oligomer and sapphyrin polymer syntheses.

Figures 1, 3A:
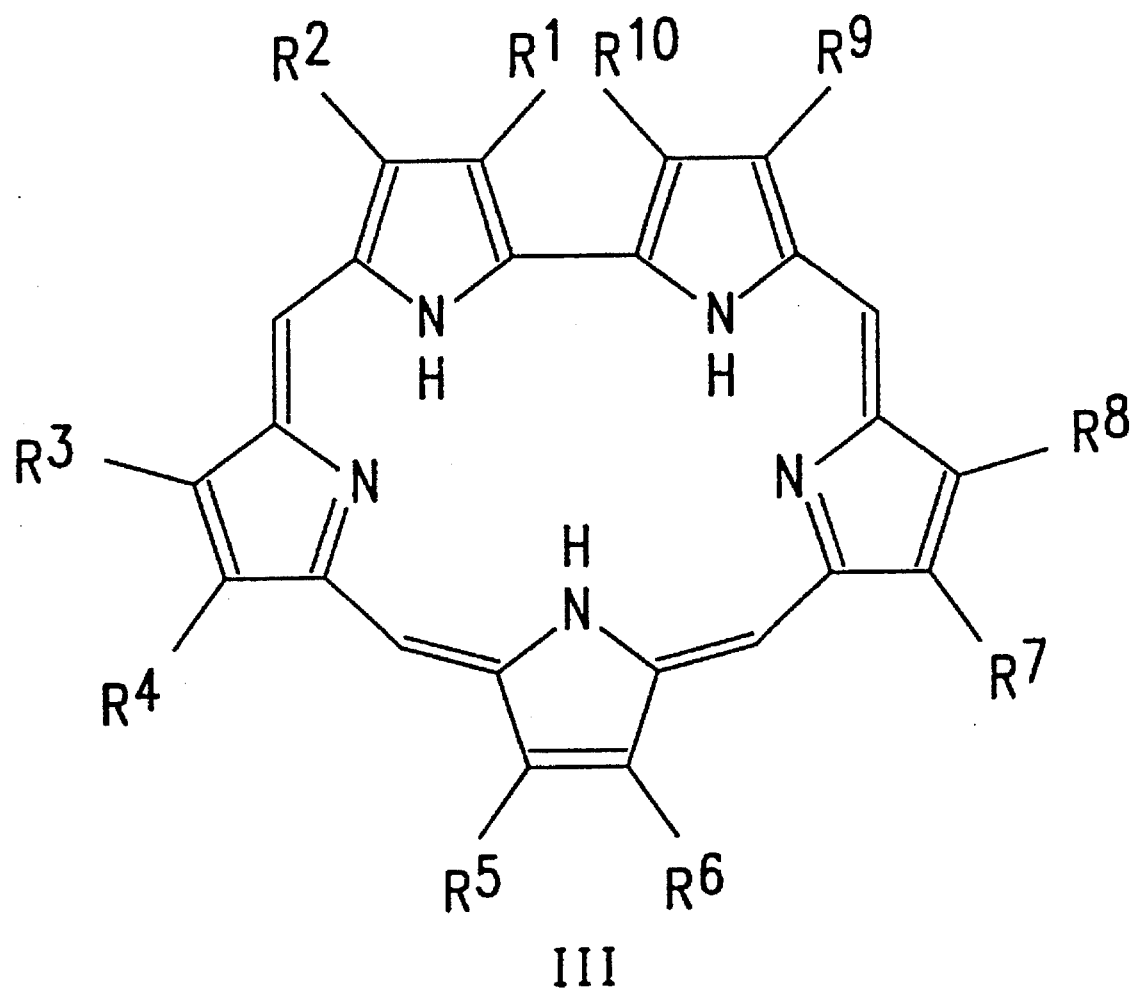
FIGS. 1A, 1B and 1C. Porphyrins and expanded porphyrins (large pyrrole-containing macrocyclic porphyrin analogues). Structure I, porphine; structure II, sapphyrin. Compounds I and II are represented in their generalized substituent-free forms, and show the standard numbering scheme. Structure III will be used throughout as a basis to define the novel sapphyrin derivatives, and polymers thereof, of the present invention.
Figures 1, 5B:
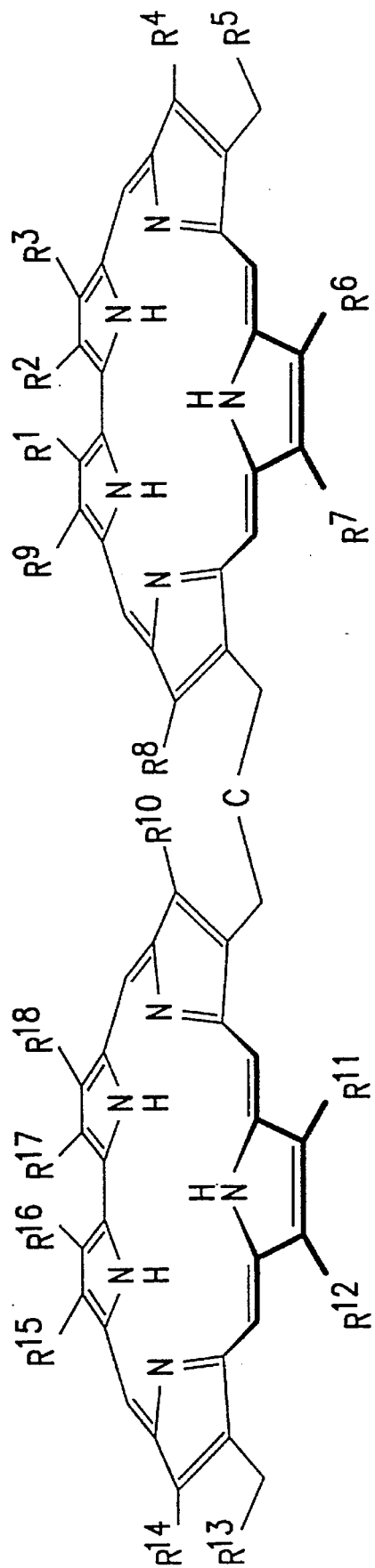
Figures 2, 5B:
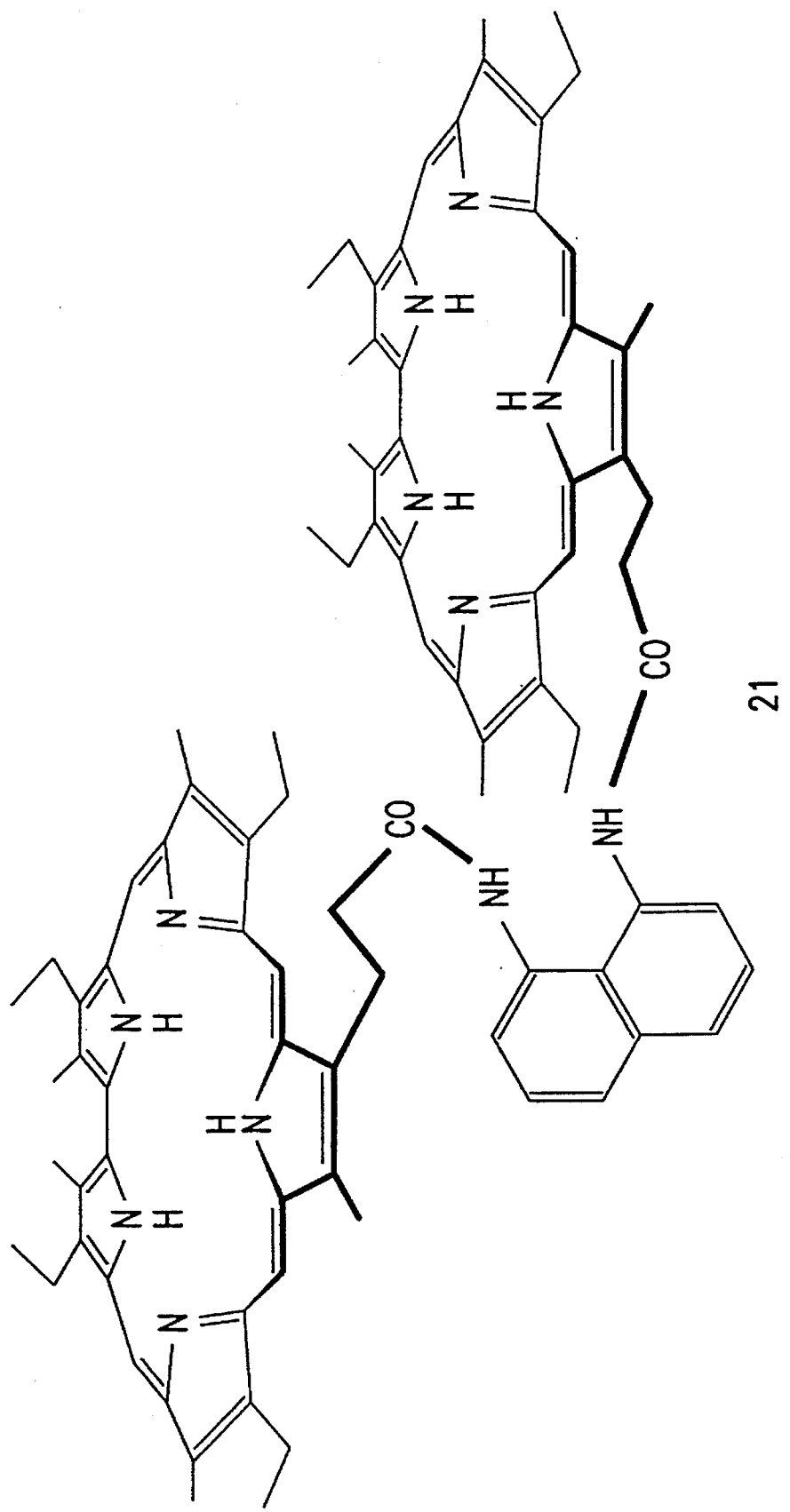
Figures 3, 5B:
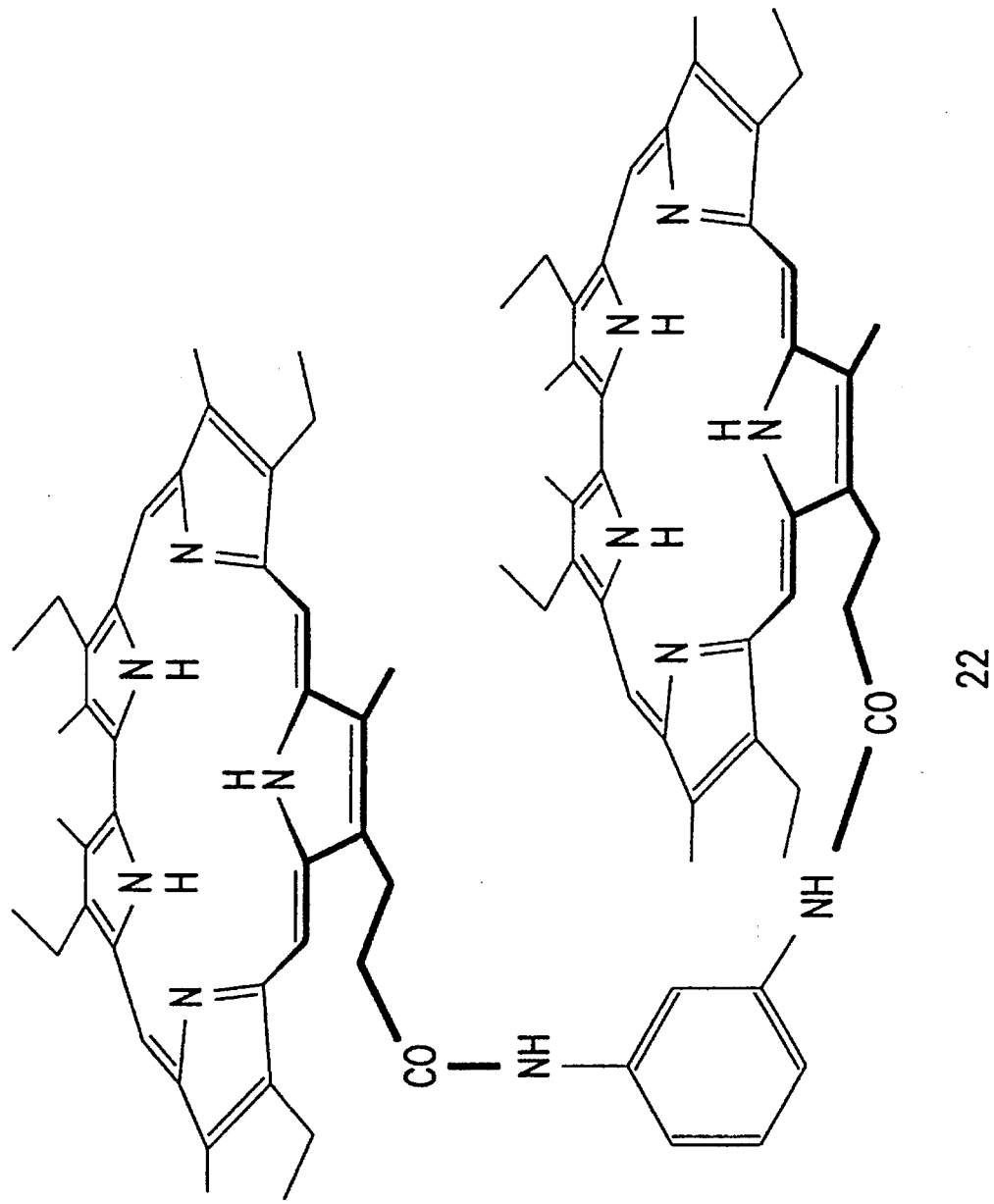
Figures 4, 5B:
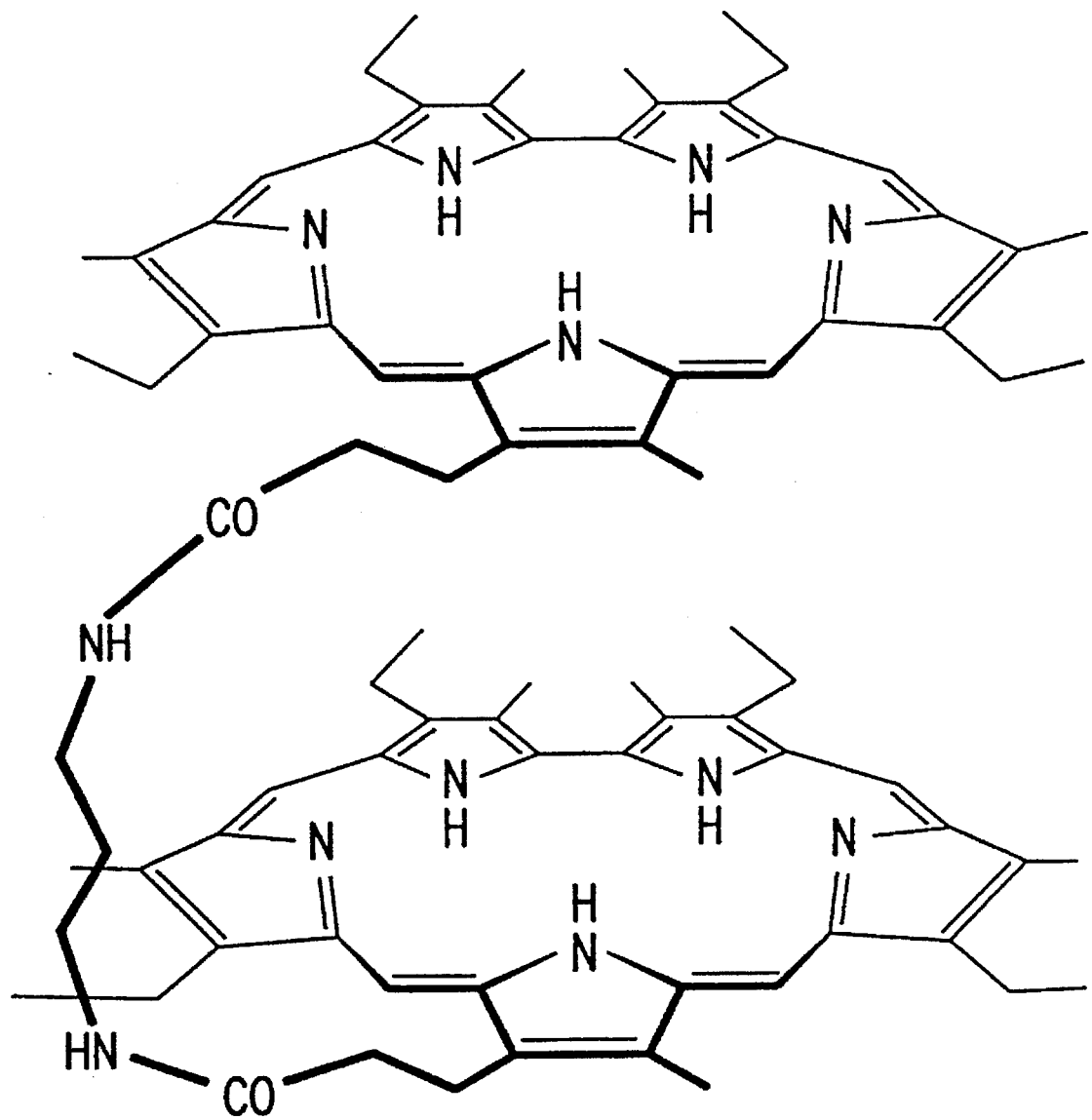
Figures 5, 5B:
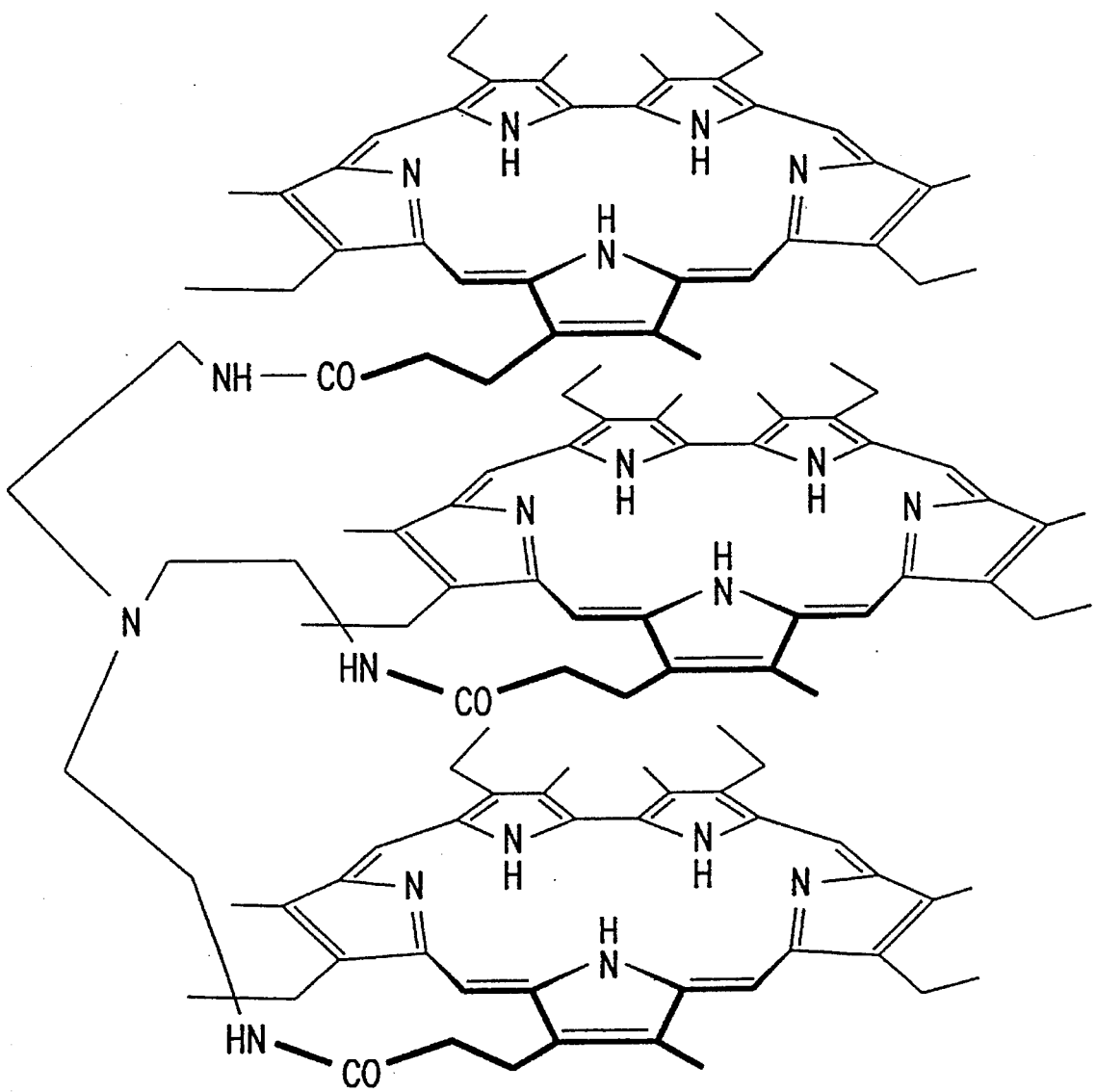
Figures 5, 5B, 6:
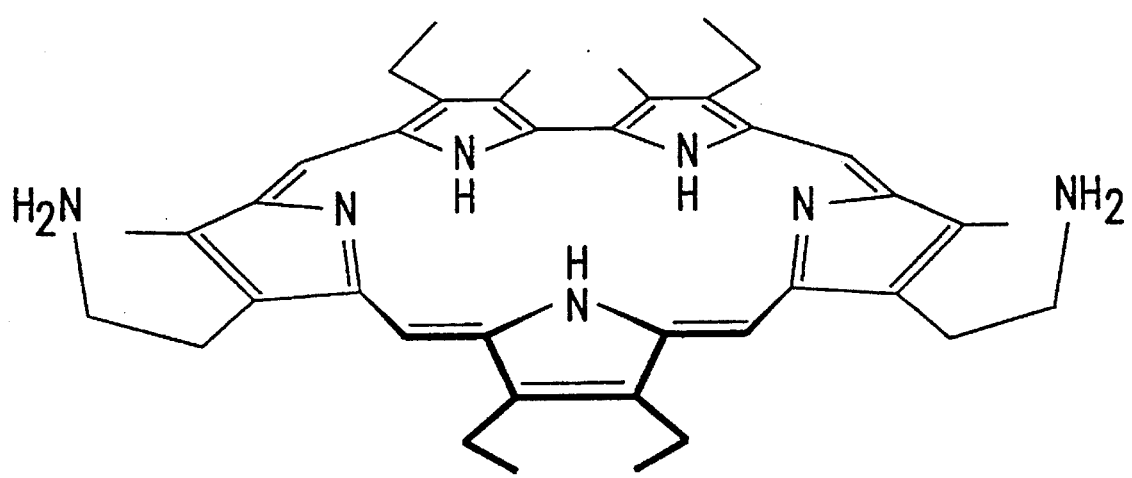
Figures 1, 5C:
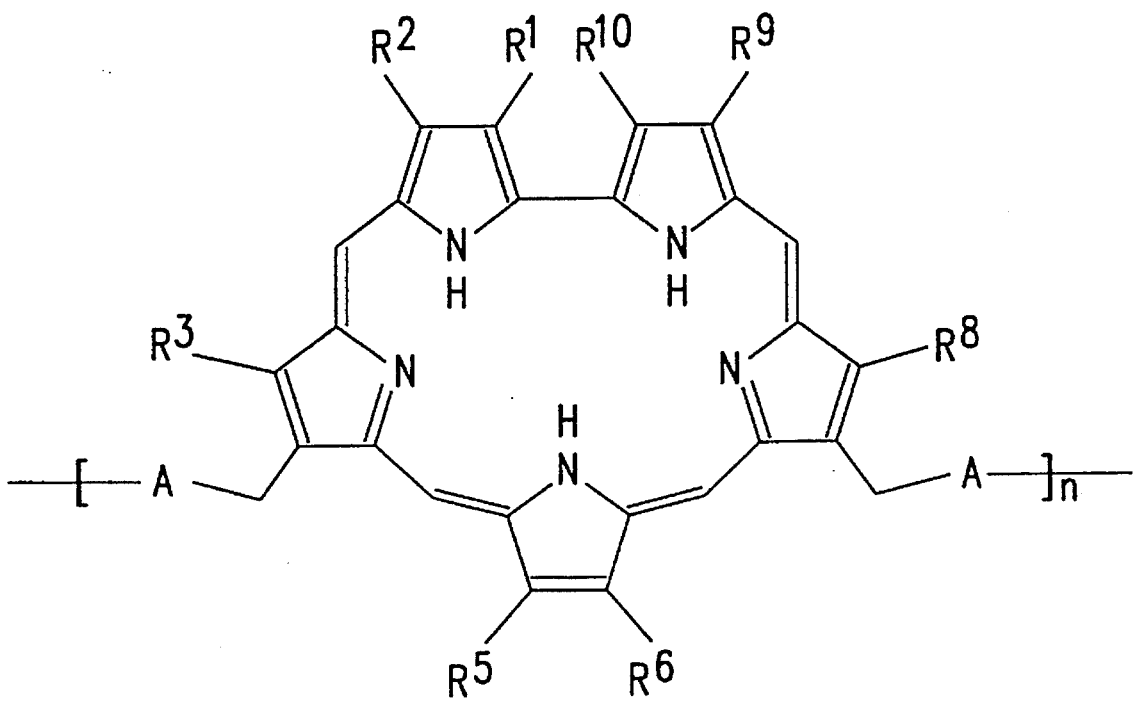
Figures 2I, 5C:
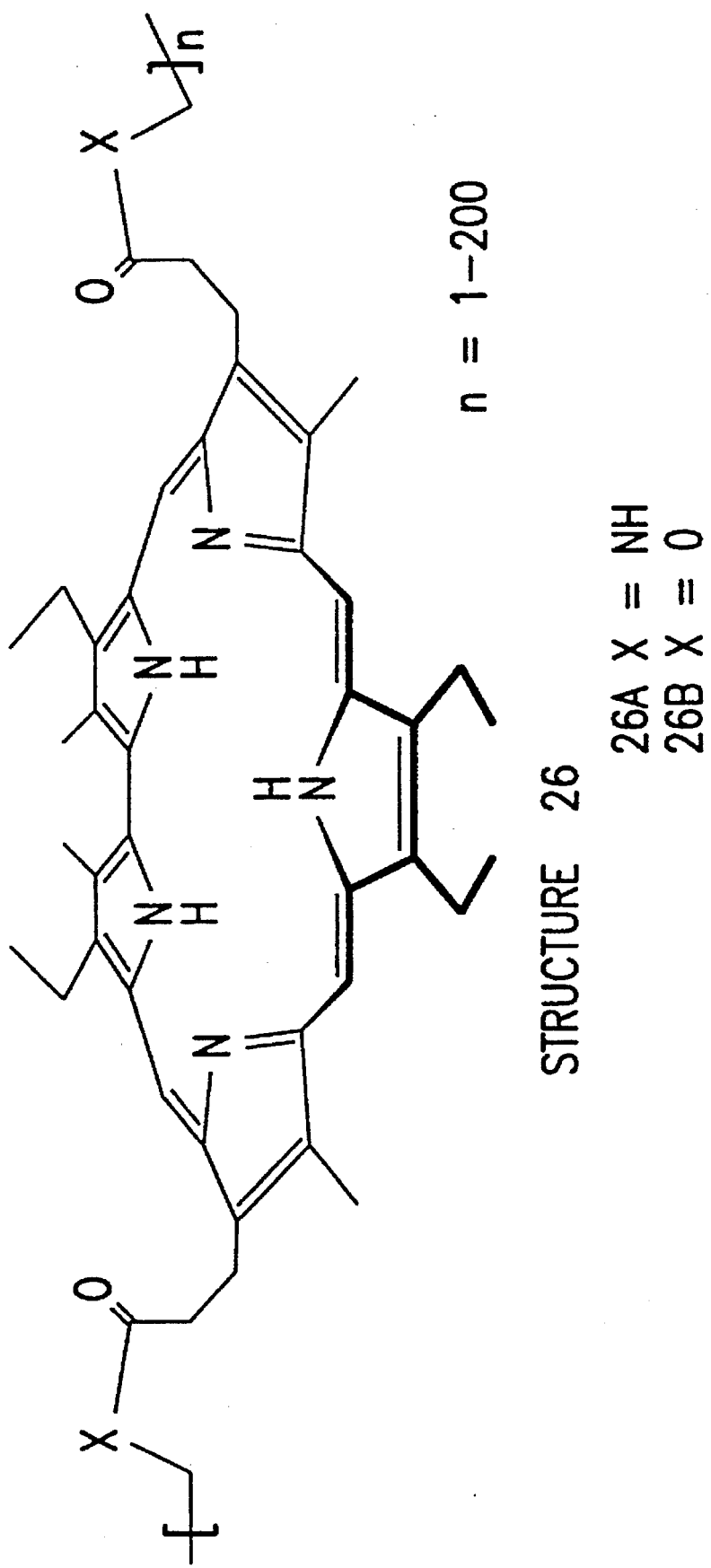
Figures 2I, 5C:
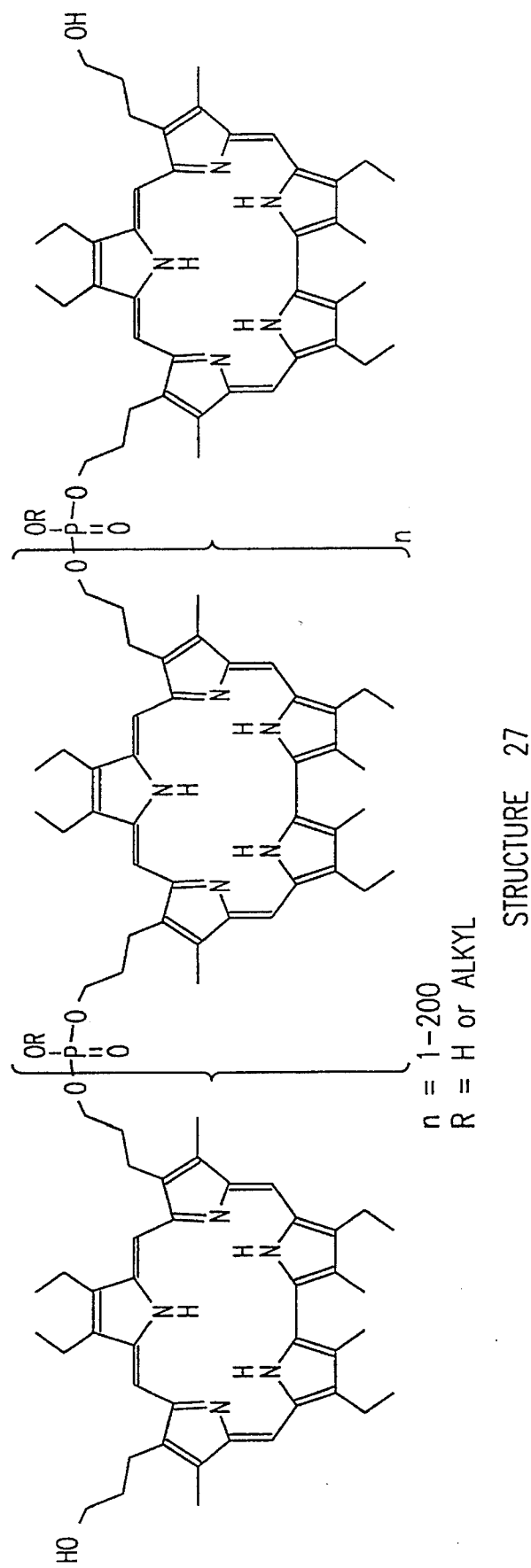

FIG. 5C-1 through 5C-2ii: Structure V represents the general structure for the polymeric sapphyrins of the present invention. Structure V is a more specific polymeric example of both structures III and IV, wherein further sapphyrin derivatives or other moieties, such as oligonucleotides or sapphyrin-oligonucleotides, have been added. In structure V, n may be from 1–100, or even from 1–200, $R^1$–$R^{10}$ and A may be H, alkyl, alkene, alkyne, halide, alkyl halide, hydroxyalkyl, glycol, polyglycol, thiol, alkyl thiol, aminoalkyl, carboxyalkyl, alkoxyalkyl, aryloxyalkyl, alkyloxycarbonyl, aryloxycarbonyl, aldehyde, ether, ketone, carboxylic acid, phosphate, phosphonate, sulfate, phosphate substituted alkyl, phosphonate substituted alkyl, or sulfate substituted alkyl.

Examples of sapphyrin polymers include, but are clearly not limited to, the sapphyrin structures 26A and 26B, where X=NH and X=O, respectively, and structure 27, where phosphate linkages are employed. Structure 25 represents a precursor sapphyrin derivative employed in oligomer synthesis.

Figures 1, 5D:
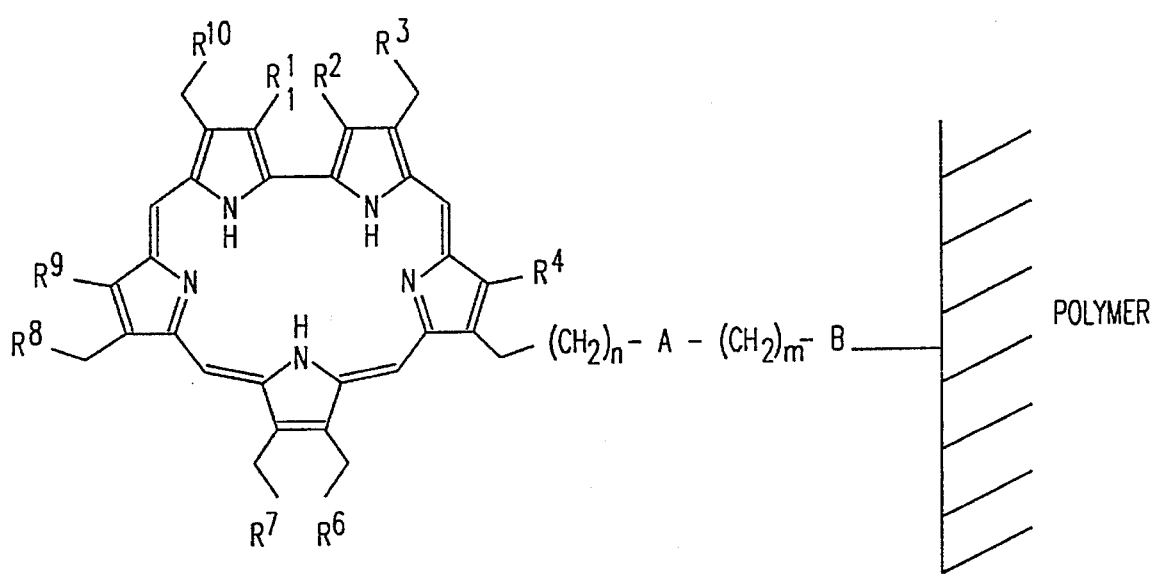
Figures 2, 5D:
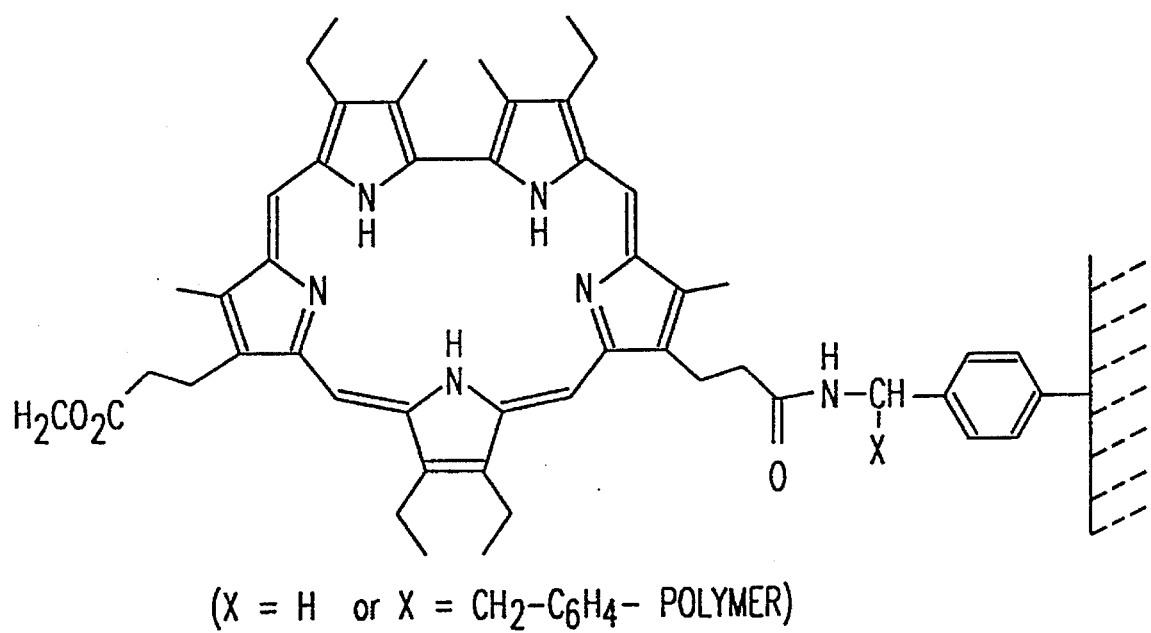
Figures 3, 5D:
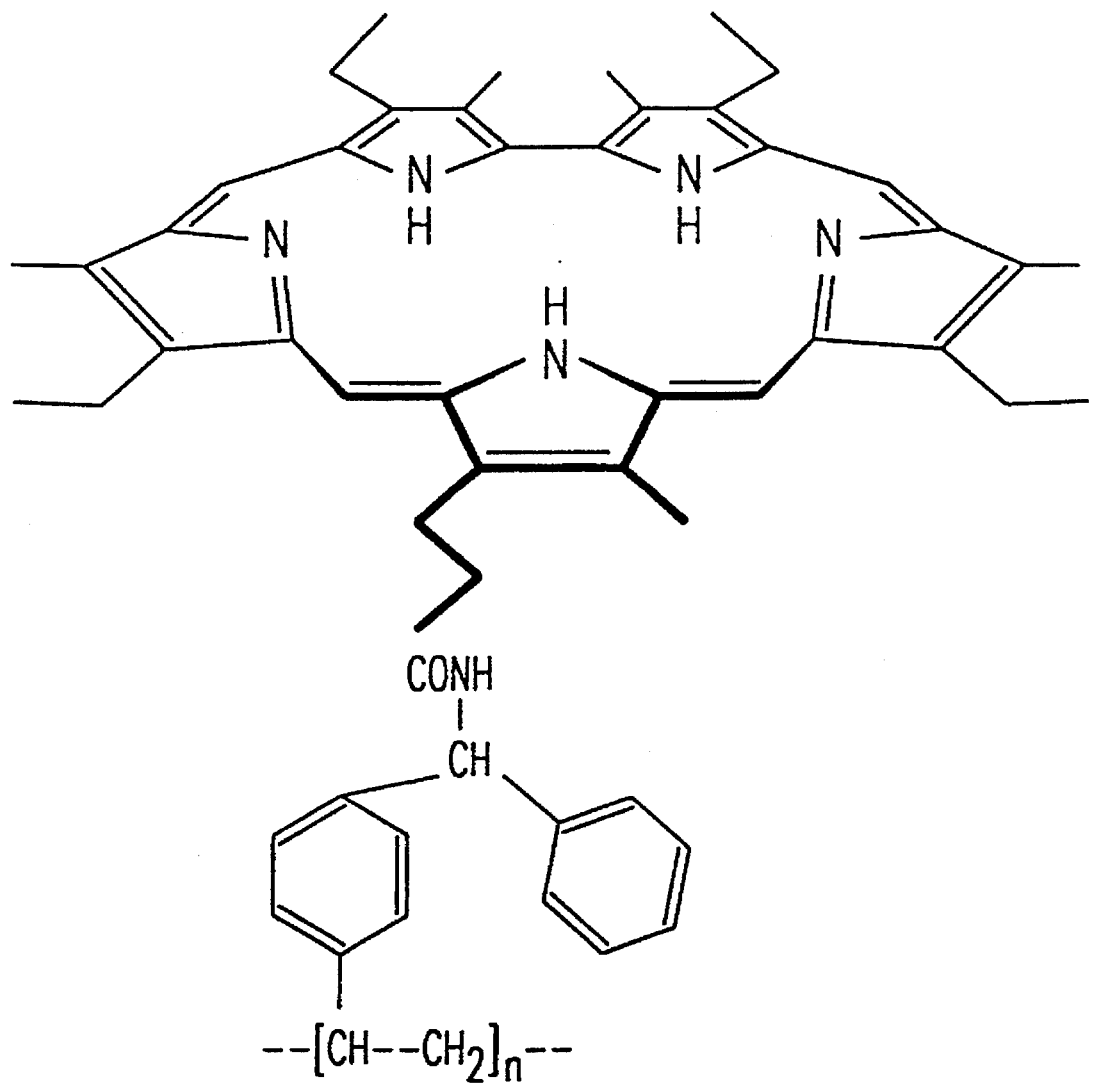
Figures 4, 5D:
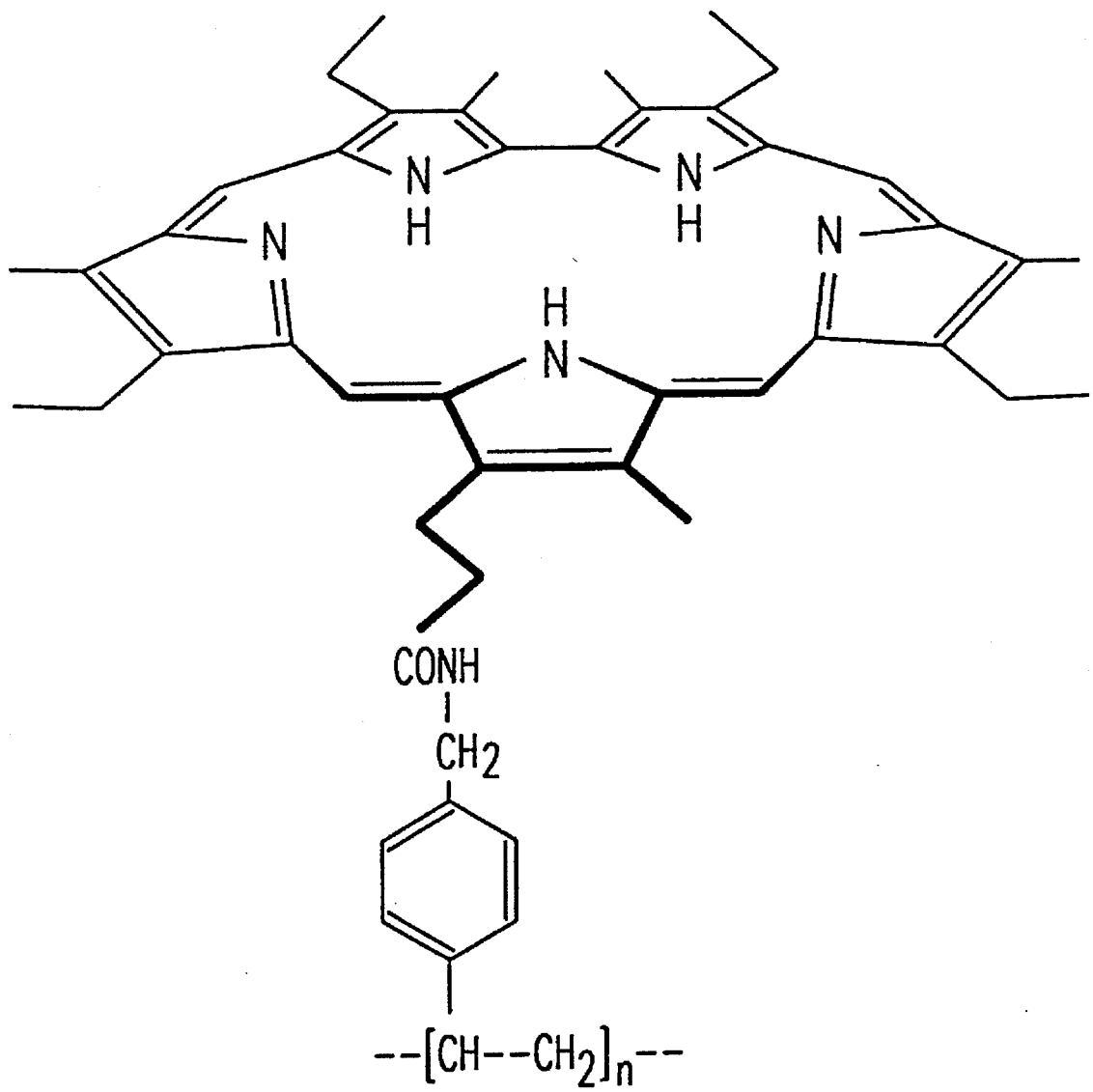
Figure 6:
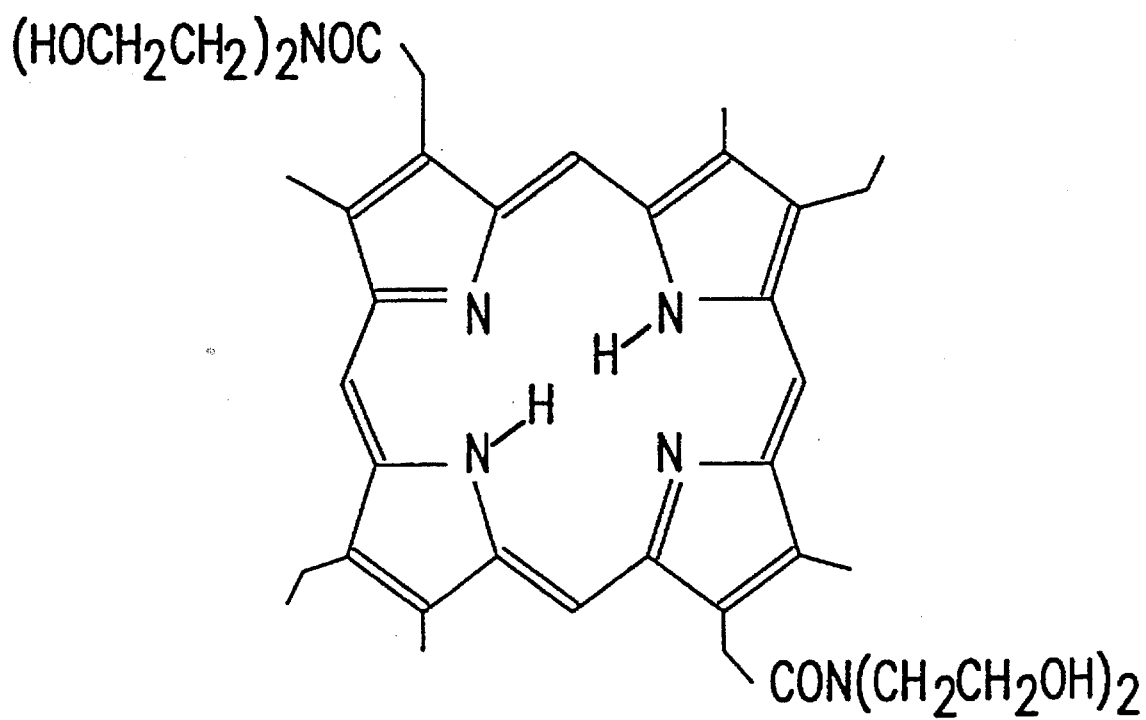

FIG. 5D-1 through 5D-4: Structure VI represents the general structure for the class of polymeric sapphyrins termed polymer supported sapphyrins. In structure VI, any of the groups $R^1$–$R^{10}$ may be derivatized to form a $(CH_2)_n$—A—$(CH_2)_m$—B structure, wherein A may be any of the groups listed above and B will include a polymer, polymeric matrix or solid support. B may also include any of the groups listed above for A, and preferably, will include an aryl, alkyl, silyl, siloxy, aminoaryl or amino group. The polymer, or solid support, of this structure may also be one of a variety of polymers, polymeric matrices, glasses or solids, such as, for example, silica, agarose, polyacrylamide, controlled pore glass, silica gel, polystyrene or sepharose.

Structure VII represents another general structure for a more defined class of polymer supported sapphyrins where certain functional groups such as $R^8$, have been defined Specific examples of polymer supported sapphyrins include, but are clearly not limited to, the sapphyrin structures 28 and 29.

FIG. 6. Structure 30. This molecule, a tetrahydroxy porphyrin derivative, was employed as a "control" molecule, or as a point of comparison, in the sapphyrin DNA binding studies described herein.

DETAILED DESCRIPTION OF THE PREFERRED EMBODIMENTS

Sapphyrins are large pyrrole-containing macrocyclic analogous to porphyrins (e.g. porphine, FIG. 1A, structure I,). The synthesis of various sapphyrins has been previously reported[2-6,11,12], see also, U.S. Pat. No. 5,159,065, incorporated herein by reference. Structural information is available for a limited number of sapphyrin analogues, for example[4,6,11]. The present invention concerns a variety of new sapphyrin-based systems, in which the sapphyrin molecule has been derivatized in a number of novel ways. In particular, this invention encompasses, but is not limited to, four broad new groups of sapphyrin-based molecular structures. These may be generally defined as: (I) water soluble sapphyrins; (II) sapphyrin-metal chelating conjugates; (III) sapphyrin-nucleobase conjugates; and (IV) oligomeric and polymeric sapphyrin derivatives, of which a sub-group is the polymer-supported sapphyrins.

Individually and collectively these new sapphyrin species overcome known deficiencies associated with extant sapphyrins. This is because all sapphyrins known at the time of this invention were exclusively monomeric in nature and insoluble in aqueous media at or near neutral pH. Thus, the sapphyrins known prior to the present invention were incapable of forming well-characterized, water soluble complexes with phosphorylated entities, including DNA, RNA, nucleotides, nucleotide analogues, and simple phosphate and phosphorate monoesters, at or near neutral pH.

In addition, all sapphyrins known at the time of this invention were recognized to be quite limited in terms of their substitution patterns, bearing either hydrogens, alkyl groups, or carboxy alkyl groups in the so-called β-positions. Thus, these systems could not and did not display any kind of binding selectivity as far as phosphate chelation was concerned; no specificity, for instance, for or against a particular nucleotide (i.e. guanosine-5'-monophosphate vs. cytosine 5'-monophosphate) was observed in such cases where such binding was inferred[5].

Furthermore, this same lack of substituent versatility meant that sapphyrin systems carrying potentially reactive side chains were completely unknown and this too was recognized as limiting the utility of those few sapphyrins known to be extant at the time of this invention. Thus, the inventors felt it worthwhile to prepare 1) water soluble sapphyrins, 2) sapphyrins bearing specific recognition units such as nucleobases, 3) sapphyrins bearing reactive sites, such as the metal chelating derivatives embodied in modified EDTA side chains, and 4) polymer supported sapphyrins and 5) oligomeric and polymeric sapphyrin systems, wherein the binding and recognition affects achieved in the monomeric sapphyrins might be expected to be greatly amplified.

Water soluble porphyrin and porphyrin-like derivatives, such as sapphyrins, are known to be of interest in biomedical applications including photodynamic therapy (PDT)[1]. The present inventors also recognized their potential for use in DNA recognition and modification. They reasoned that water soluble sapphyrin-based compounds without ionizable groups may be particularly advantageous for use in a number of ways, such as in PDT, cellular recognition and targeting and in the transport of biologically important molecules.

Anionic phosphorylated entities are ubiquitous in biology. They play a critical role in a variety of fundamental processes ranging from gene replication to energy transduction.[13] In addition, certain phosphate-bearing nucleotide analogues, such as, e.g., 9-(β-D-xylofuranosyl)guanine-5'-monophosphate (Xylo-GMP), are known to display antiviral activity in vitro.[9] However, Xylo-GMP, like a considerable number phosphorylated nucleotide analogues which exhibit antiviral activity in cell-free extracts, is inactive in vivo[9] due to its inability to cross lipophilic cell membranes[7,8].

The anti-herpetic agent, acyclovir (9-[(2-hydroxyethoxy)methyl]-9H-guanine), is active in vivo. Acyclovir can enter the cell only in its uncharged nucleoside-like form. Once in the cytoplasm, it is phosphorylated, first by a viral-encoded enzyme, thymidine kinase, and then by relatively nonspecific cellular enzymes to produce an active, ionic triphosphate nucleotide-like species. There it functions both as an inhibitor of the viral DNA polymerase and as a chain terminator for newly synthesized herpes simplex DNA.

The biological limitations of many other potential antiviral agents, including Xylo-G, arise from the fact that they are not phosphorylated once inside the cell and are therefore largely or completely inactive. If, however, the active monophosphorylated forms of these putative drugs could be transported into cells, it would be possible to fight viral infections with a large battery of otherwise inactive materials. If such specific into-cell transport were to be achieved, it would therefore greatly augment the treatment of such debilitating diseases as, for example, AIDS, herpes, hepatitis and measles. Given the fact that AIDS is currently a major national health problem of frightening proportions, and that something so nominally benign as measles still claims over 100,000 lives per year world-wide, treatment of these diseases would be particularly timely and worthwhile.

Not surprisingly, in recent years, increasing effort has been devoted to the problem of phosphate recognition and a number of phosphate-binding receptors are now known.[10] In spite of this, there are currently no artificial entities capable of effecting the selective through-membrane transport of mononucleotides and oligomeric polynucleotides at neutral or near-neutral pH, i.e., at a biological pH. A major aim of the inventors studies has been therefore to provide a means of transporting active mono- and polyphosphorylated forms of these and other agents into cells. This would allow a wide range of otherwise inactive compounds, such as antivirals, to be employed therapeutically, and would also create new possibilities for gene therapy.

In preliminary work concerning nucleoside transport, the present inventors employed triisopropylsilyl (TIPS) substituted (phosphate-free) nucleosides[14]. It was found that efficient and selective through-membrane transport of non-charged nucleoside analogues could be achieved by using the complementary TIPS derivatives as carriers[14]. Not surprisingly, however, these same TIPS derivatives proved completely ineffective as transport agents for the analogous phosphate-containing nucleotide derivatives. Thus, whilst confirming the viability of a base-pairing approach to selective nucleotide recognition, this work served to highlight further the need for an organic soluble, neutralizing, phosphate binding group.

The inventors reasoned that if sapphyrin-based systems were to be made effective as neutral-regime carriers, say, e.g. for GMP, it would require the construction of polytopic receptor systems in which a nucleobase recognition unit, in this case, a cytosine-like group, were "appended" directly onto the phosphate-chelating expanded porphyrin core. Naturally, they also contemplated the use of nucleobases recognition units other than cytosine for use in the specific binding and transport of the complementary nucleobases and nucleobase-containing compounds.

To synthesize multitopic receptors, the inventors developed strategies to address the following objectives: (i) the independent development of molecular recognition strategies for the complexation of two very different kinds of substrates (charged anionic and neutral nucleobase); (ii) their subsequent co-combination so as to provide receptors bearing both kinds of binding subunits; and (iii) various alternative methods of receptor oligomerization so as to provide oligomeric species bearing numerous combinations of multitopic receptors.

Pursuing these strategies led to the development of the sapphyrin-based ditopic receptor systems of the present invention, capable of recognizing both the anionic phosphate and the neutral portions of the nucleotide derivatives, such as the purine or pyrimidine moieties. Molecules of this type are, indeed, capable of the binding and transport of nucleotides and their derivatives. This theme was extended to the preparation of oligomeric, multitopic, receptors capable of recognizing multiple phosphate anions and nucleobase portions of nucleotide derivatives arranged in specific sequences.

The ditopic receptor systems are ideal vehicles for the intracellular transport of nucleotides and their derivatives, including anti-viral agents. The multitopic receptors, likewise, are contemplated to be of use in binding to oligonucleotides and specific sections of DNA or RNA and in transporting such nucleic acid segments into cells. The phosphate and nucleic acid base ("nucleobase") recognition, through-membrane transport and cell delivery properties of the present invention are thus applicable to the recognition and delivery of a large variety of monomeric and oligomeric species, including DNA, RNA and antisense constructs.

As outlined above, the present invention therefore encompasses, but is not limited to, the following four groups of novel sapphyrin-based molecular structures: (I) water soluble sapphyrins; (II) sapphyrin-metal chelating conjugates; (III) sapphyrin-nucleobase conjugates; and (IV) polymer supported sapphyrins and oligomeric and polymeric sapphyrin derivatives. The water soluble sapphyrins include sapphyrin hydroxyalkylamide and sugar derivatives. The sapphyrin-nucleobase conjugates include an extensive group of structures in which nucleobase-like recognition units are appended directly into the phosphate-chelating sapphyrin core. The last broad group comprises both polymer supported sapphyrins, and also oligomers and polymers of sapphyrin or sapphyrin derivatives and sapphyrin-nucleotide oligomers and polymers. The oligomeric linkage in such molecules may take place at various places in the sapphyrin or sapphyrin-nucleobase monomers.

In addition, it will be understood that the synthetic strategies developed by the inventors, wherein a functionalized sapphyrin is appended to a moiety of desirable chemical function, can be used to prepare an extremely wide variety of sapphyrin-containing conjugates. Sapphyrins may thus be conjugated to, not only metal chelating agents, sugars, nucleobases, and other sapphyrins, sapphyrin derivatives, or polysapphyrins, but also to a variety of other substances. These include, for example, phosphates, phosphonates, sulfates, sulfonates, amino acids, peptides, polypeptides, steroids, steroid derivatives, alkylating agents, and polymers glasses or solids, such as agarose, polyacrylamide, controlled pore glass, silica gel, polystyrene or sepharose. It is contemplated that one of skill in the art will be able to prepare sapphyrin conjugates including those listed above, without undue experimentation, given the extensive synthetic methodology disclosed throughout the present application

I. WATER SOLUBLE SAPPHYRIN DERIVATIVES

Water soluble porphyrin and porphyrin-like derivatives, especially sapphyrin derivatives, are of potential interest in a variety of applications ranging from photodynamic therapy (PDT) to DNA recognition and modification to cellular recognition and transport. The present inventors considered that the development of water soluble sapphyrin-based compounds without ionizable groups would likely be advantageous in a number of these applications.

In regard to PDT, water soluble sapphyrins may be used as photosensitization agents for the photodynamic inactivation of infectious agents having membranous envelopes. As such they may be employed in the photo-eradication of cell-free viruses from blood samples, such as, for example, the hepatitis viruses HBV and NANB, and especially HIV-1. In this process, sapphyrin localizes selectively at or near the morphologically characteristic viral envelope. Upon photoirradiation, it catalyzes the formation of highly reactive singlet oxygen which, in turn, destroys the essential membrane envelope, thus killing the virus and eliminating its infectivity, see U.S. Pat. No. 5,041,078, incorporated herein by reference.

The search for compounds for use in in vivo cellular transport and uptake, where diffusion across a membrane is involved, led the inventors to synthesize and characterize a range of novel water soluble sapphyrin derivatives. Generally speaking, the water soluble sapphyrin derivatives of this invention will include at least four OH groups, such as can be supplied by a variety of different polyhydroxy groups, or a single sugar residue. This broad class of water soluble sapphyrins can be further divided into water soluble polyhydroxysapphyrins and water soluble sapphyrin sugar derivatives. These groups include a variety of distinct molecules, such as, for example, the compounds represented by structures 1 and 3–6 (FIG. 2B), and substituted derivatives thereof.

Naturally, those of skill in the art will understand that a wide range of water soluble sapphyrins are encompassed by the present invention. Both a variety of polyhydroxysapphyrins and sapphyrin sugar derivatives may be synthesized according to the methodology disclosed herein. For example, any one, or more, of the many sugar and modified sugar units depicted in Table 1 may be linked to a sapphyrin core to create a water-soluble sapphyrin in accordance herewith.

A. Water Soluble Polyhydroxysapphyrins

These are water soluble sapphyrin derivatives based on two (poly)hydroxyalkylamido units attached to the macrocyclic periphery. Examples of compounds of this type include those represented by structures 1 and 3 (FIG. 2B). Although, naturally, it will be understood that a wide variety of different, and yet analogous, substituted derivatives may be prepared in accordance herewith. Polyhydroxysapphyrins may be prepared from an activated form of a sapphyrin acid (acid chloride, mixed anhydride, O-acylurea derivative, N-acylimidazole) and polyhydroxyamines.

B. Water Soluble Sapphyrin-Sugar Derivatives

The second general group of water soluble sapphyrin derivatives are the sapphyrin-sugar derivatives, where any one of a number of various sugar subunits are connected to the macrocycle periphery. Specific examples of this type of compound are represented by structures 4 & 6 (FIG. 2B). Again, in light of the present disclosure, those of skill in the art will be able to prepare a wide variety of distinct sapphyrin-sugar derivatives without undue experimentation. Examples of sugars and sugar-derivatives that may be employed in accordance herewith are listed in Table 1. The sugars employed may be either D or L forms and may also be either $\alpha$ or $\beta$ forms. The use of modified sugars is also envisioned, such as those including, for example, phosphate, methyl or amino groups. It is contemplated that preferred sugars for use in accordance herewith will include, for example, glucose, glucosamine, galactose, galactosamine and mannose.

TABLE 1

| Examples of Sugars and Sugar Derivatives | |
|---|---|
| Ribose | Fructose |
| Arabinose | Sorbose |
| Xylose | Tagatose |
| Lyxose | Fucose |
| Allose | |
| Altrose | Methylglucoside |
| Glucose | Glucose 6-phosphate |
| Mannose | |
| Gulose | N-Acetylgalactosamine |
| Idose | N-Acetylglucosamine |
| Galactose | Sialic Acid |
| Talose | |
| Ribulose | |
| Xylulose | |
| Psicose | |

For example, the efficiency of those compounds shown in FIGS. 4c and 6b for singlet oxygen generation has already been tested, when it was found to be 11% (in comparison with $ZnTPPS_4$). These water soluble sapphyrins 4c and 6b thus have apparent utility as a potential cellular targeting agent. As is generally known, glycoconjugates have important roles in the control of cell division and intercellular association. Changes in the biochemical and organizational structures occur during malignant transformation[15]. Therefore it may be therapeutically advantageous to alter or inhibit the biosynthesis of these tumor cell surface constituents. This might result in tumor cell death caused by the inhibition of the biosynthesis of vital membrane components. In this regard, D-glucosamine derivatives have been proven to be efficient inhibitors of tumor growth[16].

It is envisioned that differential tumor toxicity and specific organ targeting can be achieved with different sugar-sapphyrin derivatives. For instance, modified sugars such as e.g., Glc-NAc can be included within the image of substituents that can be appended to the sapphyrin core. All that would be needed is to start with an activated sapphyrin and 2-acetamido-2-deoxy- 3,4,6-tri-O-acetyl-$\beta$-D-glucopyranosylamine. The synthesis and use of this and other related systems are thus considered to fall within the scope of the present invention.

The synthesis of representative compounds 4 and 6 involve compounds that are connected via glycoside bonds and obtained starting from dihydroxysapphyrin and α-D-acetobromoglucose, as precursors, and using silver triflate in dichloromethane to effect coupling. The second set of systems is connected via amide bonds. These later materials are obtained starting from sapphyrin(bis)acid chloride and 1,3,4,6-tetra-O-acetyl-2-amino-2-deoxy-α-D-glucopyranose (tetraacetyl-D-glucosamine). In both series, after removing the protecting groups from the sugar moieties, the desired water soluble sapphyrin derivatives may be obtained.

It is contemplated that compounds such as those represented by structures 4 and 6 will have utility in both photophysical and biological embodiments. For example, it is envisioned that these new sapphyrins will have improved solubility and/or phosphate anion chelation properties, rendering them of use in protocols such as anti-viral transport and RNA/DNA recognition and binding.

II. SAPPHYRIN-CHELATING CONJUGATES

The second general group of novel monomeric sapphyrin derivatives of the present invention are the sapphyrin-metal chelating derivatives. Suitable chelating groups contemplated for use in such conjugates include, but are not limited to, EDTA, EGTA, DTPA, DOTA, ethylene diamine, bipyridine, 1,10-phenanthralene, crown ether, aza crown and catechols.

Figures 2, 3A:
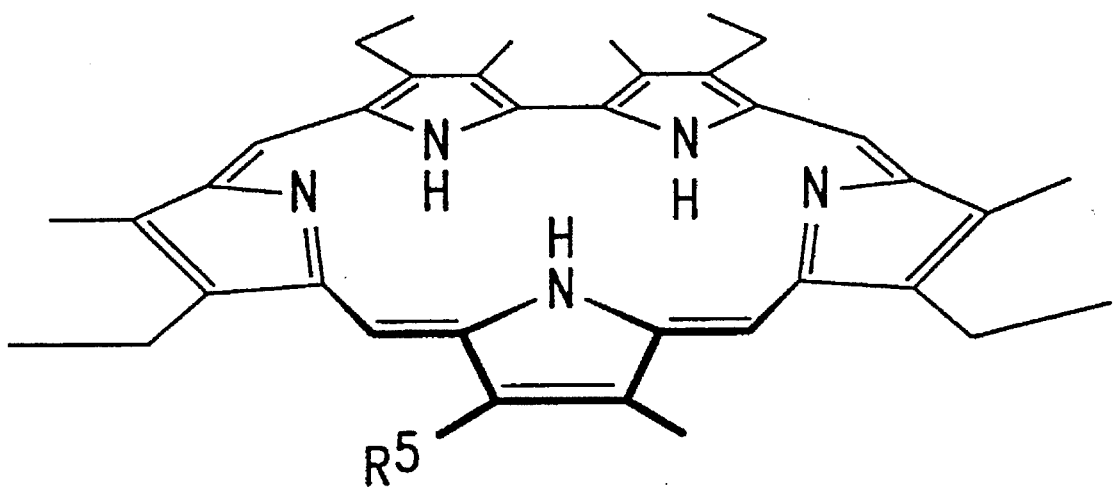
Figure 3B:
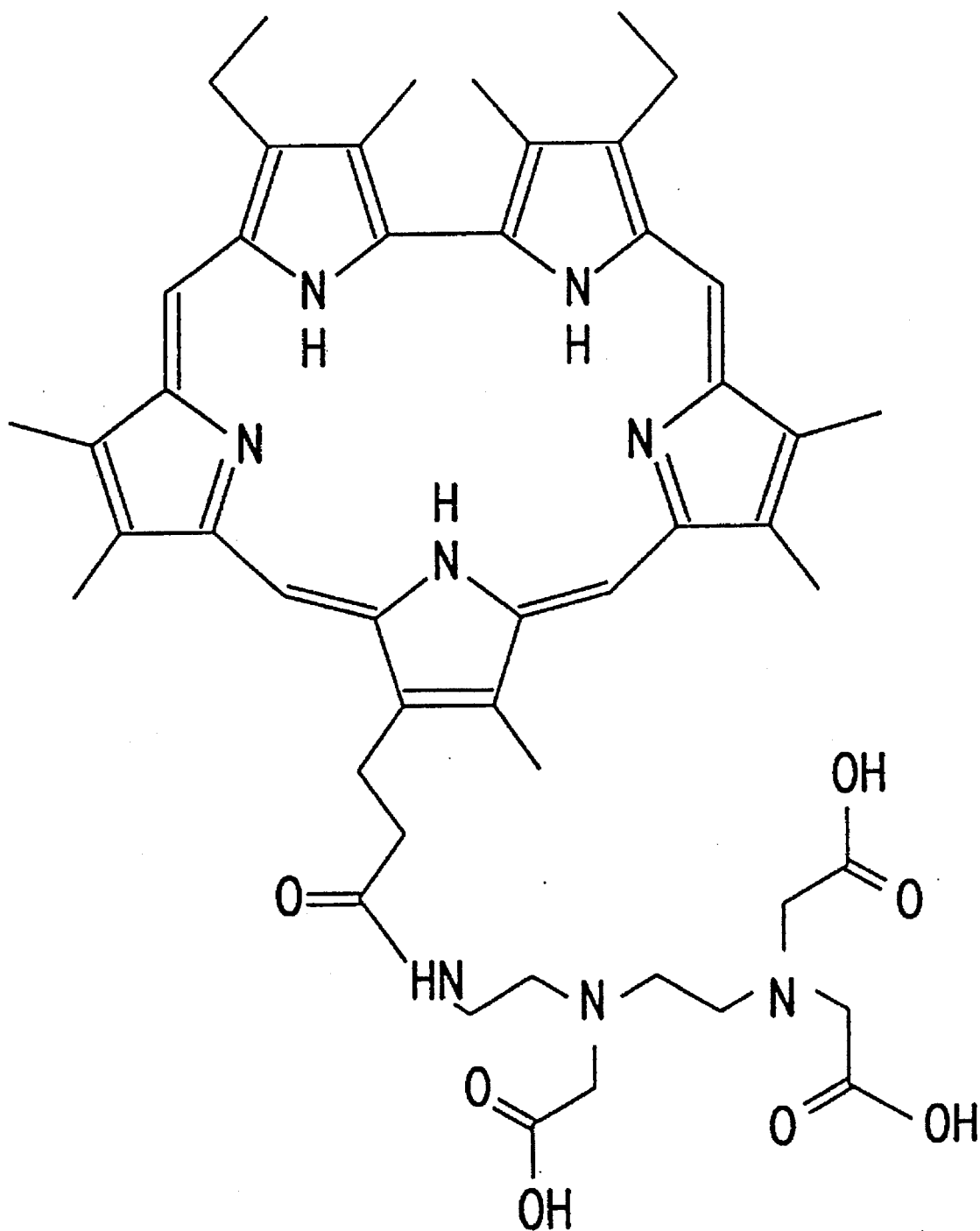

A specific example of this type of sapphyrin derivative is the sapphyrin-EDTA conjugate represented by structure 8 (FIG. 3B). The inventors have demonstrated that, in the presence of $Fe^{2+}$ and dithiothreitol, this molecule, in micromolar concentrations, can cleave DNA. Sapphyrin-EDTA conjugates will therefore be useful in effecting affinity cleavage of double stranded DNA. It is particularly contemplated that they will be of use in cleaving double stranded DNA of a defined sequence, or more importantly, perhaps will cleave double stranded DNA with a particular structural motif.

The sapphyrin-EDTA conjugate is believed to bind to DNA in a novel manner, based generally upon binding to the phosphate residues of the sugar-phosphate backbone. As such, it is contemplated that this sapphyrin conjugate will be capable of sensing conformational changes about the DNA back-bone. Sapphyrin-EDTA will thus be particularly useful as a structural probe of DNA, and the sapphyrin-metal chelating derivatives in general will be of use in a variety of photophysical embodiments.

III. SAPPHYRIN NUCLEOBASE DERIVATIVES

The inventors initially found that organic-solubilized, 2', 3', 5'-tris(triisopropylsilyl)-substituted nucleosides would enhance the through-$CH_2Cl_2$ transport of the corresponding Watson-Crick complementary phosphate-free nucleoside in a standard 3-phase Aq I—$CH_2Cl_2$—Aq II liquid membrane cell.[14] They also reported that the deproteinated form of sapphyrin, a pentapyrrolic "expanded porphyrin",[2,3,4a,6] acts as an efficient but non-selective carrier for nucleotide monophosphates at pH<4.[5] Rubyrin[17], and a large excess of C-Tips (ca. 100-fold) was also found capable of effecting the selective through-transport of GMP at neutral pH (C-Tips is 2',3',5'-tris(triisopropylsilyl)-cytosine.

However, sapphyrin, which remains monoprotonated in the ca. $3.5 \leq pH \leq 10$ [5,18] was itself found to be ineffective as a GMP carrier at pH 7, even in the presence of a large excess of C-Tips.[18] Thus, it was thought that if sapphyrin-based systems were to be made effective as neutral-regime carriers, it would require the construction of sapphyrin systems in which nucleotide recognition units are "appended" directly onto the phosphate-chelating expanded porphyrin core.

Precisely these types of sapphyrin derivatives have now been synthesized and form an important part of the present invention. These sapphyrin nucleobase conjugates are molecules which have been derivatized by the addition of one or more nucleobase compounds, i.e., one or more purines, pyrimidines, or derivatives thereof. Sapphyrin derivatives with one nucleobase per sapphyrin molecule may be referred to as ditopic receptors, whereas those with 2 nucleobases per molecules are termed tritopic receptors.

Sapphyrin mononucleobase derivatives may include any of the naturally-occurring purine or pyrimidine nucleobases, namely, cytosine, guanine, thymidine, adenine or uridine. Equally, they may include modified versions of any of these, such as the heterocyclic components of those nucleoside/nucleotide analogues listed in Table 2.

TABLE 2

| MODIFIED NUCLEOSIDE/NUCLEOTIDE ANALOGUE ANTI-METABOLITES |
|---|
| AraC |
| AraAMP |
| Azaribine |
| Azathioprine |
| Azauridine |
| AZT |
| Bromodeoxyuridine |
| Chlorodeoxyuridine |
| Cytarabine |
| Deoxyuridine |
| Dideoxyinosine DDI |
| Erythrohydroxynonyladenine |
| Floxuridine |
| Fluorouracil (5-FU) |
| Idoxuridine |
| LOMPD |
| Mercaptopurine |
| PFA |
| Thioguanine |
| Trifluoromethylde-oxyuridine |
| Xylo-GMP |

Also included within the invention are the sapphyrin mononucleobase derivatives including chemically modified nucleobase such as "protected" bases. Protecting groups are used to protect reactive groups, such as amino and carboxyl groups, from inappropriate chemical reactions. Sapphyrin-nucleobase conjugates with protected bases include, for example, conjugates wherein one or more base has a protecting group, such as 9-fluorenylmethylcarbonyl, benzyloxycarbonyl, 4-methoxyphenacyloxycarbonyl, t-butyloxycarbonyl, 1-adamantyloxycarbonyl, benzoyl, N-triphenylmethyl or N-di-(4-methoxyphenyl)phenylmethyl on the amino group of the nucleobase.

As clearly detailed in the description of the figures, any of the groups $R^1$–$R^{10}$ may be H, alkyl, alkene, alkyne, halide, alkyl halide, hydroxyalkyl, glycol, polyglycol, thiol, alkyl thiol, aminoalkyl, carboxyalkyl, alkoxyalkyl, aryloxyalkyl, alkyloxycarbonyl, aryloxycarbonyl, aldehyde, ether, ketone, carboxylic acid, phosphate, phosphonate, sulfate, phosphate substituted alkyl, phosphonate substituted alkyl, or sulfate substituted alkyl; with at least one of these R groups being: $(CH_2)_n$—A—$(CH_2)_m$—B, wherein A may include any of the groups listed above and B will be one or more nucleobases, nucleobase derivatives or protected nucleobases.

Conjugation of a nucleobase to a sapphyrin derivative to form a mononucleobase sapphyrin conjugate may be via any of the R groups $R^1$–$^{10}$. Conjugation of the two separate nucleobases to a sapphyrin derivative to form a dinucleobase sapphyrin conjugate may also be via any two of the R groups $R^1$–$^{10}$. However, it is contemplated that the creation of a symmetrical molecule, such as by substitution on $R^4$ and $R^7$, or $R^5$ and $R^6$, will generally be preferred.

Specific examples of sapphyrin mononucleobase derivatives are represented by structures 9–15 (FIG. 4A-2 through 4A-7). These include, but are clearly not limited to, the cytosine-containing sapphyrin derivative represented by structure 10; and the guanine-containing sapphyrin compounds 12, 14 & 15. The doubly substituted sapphyrin analogues, or tritopic sapphyrin receptors, of this invention may contain any combination of nucleobases. These sapphyrin derivatives may be homonucleobase conjugates, containing two of the same bases, or heteronucleobase constructs containing two distinct nucleobases in any combination. Thus, for example, in the nomenclature used herein, a sapphyrin nucleobase derivative with a single cytosine residue is represented by structure 10; a sapphyrin nucleobase derivative with two guanine residues is represented by structure 18, and a sapphyrin nucleobase derivative with one guanine residue and one cytosine residue is represented by structure 16.

These sapphyrin nucleobase monomers will act as selective carriers for the through-membrane transport of nucleotide monophosphates at biological, i.e. near-neutral pH. Thus, a sapphyrin nucleobase derivative bearing a cytosine residue will function in the binding and transport of GMP, and likewise, each nucleobase conjugates will be able to effect the transport of its complementary base, i.e., the base with which it naturally base-pairs. The nucleobase conjugates will be particularly useful for the transport of nucleotide derivatives, such as acyclovir monophosphate, Xylo-GMP and Ara-AMP, phosphonate derivatives and simple species such as the pyrophosphate derivatives PFA and COMDP, each of which function as antiviral agents.

For initial studies, ditopic and tritopic sapphyrin receptors bearing one and two cytosine molecules were first synthesized. The ditopic receptor is represented by structure 10 (FIG. 4A-3), and the tritopic receptor by structure 20 (FIG. 4B-5). These sapphyrin nucleobase derivatives were prepared by trifluoroacetic acid (TFA) induced detritylation of protected conjugates. The protected conjugates in question are those wherein the nucleobase derivative contains, instead of a single hydrogen, a $C(C_6H_5)_3$ group. These, in turn, were prepared by coupling 1-(2-aminoethyl)-4-[(triphenylmethyl)amino]-pyrimidin- 2-one[19] with the appropriate sapphyrin mono- or diacid chlorides.

The inventors have also prepared a variety of sapphyrin nucleobase conjugates by the condensation of sapphyrin mono and bis acids with conveniently modified nucleobases. Various spacers may be used for the connection, such as, for example, oligomethylene bridges with terminal amino, or hydroxy function, which allow formation of amide and ester bond for the connection of the sapphyrin and nucleobase units. This bridge may also be modified, e.g., by the reduction of the amide bond to give the amine function.[19] Satisfactory spectroscopic and analytic data have been obtained for all such new compounds. The present invention thus encompasses many possibilities for the connection of the same or different nucleobases to one sapphyrin macrocycle.

Transport studies, using a standard[20] Aq I—$CH_2Cl_2$—Aq II liquid membrane cell, were carried out using the sapphyrin cytosine conjugates represented by structures 10 and 20. It was found that both 10 and 20 were able to effect the selective through-membrane transport of GMP at, or near, neutral pH (Table 3). In all cases, compound 20 displayed a higher selectivity for GMP, by a factor of 8–100, relative to either AMP or CMP, than its congener 10.

These results clearly demonstrate that the transport of a normally organic-insoluble species, namely guanosine-5′-monophosphate (GMP), can be effected by preparing and using an appropriate sapphyrin-nucleobase conjugate. A similarly designed sapphyrin receptor approach may be used to achieve the into-cell in vivo delivery of other nucleotides and nucleotide derivatives, such as, for example, Xylo-GMP and other antiviral nucleotide-based drugs.

IV. OLIGOMERIC AND POLYMERIC SAPPHYRIN DERIVATIVES

Further groups of novel sapphyrin-based compounds embodied by the present invention are the sapphyrin oligomers and polymers. These include relatively low-number conjugates, such as dimers and trimers, and also larger oligomers or polymers. The oligomers will generally include between about 4 and about 8 residues, or even up to 12 residues, whereas the polymers may generally comprise from about 13 to about 100 residues, or even up to about 200.

The monomeric units employed in the synthesis of sapphyrin-sapphyrin conjugates may be known sapphyrin molecules, such as those described in U.S. Pat. No. 5,159,065, incorporated herein by reference. Equally, any of the novel sapphyrin derivatives disclosed herein may be employed, in any combination, to create further novel sapphyrin dimers, trimers, oligomers or polymers. Encompassed within the terms oligomers or polymers are those sapphyrin conjugates synthesized by the controlled addition of particular monomeric units and those produced by more uncontrolled polymerization methods.

Due to the unique mode of DNA interaction, sapphyrin polymeric molecule will possess an unrivaled ability to act as a general DNA binding platform. This has the distinct advantage that it can be modified so as to adjust both target cell specificity and degree of interaction with the DNA. For sapphyrins and sapphyrin polymers, the basic site of interaction with the DNA involves the interior of the sapphyrin macrocycle, so that the exterior positions $R_1$–$R_{10}$ can be substantially modified without significantly disrupting the DNA binding interaction. These exterior positions can be used to systematically adjust features such as solubility, membrane permeability and cell selectivity. Furthermore, groups designed to modulate interaction with DNA can be attached to the exterior of the sapphyrin polymers including alkylating functions (bromoacetamido groups, epoxides etc.) to provide covalent attachment to DNA or ene-diyne moieties to allow for double stranded cleavage.

A further and important advantage of the sapphyrin system is that the simple DNA binding motif has been extended to several multimeric structures, in which multiple sapphyrins covalently linked together will be able to bind simultaneously and thus strengthen the entire interaction. This feature will allow a modular approach in which the appropriate number (2–10) of sapphyrin molecules is attached in a single molecule, perhaps with different sapphyrin units containing sapphyrin derivatives with different groups attached that control such important properties such as solubility, target cell specificity and DNA modification ability.

A. Sapphyrin Oligomers

Specific examples of sapphyrin oligomers include, but are not limited to, those compounds represented by structures 21–24 (FIG. 5B-2 through 5B-5). Sapphyrin oligomers were been prepared by the condensation of sapphyrin mono and bis acids with amino groups as spacers units. As di- and tri-amino spacers, ethylenediamine, 1,3-diaminopropane, 1,3- and 1,4-phenylenediamine, diaminonaphtalenes and anthracenes, for example, have used in the synthetic approach. Sapphyrin trimers were built in one step reaction, in which 3 molar equivalents of sapphyrin mono acid were combined with a trisamino component, e.g. tris(aminoethyl) amine, in very high yield.

For the coupling reaction, a variety of different methods have been used. These include, for example, acid chloride, O-acylurea, mixed anhydride and N-acylimidazole, which were found to be particularly successful. The synthetic methodology employed was essentially the same as that developed to prepare sapphyrin-nucleobase conjugates. It is important to emphasize that the synthesis of both the sapphyrin nucleobase conjugates and the sapphyrin oligomers and polymers may be readily performed using a standard automated oligonucleotide synthesizer.

The present inventors have prepared mono- di- and tri-sapphyrins and have proven them to be very efficient recognition species for nucleotides, monophospates, diphosphates and triphosphates. The formation of noncovalently bonded complexes between sapphyrin-like oligomers and a nucleotide allows the transport of nucleotide mono, di and triphosphates across cell membranes to occur at physiological pH. This will likely be of direct use in the transport of antiviral triphosphates to mammalian cells, especially for the treatment of AIDS.

As discussed above, any of the novel sapphyrins of the present invention may be employed, in any combination, in the synthesis of novel sapphyrin oligomers or polymers. The synthetic approach developed is equally suitable to the use of one or more novel sapphyrin derivatives as starting materials as it is to the use of known sapphyrins. Importantly, methods are disclosed herein for the generation of covalently bonded sapphyrin-nucleotide complexes. Importantly, the sapphyrin-sapphyrin nucleobase and sapphyrin-DNA linkage chemistry of the present invention is compatible with automated oligonucleotide synthesis, and phosphoramidate chemistry.

The present invention encompasses two categories of sapphyrin polymers; these may be described generally as polymeric sapphyrins and polymer supported sapphyrins. The polymeric sapphyrins may be employed in a variety of different embodiments, for example, relating to oligonucleotide binding and transport, as will be discussed more fully below. The polymer supported sapphyrin group includes resin-synthesized sapphyrins. These sapphyrin polymers may ultimately be cleaved, resulting in the generation of a free polymer. However, following resin-bound synthesis, the polymers may be maintained covalently bound to the parent resin, thus opening further possibilities for their use.

Sapphyrin polymers which are maintained bound to the parent resin may be advantageously employed as a "column material" for use in chromatography, for example, in the separation of nucleotides or in photoactivation. With regards to the latter, it is to be appreciated that polymer-supported sapphyrins could prove particularly advantageous for the in vitro inactivation of viruses and other blood borne pathogens: the fact that no sapphyrin would be left in the blood (or other substance) being purged would militate against any toxicity problems.

B. Polymeric Sapphyrins

One class of sapphyrin polymers contemplated by the present invention are those compounds resulting from the polymerization of monomeric units, by various types of processes other than those using a resin. For example, radical polymerization of olefin substituted sapphyrin may be employed to give a polyethylene type of polymer. Alternatively, polycondensation of sapphyrin bis acid with sapphyrin diamine could be used to give a polyamide type of polymer, or polycondensation of sapphyrin bis acid with sapphyrin bis alcohol may be employed resulting in a polyester type of polymer. In all of these cases, sapphyrin-based polymers may be prepared both with and without covalently bonded nucleobases. Examples of the latter are 26A and 26B.

C. Polymer Supported Sapphyrin

One class of sapphyrin polymers are those based on the covalent connection of sapphyrin derivatives to different types of polymeric resins. To achieve this, amide, ester, ether and amino bonds have been used. The great advantage of this procedure is that different numbers of sapphyrin molecules may be introduced per polymer unit simply by varying the molar ratio of sapphyrin derivative to the number of the groups bonded on polymer surface, illustrated both schematically, and with specific examples, throughout FIG. 5D-1 through 5D-4.

Nucleobase-sapphyrin conjugates of the present invention which posses another functional group, namely a carboxy group, could also be used advantageously for attaching sapphyrins to polymeric matrices resulting in novel polymer-bonded sapphyrins with unique properties, for example, for use in the specific binding of oligonucleotides and nucleic acids. Sapphyrin polymers contemplated within this group include those where the sapphyrin units are bonded to natural occurring polymers, for example, to polysaccharides or nucleic acids, via sugar or nucleobase units.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. For example, other macrocyclic, positively-charged entities can be envisioned as binding to phosphate-containing species such as nucleotides, oligonucleotides and DNA by means of the same or similar oriented electrostatic interactions described herein.

EXAMPLE 1

SYNTHESIS OF POLYHYDROXYSAPPHYRINS

A. Preparation of 3,12,13,22-tetraethyl-8,17-bis[di(hydroxyethyl)aminocarbonylethyl]-2,7,18,23-tetramethylsapphryin, structure 1

Sapphyrin bis acid structure $2a$ (66 mg, 0.1 mmol) was dissolved/suspended in dry dichloromethane (30 ml) and 0.5 ml oxalylchloride and 1 drop of DMF was added. The reaction mixture was stirred at room temperature for 3 hours, then evaporated to dryness. Sapphyrin bis acid chloride was dissolved in dry dichloromethane (20 ml) and slowly added under argon to the solution of diethanoamine (52.5 mg, 0.5 mmol) in dry dichloromethane (30 ml), which contained also 5 mg of 4-dimethylaminopyridine and 0.2 ml pyridine. The reaction mixture was stirred at room temperature for 24 hours and then washed with brine, which contained 5% hydrochloric acid. The water phase was washed 3 times with dichloromethane containing 20% of methanol. The combined organic extracts were dried over sodium sulfate and evaporated. Crystalization from ethanol-hexane (1:3) gave 75 mg (86.9%) of product 1.

$^1$H NMR (300 MHz, CDCl$_3$) δ:−5.13 (2H, s, NH), −4.95

(1H, s, NH), −4.78 (2H, s, NH), 2.18 (4H, t, $CH_2CH_3$), 2.20 (4H, t, $CH_2CH_3$) 2.24 (4H, t, $CH_2CH_3$), 2.88 (8H, t, $NCH_2CH_2OH$), 2.94 (8H, t, $NCH_2CH_2OH$), 3.56 (4H, t, $CH_2CH_2CON$), 4.07 (6H, s, $CH_3$), 4.25 (6H, s, $CH_3$), 4.49 (2H, q, $CH_2CH_3$), 4.52 (2H, q, $CH_2CH_3$), 4.79 (2H, q, $CH_2CH_3$), 5.15 (2H, q, $CH_2CH_3$), 5.30 (4H, t, $CH_2CH_2CON$), 6.05 (4H, br s, OH), 11.66 (2H, s, meso-H), 11.78 (2H, s, meso-H). FAB MS m/e (rel. intensity) 863 (98, $[MH]^+$), 864 (78, $[MH_2]^+$), 862 (56, $[M]^+$). HRMS Calcd for $C_{50}H_{68}N_7O_5$: 862.520676. Found 862.523102 UV/VIS ($H_2O$): $\lambda_{max}$ 410.5, 621.0, 672.0.

B. Preparation of 3,12,13,22-tetraethyl-8,17-bis{[tris(hydroxymethyl)methylamino]-carbonylethyl}-2,7,18,23-tetramethylsapphryin, structure 3.

Sapphyrin bis acid structure 2a (66 mg, 0.1 mmol) was dissolved in dry tetrahydrofuran (20 ml) and 1,1'-carbonyldiimidazole (33 mg, 0.2 mmol) was added and solution was stirred at room temperature for 1 hour. A solution of tris(hydroxymethyl)aminomethane (24.2 mg, 0.2 mmol) in 3 ml of water was added. The reaction mixture was stirred for 12 hours then imidazole was filtered off, the solvent was evaporated in vacuo and the product crystalized from mixture methanoldichloromethane (1:10), the yield of product 3 was 73 mg (81.5%).

FAB MS m/e (rel. intensity) 896 (100,$[M]^+$), 897 (60, $[MH]^+$). HRMS: Calcd. $C_{50}H_{69}N_7O_8$ 895.52072. Found 895.52099. UV/VIS ($H_2O$): $\lambda_{max}$ 412,622,673.

EXAMPLE 2

SYNTHESIS OF SAPPHYRIN DIGLYCOSIDES

Sapphyrin mono and diglycosides were prepared by the glycosylation of sapphyrin alcohols with α-D-acetobromoglucose and α-D-acetobromogalactose with a silver catalyst. The most advantageous catalyst was found to be silver triflate, although silver tetrafluoroborate and silver carbonate also gave very good results. With polyalcohols it is possible to determine the conversion to glycosides by the molar ratio alcohol-halogenose/silver catalyst. The inventors were able to introduce 1 or 2 sugar units as a function of the molar ratio of hydroxy groups/halogenose/silver catalyst.

A. Preparation of 8,17-di(tetraacetate-α, β-D-glucopyranoxypropyl)-3,12,22-tetraethyl-2,7,18,23-tetramethylsapphyrin, structure 4A.

3,12,13,22-Tetraethyl-2,7,18,23-tetramethyl-8,17-di(hydroxypropyl) sapphyrin structure 5 (132 mg, 0.2 mmol) was dried with silver triflate (0.2569 g, 1 mmol) and barium carbonate (0.5 g) for 2 hours at 20° C./1.32 mm Hg in apparatus equipped with septum. The apparatus was flushed with argon (2×) and dry dichloromethane (50 ml) was added through the septum. After dissolution, the mixture was cooled to −45° C. and solution of α-D-glucopyranosylbromide tetraacetate (0.411 g 1 mmol) in dichloromethane (20 ml) was gradually added through septum under stirring. The reaction mixture was stirred at −45° C. for 1 hour, then allowed to warm to room temperature with exclusion if light and stirred for 8 hours. The reaction mixture was diluted with 50 ml of dichloromethane, filtered with celite, the filtrate was washed with saturated solution of sodium hydrogencarbonate and water, dried over sodium sulfate and solvent was evaporated. Pure product was obtained by column chromatography on silica gel with dichloromethane with 4% of methanol as a eluent. The yield of product 4a was 250 mg (94.7%).

$^1$H NMR spectrum (300 MHz, $CDCl_3$): δ−6.21−6.07, −5.81, −5.75, 2.03, 2.05, 2.11, 2.13, 2.16, 2.28, 2.31, 3.09, 4.11, 4.17, 4.24, 4.33, 4.51, 4.53, 4.72, 4.74, 5.29, 11.59, 11.66. FAB MS, m/e (rel. intensity): 1321 (90, $[MH]^+$), 1322 (56, $[MH_2]^+$), 1320 (45, $[M]^+$). HRMS Calcd. for $C_{70}H_{89}N_5O_{20}$ 1319.6100. Found 1320.617916 ($[MH]^+$).

The same experimental procedure was used for the preparation of tetraacetylgalactose and tetraacetylmannose substituted sapphyrins. In these cases, the sugar unit was varied using the same protecting group.

B. Preparation of 8,17-di(tetrabenzoate-α,β-D-glucopyranoxypropyl)-3,12,13,22-tetraethyl-2,7,18,23-tetramethylsapphyrin, structure 4B.

The same procedure as for tetraacetylderivative with α-D-glucopyranosylbromide tetrabenzoate (0.660 g, 1 mmol) gave product 4b in 97.6% yield.

FAB MS m/e (rel. intensity):1817 (95, $[MH]^+$), 1818 (67, $[MH_2]^+$), 1816 (62, $[M]^+$). HRMS Calcd. for $C_{110}H_{105}N_5O_{20}$ 1815.7346. Found 1816.743117 ($[MH]^+$).

C. Preparation of 8,17-di(α,β-D-glucopyranoxypropyl)-3,12,13,22-tetraethyl-2,7,18,23-tetramethylsapphyrin, structure 4c.

The product was prepared from protected derivatives (acetyl, benzoyl) by splitting of protecting group in methanol with a catalytic amount of sodium methoxide, or potassium hydroxide, or potassium cyanide. Pure product was obtained by crystalization, or reverse phase chromatography ($C_{18}$-modified silicagel) with methanol as a eluent. The yield of product 4c was 67%.

FAB MS m/e (rel. intensity):986 (70, $[M]^+$), 987 (56, $[MH]^+$). HRMS Calcd. for $C_{54}H_{75}N_5O_{12}$ 985.54108. Found 985.5417. Elemental analysis: calc. 65.77% C, 7.67% H, 7.10% N; found 65.65% C, 7.69%H, 7.04% N. UV/VIS ($H_2O$): $\lambda_{max}$ 416,597.5, 642,712; (MeOH): $\lambda_{max}$ 445.

EXAMPLE 3

SYNTHESIS OF SAPPHYRIN BIS(GLYCOSAMIDES)

Sapphyrin bis(glycosamides) were prepared by condensation of an activated form of the above-described sapphyrin acid (acid chloride, mixed anhydride, O-acylurea, N-acylimidazole derivative) with free, or O-acetylated glycoamines (2-amino-2-deoxy-glucopyranose, mannopyranose, galactopyranose).

A. Preparation of 3,12,13,22-Tetraethyl-8,17-bis[1,3,4,6-tetra-O-acetyl- 2-amino-2-deoxy-α,β-D-glucopyranose)-carbonylethyl]2,7,18,23-tetramethylsapphyrin, structure 6A Sapphyrin bis acid structure 2a (69 mg, 0.1 mmol) was converted to bis acid chloride as previously described. Bis acid chloride was dissolved in dry dichloromethane under argon and slowly added to the solution of 1,3,4,6-tetra-O-acetyl-2-amino-2-desoxy-α-D-glucopyranose (0.1736, 0.5 mmol) in dichloromethane, which also contained 10 mg of 4-dimethylaminopyridine and 0.5 ml of dry pyridine at room temperature. The reaction mixture was stirred for 14 hours, then washed with water, the organic layer was evaporated and the product obtained by column chromatography on silica gel with dichloromethane containing 2–10% methanol as an eluent. The yield of product 6a was 114.6 mg (85.0%).

$^1$H NMR spectrum (300 MHz, $CDCl_3$): δ=−4.91, −4.59, 1.94, 2.06, 2.12, 2.27, 3.41, 3.689, 3.84, 3.91, 3.93, 4.05, 4.12, 4.22, 4.54, 4.63, 4.72, 5.04, 5.19, 5.22, 11.59, 11.69.

FAB MS, m/e (rel. intensity):1347 (96, $[M]^+$), 1348 (84, $[MH]^+$). HRMS: Calcd. $C_{70}H_{89}N_7O_{20}$ 1347.61428. Found 1347.61624.

B. Preparation of 3,12,13,22-Tetraethyl-8,17-bis[(2-amino-2-deoxy-α,β-D-glucopyranose)-carbonylethyl]-2,7,18,23- tetramethylsapphyrin, structure 6b.

The above-described acetylated sapphyrin derivative 6a (13.4 mg, 0.01 mmol) was dissolved in methanol (10 ml) and a solution of 3 mg KOH in methanol was added. The reaction mixture was stirred for 4 hours and then the pH adjusted to 6 by adding hydrochloric acid. After evaporating to dryness, the product was crystallized from methanol-dichloromethane (1:1), or obtained by reverse phase chromatography with methanol as eluent. The yield of product 6b was 10.38 mg (88.0%).

FAB MS, m/e (rel. intensity): 1012 (76, [MH]+), 1011 (54, [M]+). UV/VIS ($H_2O$): $\lambda_{max}$ 413,621,671.

Deacetylation could also be achieved under basic conditions by using, e.g., $NH_3$ in methanol, sodium methoxide in methanol, DABCO in methanol, or KCN in methanol, each with good yields.

EXAMPLE 4

SYNTHESIS OF SAPPHYRIN-EDTA CONJUGATE (STRUCTURE 8)

One example of the sapphyrin-metal chelating conjugates of the present invention is sapphyrin-EDTA. To a solution of diethylenetriamine (22.0 ml, 210 mmol) in 200 ml of dry dichloromethane at 0° C., was added triphenylmethylchoride (1.8 g, 6.5 mmol) and the solution was warmed to room temperature with stirring overnight. The organic layer was washed 1M NaOH (200 ml×3), dried with $Na_2SO_4$, and the solvent was removed by rotary evaporation. Purification on silica gel using methanol/dichloromethane yielded 2.1 g (94%) of a viscous oil that gave a positive test using ninhydrin.

$^1$H NMR δ ($CD_2Cl_2$) 2.27 (2H, t, $\phi_3CNHCH_2CH_2$), 2.55 (2H, t, $\phi_3CNHCH_2CH_2$), 2.70 (4H, m, $RNHCH_2CH_2NH_2$), 7.23–7.65 (15H, m, aromatic-H's), $^{13}$CNMR δ ($CDCl_3$) 41.5, 43.1, 49.9, 42.1, 70.7, 126.1, 127.7, 128.4, 146.1; MS FAB, [MH]+:m/z 346; HRMS, [MH]+: 346.2278 (calcd for $C_{23}H_{28}N_3$:346.2283).

Tert-butyl bromoacetate (1.3 ml, 8.5 mmol), tritylated diethylenetriamine (4, 0.89 g, 2.6 mmol), $K_2CO_3$ (1.18 g, 8.5 mmol), and $Cs_2CO_3$ (1.69 g, 5.2 mmol) in 15 ml of acetonitrile were stirred at 0° C. overnight. The inorganic salts were removed by vacuum filtration, and the solvent was removed by rotary evaporation. Purification on silica gel using dichloromethane/hexanes yielded 1.2 g (68%) of a light yellow oil:

$^1$H NMR δ ($CD_2Cl_2$) 1.41 (9H, s, $\phi_3CNRCH_2CO_2C(CH_3)_3$), 1.44 (18H, s, $N(CH_2CO_2C(CH_3)_3)_2$) 2.21 (2H, t, $\phi_3CNRCH_2$), 2.62 (2H, t, $\phi_3CNRCH_2CH_2$), 2.72 (4H, m, $NRCH_2CH_2NR_2$), 3.11 (2H, s, $CH_2CH_2NRCH_2CO_2$t-butyl) , 3.36 (4H, s, $N(CH_2CO_2$t-butyl$)_2$) , 7.17–7.51 (15H, m, aromatic H's); $^{13}$ CNMR: δ ($CDCl_3$) 27.9, 28.1, 41.1, 52.6, 52.8, 54.5, 55.0, 55.6, 56.1, 70.6, 80.8, 126.1, 127.7, 128.7, 146.3, 170.6, 170.9 (one quaternary carbon missing); MS FAB, [MH]+: 688.5; HRMS, [MH]+:688.4323 (calcd for $C_{41}H_{58}N_3O_6$: 688.4326).

The tritylated amine (120 mg, 0.2 mmol) and palladium black (150 mg) were stirred in 5.0 ml of methanol for 16 hours under an atmosphere of hydrogen gas. The palladium metal was removed by vacuum filtration and the solvent removed by rotary evaporation. Purification on silica gel using methanol/chloroform yielded 50 mg (64%) of a yellow oil:

$^1$H NMR: δ ($CDCl_3$) 1.42 (27H, s, $CO_2C(CH_3)_3$), 2.14 (2H, b, $NH_2$), 2.69 (4H, m, $H_2NCH_2CH_2$), 2.77 (4H, m, $RHNCH_2CH_2NR_2$), 3.27 (2H, s, $CH_2CH_2NRCH_2CO_2$t-butyl) , 3.42 (4H, s, $N(CH_2CO_2$t-butyl) $^{13}$CNMR δ ($CDCl_3$) 28.1, 39.9, 52.3, 52.8, 56.1, 57.1, 80.8, 80.9, 170.6, 171.1; MS FAB, [MH]+:m/z 446; HRMS, [MH]+: 446.3242 (calcd for $C_{22}H_{44}N_3O_6$: 446.3230).

To the sapphyrin mono-carboxylic acid structure 7a (37 mg, 50 μmol) in 20 ml of dry dichloromethane was added one drop of dimethylformamide followed by the cautious dropwise addition of 2.5 ml (5.0 mmol) of a 2.0M solution of oxalyl chloride in dichloromethane. The resulting solution was stirred at room temperature for 4 hours and the solvent was removed under vacuum. The resulting solids were redissolved in 20 ml of dry dichloromethane and 0.1 ml of dry pyridine and the amine (68 mg, 150 μmol) in 20 ml of dry dichloromethane was added dropwise over 1 hour. The reaction was allowed to stir overnight and the solvent was removed under vacuum. Purification on silica gel using methanol/dichloromethane yielded 32 mg of structure 8 as a blue solid (57%). The macrocycle can be further purified by recrystallization from dichloromethane/pentane:

$^1$H NMR: δ ($CDCl_3$) −5.03 (2H, m, NH), −4.57 (1H, s, NH), −4.38 (2H, s, NH), 1.32 (18H, s, $CO_2C(CH_3)_3$), 1.38 (9H, s, $CO_2C(CH_3)_3$), 3.29 (2H, s, $R_2NCH_2CO$), 3.42 (4H, s, $N(CH_2CO)_2$), 3.49 (4H, m, $NCH_2CH_2N$), 4.12 (6H, s, $CH_3$), 4.23 (6H, s, $CH_3$), 4.28 (3H, s, $CH_3$), 4.53 (4H, q, $CH_2CH_3$), 4.70 (4H, q, $CH_2CH_3$), 5.09 (2H, t, $CH_2CH_2CONH$), 7.58 (1H, b, CONH), 11.62 (s, 1H, meso-H), 11.70 (s, 2H, meso-H), 11.80 (s, 1H, meso-H); MS FAB, M+: 1057; HRMS, M+: 1056.6790 (calcd for $C_{62}H_{88}N_8O_7$: 1056.6776).

EXAMPLE 5

SYNTHESIS OF SAPPHYRIN DERIVATIVES 7a; 7b, FOR USE AS PRECURSORS

The synthesis of the precursor 3,8,17,22-Tetraethyl-12-(carboxyethyl)- 2,7,13,18,23-pentamethyl-sapphyrin, structure 7a, is a two part procedure requiring the preparation of the ester 3,8,17,22-tetraethyl-12-(methoxycarbonylethyl)-2, 7,13,18,23-pentamethylsapphyrin, structure 7b and subsequent hydrolysis to the sapphyrin acid of general structure 7a. Ester 7b was prepared in accord with the general optimized procedure for the production of substituted sapphyrins[4a], incorporated herein by reference. 4,4'-diethyl-5,5'-diformyl-3,3'-dimethyl-2,2'-bipyrrole (272 mg, 1.0 mmol) and 2,5-bis(5-carboxy-3-ethyl-4-methyl-pyrrol-2-yl-methyl)-3-methoxycarbonylethyl-4-methylpyrrole (523 mg, 1.0 mmol) were condensed to give this desired sapphyrin product in 75.4% yield (0.490 g).

$^1$H NMR (300 MHz, $CDCl_3$): δ=−4.78 (1H, s, NH), −4.76 (1H, s, NH), −4.32 (1H, s, NH), −4.13 (2H, s, NH), 2.35–2.43 (12H, m, $CH_2CH_3$), 3.85 (2H, t, $CH_2CH_2CO_2CH_3$), 3.99 (3H, s, $CH_3$), 4.29 (6H, s, $CH_3$), 4.38 (3H, s, $CH_3$), 4.44 (3H, s, $CH_3$), 4.67–4.74 (8H, m, $CH_2CH_3$), 5.22 (2H, t, $CH_2CH_2CO_2CH_3$), 11.82 (1H, s, meso-H), 11.85 (1H, s, meso-H), 11.88 (2H, s, meso-H). $^{13}$C NMR (75 MHz, $CDCl_3$): δ=12.7, 13.1, 15.9, 17.8, 17.9, 21.0, 23.0, 37.1, 52.1, 91.5, 92.0, 98.3, 98.4, 126.9, 127.0, 129.5, 129.6, 130.2, 132.7, 132.8, 134.7, 135.3, 135.5, 136.6, 136.7, 137.7, 139.1, 141.5, 141.7, 173.3. HRMS: Calcd. for $C_{41}H_{49}N_5O_2$: 643.3886. Found 643.3887.

The second part of the procedure involves the synthesis of sapphyrin acid 7a which was prepared as follows: a ca. 1:1 v.v. mixture of trifluoroacetic acid and conc. hydrochloric acid (10 ml for 100 mg of starting sapphyrin 7b) was used to hydrolyze the ester. The reaction was run at 50° C. for 2 days after which time the desired sapphyrin acid product was obtained as its bis HCl adduct. After drying in vacuo, this protonated product was purified by column chromatography on silica gel (methanol 5% in dichloromethane, eluent). The yield was ca. 95%.

$^1$H NMR (300 MHz, CDCl$_3$): δ=−5.84 (2H, bs, NH), −5.35 (3H, bs, NH), 2.20 (12H, t, CH$_3$CH$_2$), 3.23 (2H, t, CH$_2$CH$_2$CO$_2$H), 4.03 (3H, s, CH$_3$), 4.15 (6H, s, CH$_3$), 4.23 (3H, s, CH$_3$), 4.41 (3H, s, CH$_3$), 4.65 (4H, q, CH$_2$CH$_3$), 4.74 (4H, q, CH$_2$CH$_3$), 4.79 (2H, m, CH$_2$CH$_2$CO$_2$H), 11.42 (2H, s, meso-H), 11.55 (1H, s, meso-H), 11.58 (1H, s, meso-H). $^{13}$C NMR (75 MHz, CDCl$_3$): δ 12.7, 12.9, 14.3, 15.9, 17.7, 17.9, 20.6, 20.9, 22.8, 36.5, 36.7, 61.9, 91.6, 98.1, 120.7, 120.9, 125.4, 125.4, 127.3, 129.1, 129.2, 130.0, 132.7 132.8, 134.8, 134.9, 135.2, 135.4, 135.6, 135.7, 136.1, 136.8, 136.9 137.0, 137.7, 139.31, 141.4, 141.8, 141.8, 174.4. FAB MS, m/e (rel intensity): 631 (48, [MH$_2$]$^+$), 630 (100,[MH]$^+$), 629 (52, M$^+$); Calcd. for C$_{40}$H$_{47}$N$_5$O$_2$: Found 630.3798 ([MH]$^+$); for C$_{40}$H$_{48}$N$_5$O$_2$ [MH]$^+$: Calcd. 63808.

EXAMPLE 6

SYNTHESIS OF SAPPHYRIN MONONUCLEOBASE DERIVATIVES 3,8,17,22-Tetraethyl-12-[2-[1-[2-oxo-4-[(triphenylmethyl)amino]pyrimidyl]ethyl]aminocarbonylethyl]-2,7,13,18,23-pentamethylsapphyrin, structure 9.

Method A: The sapphyrin acid 7a, as prepared above (63 mg, 0.1 mmol), was dissolved in 10 ml of dry dichloromethane under argon. Oxalyl chloride (0.2 ml) was added followed by 0.03 ml of DMF. The reaction mixture was stirred at room temperature for 3 hours under argon and then evaporated to dryness in vacuo. The sapphyrin acid chloride so obtained was then redissolved in dry dichloromethane (20 ml) and added slowly under argon and at room temperature to a solution of 59.4 mg (0.15 mmol) of 1-(2-aminoethyl)-4-[(triphenylmethyl)-amino]-pyrimidin-2-one[19] containing 5 mg of 4-dimethylaminopyridine and 0.4 ml of dry pyridine in 20 ml of dry dichloromethane. After the addition was complete (ca. 1 hour), the reaction mixture was stirred overnight. The reaction mixture was then washed in succession with first dilute hydrochloric acid (3%, 20 ml), then water (20 ml) followed by saturated sodium bicarbonate (20 ml), and then finally water (20 ml) once again. The organic phase was then dried over sodium sulfate and the solvent removed in vacuo. The desired product 9 was isolated by column chromatography on silica gel using methanol, 2–5% in dichloromethane, as the eluent. The yield obtained this way was 91.0 mg (ca. 90%).

Method B. The sapphyrin acid 7a, described above (31.5 mg, 0.05 mmol), was dissolved in dry dichloromethane (20 ml). The resulting solution was then cooled to 0° C. and dicyclohexylcarbodiimide (41.27 mg, 0.2 mmol) and 1-hydroxybenzotriazole (5 mg) were added. The resulting solution was then stirred in an ice bath for 30 min. and the amino-functionalized cytosine, 1-(2-aminoethyl)-4-[(triphenylmethyl)amino]pyrimidin-2-one (29.7 mg, 0.075 mmol) was then added followed by 0.1 ml of dry pyridine. The reaction mixture was then stirred, first for 0.5 hours at 0° C. and then for 48 hours at room temperature. Acetic acid (0.2 ml) was then added and the solution stirred a further 1 hour at room temperature. Dicyclohexylurea was then filtered off and the reaction worked up as per method A. The yield of 9 obtained using this method was 42 mg (83.3 %).

$^1$H NMR (300 MHz, CDCl$_3$): δ=−5.43 (2H, bs, NH), −4.67 (2H, bs, NH), 2.21 (12H, t, CH$_2$CH$_3$), 2.73 (2H, t, CONHCH$_2$CH$_2$), 3.11 (2H, t, CH$_2$CH$_2$CONH), 4.07 (9H, s, CH$_3$), 4.18 (3H, s, CH$_3$), 4.30 (3H, s, CH$_3$), 4.50 (4H, m, CH$_2$CH$_3$), 4.60 (4H, m, CH$_2$CH$_3$), 4.67 (2H, m, CONHCH$_2$CH$_2$), 4.90 (2H, m, CH$_2$CH$_2$CONH), 6.20 (1H, d, C$^5$H ), 6.80, (1H, bs, NH), 7.06–7.26 (15H, m, Tr), 7.54 (1H, s, CONH), 7.73 (1H, d, C$^6$H), 11.55 (2H, s, meso-H), 11.56 (2H, s, meso-H). FAB MS, m/e (rel. intensity): 1008 (25, [MH]$^+$), 1007 (58, M$^+$), 1006 (22, [M-H]$^+$), 765 (22, [M-Tr]$^+$). HRMS: Calcd. for C$_{65}$H$_{69}$N$_9$O$_2$ (M$^+$): 1007.5574. Found 1008.5654 ([MH]$^+$); for C$_{65}$H$_{70}$N$_9$O$_2$ ([MH]$^+$): calcd. 1008.5652.

EXAMPLE 7

SYNTHESIS OF SAPPHYRIN MONONUCLEOBASE STRUCTURES 3,8,17,22-Tetraethyl-12-[2-[1-(4-amino-2-oxopyrimidinyl)-ethyl]-aminocarbonylethyl] -2,7,13,18,23-pentamethylsapphyrin, structure 10.

Compound 9 (50.4 mg, 0.05 mmol) was dissolved in trifluoroacetic acid (5 ml) and the solution was heated at reflux for 1 hour. After allowing the solution to cool, the solvent was removed in vacuo. The residue was then redissolved in dichloromethane, filtered, and taken to dryness on a rotary evaporator. The crude product so obtained was purified by recrystallization from a dichloromethane-hexane (1:3, v.v.) mixture, or by column chromatography on silica gel using dichloromethane-methanol 9:1 v.v. as the eluent. Such purifications afforded compound 10 as its bis trifluoroacetic salt in ca. 75% yield (28.5 mg). Prior to use in transport studies, this trifluoroacetate salt was dissolved in dichloromethane and washed with either a 1M solution of NaOH in H$_2$O or with a saturated aqueous solution of sodium bicarbonate.

$^1$H NMR (300 MHz, CDCl$_3$): δ=−6.66 (1H, s, NH), −6.57 (1H, s, NH), −6.50 (1H, s, NH ), −6.45 (1H, s, NH), −5.79 (1H, s, NH), 2.17 (12H, m, CH$_3$CH$_2$), 2.37 (2H, t, CONHCH$_2$CH$_2$), 3.08 (2H, t, CH$_2$CH$_2$CONH), 3.35 (2H, t, CONHCH$_2$CH$_2$), 4.11 (6H, s, CH$_3$), 4.20 (3H, s, CH$_3$), 4.23 (3H, s, CH$_3$), 4.25 (3H, s, CH$_3$), 4.54 (4H, q, CH$_2$CH$_3$), 4.68 (4H, q, CH$_2$CH$_3$), 5.12 (2H, t, CH$_2$CH$_2$CONH), 5.50 (1H, d, J=7.2, C$^5$H), 6.26 (2H, s, NH$_2$), 6.84 (1H, d, J=7.2, C$^6$H) 7.47 (1H, s, CONH), 11.52 (1H, s, meso-H), 11.65 (1H, s, meso-H), 11.69 (1H, s meso H), 11.70 (1H, s, meso-H).$^{13}$C NMR, (125 MHz, CDCl$_3$):- δ=12.52, 12.67, 12.86, 15.47, 15.83, 17.33, 17.51, 17.55, 17.57, 20.57, 20.68, 20.75, 22.55, 36.99, 37.74, 48.46, 91.50, 91.81, 91.87, 98.08, 98.22, 121.47, 126.37, 127.08, 127.82, 129.08, 129.92, 130.15, 130.20, 132.95, 132.98, 135.02, 135.25, 135.35, 135.61, 137.41, 138.51, 138.59, 140.49, 142.03, 142.10, 142.48, 147.08, 158.57, 173.65. FAB MS, m/e (rel. intensity): 768 (65, [MH$_2$]$^+$), 767 (78,[MH]$^+$), 766 (100, M$^+$), 766 (45, [M-H]$^+$). HRMS: Calcd. for C$_{46}$H$_{55}$N$_9$O$_2$ (M$^+$): 765.4478. Found 766.4535 ([MH]$^+$); for C$_{46}$H$_{56}$N$_9$O$_2$ ([MH]$^+$): calcd. 766.4556.

B. preparation of 3,8,17,22-tetraethyl-12-{2-[7-(2-benzamide-6-oxopurinyl)ethyl]-aminocarbonylethyl}-2,7,13,18,23-pentamethylsapphyrin, structure 11.

Sapphyrin monoacid 7a (63 mg, 0.1 mmol) was dissolved in dry tetrahydrofurane (30 ml) and cooled to 0° C., dicyclohexylcarbodiimide (103.2 mg, 0.5) was added with 10 mg of hydroxybenzotriazole and solution was kept at 0° C. for 30 minutes. 7-(2-Aminoethyl)-2-benzamidopurin-6-one was added with stirring. Reaction mixture was kept at 0° C.

for 1 hour, then allowed to room temperature, and stirred for 48 hours. Acetic acid (0.1 ml) was added and stirred 1 hour, dicyclohexylurea was filtered off, solvent evaporated in vacuo. Redissolved in dichloromethane with 5% methanol, washed with diluted hydrochloric acid (10 ml, 3%), saturated solution of sodium hydrogencarbonate (10 ml) and with water (10 ml). Organic phase was dried over sodium sulfate and evaporated to dryness. Product 11 was purified by column chromatography on silica gel with 2–5% methanol. The yield was 81 mg (89.0%).

FAB MS, m/e (rel. intensity): 911 (96,[MH]$^+$), 910 (86, [M]$^+$). HRMS: Calcd. for $C_{54}H_{60}N_{11}O_3$ 910.48739. Found 910.48806.

C. Preparation of 3,8,17,22-tetraethyl-12-{2-[7-(2-amino-6-oxopurinyl)ethyl]amino-carbonylethyl}-2,7,13,18,23-pentamethylsapphyrin, structure 12.

This was prepared by splitting of benzoyl protecting group from derivative 11 described above using $NH_3$ in methanol at room temperature for 24 hours in 85% yield.

FAB MS, m/e (rel. intensity): 806(96,[M]$^+$), 807 (68,[MH]$^+$). HRMS: Calcd. for $C_{47}H_{56}N_{11}O_2$ 806.46131. Found 806.46185.

D. 3,12,13,22-Tetraethyl-8-(methoxycarbonylethyl)-17-{2-[7(2-benzamido- 6-oxopurinyl)-ethyl]aminocarbonylethyl}-2,7,18,23-tetramethylsapphyrin, structure 13.

3,12,13,22-Tetraethyl-8-(carboxymethyl)-17-(methoxycarbonylethyl)-2,7,18,23-tetramethylsapphyrin 2c (23.5 mg, 0.033 mmol) was dissolved in dry dichloromethane (20 ml), solution was cooled by ice, dicyclohexylcarbodiimide (51.2 mg, 0.2 mmol) was added together with 5 mg of hydroxybenzotriazol, reaction mixture was kept at 0° C. for 30 minutes and then 7-(2-aminoethyl)-2-benzamidopurin-6-one (30 mg, 0.1 mmol) was added. The solution was kept cooled for 1 hour, then allowed to warm to room temperature and stirred for 30 hours. Acetic acid (0.1 ml) was added and stirred for 1 hour, dicyclohexylurea was filtered off, organic phase washed with water (10 ml), product was purified by crystallization from dichloromethane-hexane (1:1), final purification was made by column chromatography on silica gel with dichloromethane with 10% methanol and 0.3% of trifluoroacetic acid as a eluent. The yield of product 13 28 mg (79.5%).

$^1$H NMR spectrum (300 MHz, CDCl$_3$): δ=–5.50 (1H, s, NH), –5.31 (1H, s, NH), –5.04 (1H, s, NH), –4.97 (1H, s, NH), –4.95 (1H, s, NH), 2.05 (6H, t, $CH_2CH_3$), 2.20 (6H, t, $CH_2CH_3$), 2.91 (2H, t, $CH_2CH_2NH$), 3.46 (2H, t, $CH_2CH_2N$), 3.51 (3H, s, $CO_2CH_3$), 3.63 (2H, t, $CH_2CH_2CO$), 4.08 (6H, s, $CH_3$), 4.23 (6H, s, $CH_3$), 4.50 (2H, t, $CH_2CH_2NH$), 4.52 (4H, q, $CH_2CH_3$), 4.67 (4H, q, $CH_2CH_3$) 4.96 (2H, t, $CH_2CH_2CONH$), 7.40 (2H, m, BzH), 7.58 (1H, m, BzH), 7.65 (2H, m, BzH), 7.98 (1Hm br s, C$^8$H), 8.01 (1H, s, CONH), 11.62 (2H, s, meso-H), 11.63 (2H, s, meso-H).

$^{13}$C NMR (125 MHz, CDCl$_3$ with 20% CD$_3$OD): δ=12.68, 12.82, 16.52, 16.61, 17.76, 17.86, 18.47, 18.57, 20.56, 20.61, 20.65, 20.76, 22.76, 23.50, 29.58, 36.97, 51.98, 91.71, 96.25, 126.88, 127.41, 127.46, 128.27, 129.44, 129.59, 129.85, 129.96, 132.23, 133.96, 134.45, 138.12, 139.23, 143.45, 144.79, 145.10, 173.23, 173.35, 173.45.

FAB MS m/e (rel. intensity): 982 (95,[M-H]$^+$), 983 (87, [M]$^+$). HRMS: Calcd. for $C_{57}H_{64}N_{11}O_5$ 982.51087. Found 982.50919.

E. Preparation 3,12,13,22-Tetraethyl-8-(methoxycarbonylethyl)-17-{2-[17-(2-amino-6-oxopurinyl)ethyl]-aminocarbonylethyl}-2,7,18,23-tetramethylsapphyrin, structure 14.

This compound was prepared in 88% yield from the benzoyl derivative 13 previously described using a saturated solution of $NH_3$ in methanol at room temperature for 30 hours.

FAB MS, m/e (re. intensity): 879 (98,[M]$^+$), 880 (68, [MH]$^+$). HRMS: Calcd. for $C_{50}H_{61}N_{11}O_4$ 879.49291. Found 879.080.

F. Preparation of 3,12,13,22-Tetraethyl-8-(carboxymethyl)-17-{2-[7-(2-amino-6-oxopurinyl)ethyl]-aminocarbonylethyl}-2,7,18,23-tetramethylsapphyrin, structure 15.

This compound was prepared in 75% yield from the benzoyl derivative 13 by hydrolysis with KOH solution in methanol at room temperature for 48 hours. This is a very convenient building block for construction of sapphyrin conjugates with different nucleobases.

FAB MS, m/e (re intensity): 866 (68,[M]$^+$), 867 (56,[MH]$^+$, 865 (54, [M-H]$^+$). HRMS: Calcd. for $C_{49}H_{59}N_{11}O_4$ 865.47511. Found 865.47451.

EXAMPLE 8

SYNTHESIS OF SAPPHYRIN DINUCLEOBASE STRUCTURES

A. Preparation of 3,12,13,22-Tetraethyl-8-{2-[1-[2-oxo-4-[triphenylmethyl)-amino]pyrimidyl]ethyl]aminocarbonylethyl}-17-{2-[7-(2-amino-6-oxopurinyl)ethyl]-aminocarbonylethyl}-2,7,18,23-tetramethylsapphyrin, structure 16.

This compound was prepared in 69% yield from sapphyrin 15 as described above by condensation (carbodiimide method) with 1-(2-aminoethyl- 4-[(triphenylmethyl)amino]-pyrimidin-2-one.

FAB MS, m/e (rel. intensity): 1244 (78,[M]$^+$), 1245 (65,[MH]$^+$). HRMS: Calcd. for $C_{74}H_{81}N_{15}O_4$ 1243. 659547. Found 1243.65940.

B. Preparation of 3,12,13,22-Tetraethyl-8,17-bis{2-[7-(2-benzamido- 6-oxopurinyl)ethyl]-aminocarbonylethyl}-2,7, 18,23-tetramethylsapphyrin, structure 17.

Sapphyrin bis acid 2a (34.5 mg, 0.05 mmol) was converted to its corresponding bis acid chloride as previously described herein. A solution of this acid chloride in dry dichloromethane (20 ml) was then slowly added to a solution of 7-(2-aminoethyl)-2-benzamidopurin-6-one (60 mg, 0.2 mmol), which contained 0.3 ml of dry pyridine and 10 mg of 4-dimethylaminopyridine. The reaction mixture was stirred at room temperature for 36 hours. Dichloromethane-methanol (5:1) 20 ml was added and the resulting solution then washed first with diluted hydrochloric acid (10 ml, 3%), then with saturated solution of sodium hydrogencarbonate (10 ml) and then finally with water (10 ml). The organic phase was dried over sodium sulfate and evaporated to dryness. The product 17 was crystalized from methanol-dichloromethane (1:15). The yield was 55 mg (88.0%).

$^{13}$C NMR spectrum (125 MHz, CDCl$_3$ with 25% CD$_3$OD): δ=13.90, 15.63, 17.63, 18.41, 20.72, 20.83, 22.20, 22.81, 23.26, 33.99, 46.32, 46.36, 63.07, 92.00, 98.80, 110.10, 111.59, 123.02, 127.16, 127.73, 127.89, 128.34, 128.65, 128.95, 129.97, 131.09, 133.21, 133.41, 138.57, 138.91, 142.66, 144.00, 148.28, 151.44, 168.59, 168.89, 172.91, 173.30. FAB m/e (rel. intensity): 1249 (88, [M]$^+$), 1250 (56, [MH]$^+$), 1251 (45, [M+2H]$^+$). HRMS: Calcd. for $C_{70}H_{77}N_{17}O_6$ 1251. 62667. Found 1251.62427. [MH$_2$]$^+$.

C. Preparation of 3,12,13,22-tetraethyl-8,17-bis{2-[7-(2-amino-6-oxopurinyl)ethyl]-amino-carbonylethyl}-2,7,18, 23-tetramethylsapphyrin, structure 18.

This compound was prepared in 78% yield from the above-described bis benzoyl derivative 17 by stirring with $NH_3$ in methanol at room temperature for 30 hours.

FAM MS, m/e (rel. intensity): 1041 (95, [M]$^+$), 1040 (78, [M-H]$^+$), 1042 (56, [MH]$^+$). HRMS: Calcd. for $C_{56}H_{76}N_{17}O_4$ 1041.55787. Found 1041.55619.

D. 3,12,13,22-tetraethyl-8,17-bis[2-[1-[2-oxo-4-[(triphenyl-methyl)amino]pyrimidyl]-ethyl]aminocarbonylethyl]-2,7,13,18,23-tetramethylsapphyrin, structure 19.

3,12,13,22-Tetraethyl-8,17-bis(methoxycarbonylethyl)-2,7,18,23-tetramethyl-sapphyrin 2b and 3,12,13,22-tetraethyl-8,17-bis(carboxyethyl)-2,7,18,23-tetramethylsapphyrin 2a were prepared as described by Sessler et al. (1990; reference 4a), incorporated herein by reference. This latter diacid 2a (34.5 mg, 0.05 mmol) was then suspended in dry dichloromethane (20 ml), and, under argon, treated with oxalyl chloride (0.3 ml) and DMF (0.03 ml). The reaction mixture was stirred at room temperature for 3 hours and then taken to dryness in vacuo. The resulting sapphyrin bis acid chloride was redissolved in dry dichloromethane (15 ml) and added slowly to a solution of 1-(2-aminoethyl-4-[(triphenyl-methyl)amino]-pyrimidin-2-one (51.48 mg, 0.13 mmol) in dry dichloromethane (20 ml) containing 4-dimethylaminopyridine (5 mg) and dry pyridine (0.3 ml). The reaction mixture was stirred under argon at room temperature for 12 additional hours, then washed with first dilute hydrochloric acid (3%, 30 ml), then water followed by saturated aqueous sodium bicarbonate, and then, finally, with water once again. After drying over anhydrous sodium sulfate, the product was isolated by column chromatography on silica gel using dichloromethane-methanol (1→10%, gradient) as the eluent. The yield of compound 19 obtained in this manner was 65.0 mg (89.9%).

$^1$H NMR (300 MHz, CDCl$_3$): δ=−5.25 (2H, s, NH), −5.05 (2H, s, NH), 2.13 (12H, t, C$\underline{H}_3$CH$_2$), 2.93 (4H, m, CONHC$\underline{H}_2$CH$_2$), 3.23 (4H, m, CH$_2$C$\underline{H}_2$CONH), 3.83 (4H, t, CONHC$\underline{H}$CH$_2$), 4.00 (6H, s, CH$_3$), 4.15 (3H, s, CH$_3$), 4.25 (3H, s, CH$_3$), 4.57 (4H, q, C$\underline{H}_2$CH$_3$), 4.75 (4H, q, C$\underline{H}_2$CH$_3$), 4.99 (4H, m, CH$_2$CH$_2$CONH), 5.50 (2H, d, C$^5$H), 6.73 (2H, s, NH), 7.01–7.29 (30H, m, Tr), 7.28 (2H, d, C$^6$H), 7.67 (2H, s, CONH), 11.43 (4H, bs, meso-H). FAB MS m/e (rel intensity): 1446 (58, M$^{30}$), 1447 (38, [MH]$^+$). HRMS Calcd for C$_{92}$H$_{95}$N$_{13}$O$_4$: 1445.7645. Found 1445.7658.

E. 3,12,13,22-Tetraethyl-8,17-bis[2-[1-(4-amino-2-oxopyrimidinyl)-ethyl]-aminocarbonylethyl]-2,7,13,18,23-pentamethylsapphyrin, structure 20.

The bis(trityl) sapphyrin-cytosine derivative 19 (72.3 mg, 0.05 mmol) was dissolved in trifluoroacetic acid (5 ml) and heated to reflux for 0.5 hour. After cooling, the trifluoroacetic acid was removed by evaporation and the product purified (as its trifluoracetate salt) by column chromatography on silica gel using methanol (15% by volume) in dichloromethane as the eluent. Alternatively, this salt could be purified by recrystallization from dichloromethane-hexane-methanol (1:1:0.1 v.v.v.) to give 38.0 mg (79.0%) of deprotected product 20, (CF$^3$CO$_2$H)$_2$. Prior to use in transport studies, this trifluoroacetate salt was dissolved in dichloromethane and washed with either a 1M solution of NaOH in H$_2$O or with a saturated aqueous solution of sodium bicarbonate.

$^1$H NMR (300 MHz, CDCl$_3$): δ=−5.91 (1H, s, NH), −5.70 (2H, s, NH), −5.47 (2H, s, NH), 2.08 (6H, m, C$\underline{H}_3$CH$_2$), 2.13 (6H, m, C$\underline{H}_3$CH$_2$), 2.71 (4H, t, CONHC$\underline{H}_2$CH$_2$), 3.08 (4H, t, CH$_2$C$\underline{H}_2$CONH), 3.50 (4H, t, CONHC$\underline{H}$CH$_2$), 4.07 (3H, s, CH$_3$), 4.13 (3H, s, CH$_3$), 4.20 (3H, s, CH$_3$), 4.23 (3H, s, CH$_3$), 4.51 (4H, q, C$\underline{H}_2$CH$_3$), 4.68 (4H, q, C$\underline{H}_2$CH$_3$), 5.29 (4H, m, CH$_2$CH$_2$CONH), 5.69 (2H, d, J=7.20, C$^5$H), 6.35 (4H, bs, NH$_2$), 6.89 (2H, d, J=7.20, C$^6$H), 7.50 (2H, s, CONH), 11.52 ($^1$H, s, meso-H), 11.57 ($^1$H, s, meso-H), 11.61 (1H, s, meso-H), 11.63 (1H, s, meso-H). $^{13}$C NMR (125 2 MHz, CDCl$_3$ with 10% CD$_3$OD): δ=12.88, 12.90, 12.98, 16.03, 17.55, 17.63, 17.70, 18.23, 18.29, 18.37, 18.43, 20.23, 20.55, 20.75, 20.89, 20.91, 20.96, 22.58, 29.59, 35.58, 37.69, 37.84, 37.91, 48.80, 48.98, 49.15, 49.32, 49.48, 49.66, 49.83, 97.79, 97.91, 97.94, 97.97, 122.99, 128.27, 129.62, 129.74, 129.84, 129.86, 129.91, 129.95, 130.06, 130.10, 130.15, 130.24, 130.32, 135.38, 135.43, 138.93, 139.53, 143.23, 144.23, 144.59, 172.66. FAB MS m/e (rel intensity): 962 (45, M$^+$), 963 (38, [MH]$^+$). HRMS: Calcd for C$_{54}$H$_{67}$N$_{13}$O$_4$: 961.5439. Found 961.5448.

EXAMPLE 9

PREPARATION OF OLIGOMERIC SAPPHYRINS

PREPARATION OF SAPPHYRIN DIMERS

Sapphyrin monoacid 7a (126 mg, 0.2 mmol) was converted to acid chloride as previously described hereinabove. A solution of acid chloride in dry dichloromethane (20 ml) was slowly added to the solution of 0.1 mmol aromatic bis(amino) compound in dry dichloromethane (20 ml), which contained 5 mg 4-dimethylaminopyridine and 0.3 ml of dry pyridine. The reaction mixture was stirred 48 hours at room temperature, then washed with water, organic phase was dried with magnesium sulfate and evaporated. The product was isolated by column chromatography on silicagel in dichloromethane with 2–10% of methanol as a eluent. Reaction with 1,8-diaminonapthalene (0.1 mmol, 15.8 mg) gave 80 mg (57.89%) of product 21.

FAB MS m/e (rel. intensity) 1382 (67,[MH]$^+$), 1381 (56,[M]$^+$). HRMS Calcd. for C$_{90}$H$_{100}$N$_{12}$O$_2$: 1380.80916. Found 1380.8093.

Reaction with m-phenylenediamine (0.1 mmol, 10.8 mg) gave 69 mg (51.80%) of product FAB MS m/e (rel. intensity) 1333 (78,[MH]$^+$), 1332 (65,[M]$^+$). HRMS Calcd. for C$_{86}$H$_{98}$N$_{12}$O$_2$: 1330.79352. Found 1330.79349.

Reaction with aliphatic diaminocompounds was carried with DCC as a coupling reagent. Sapphyrin acid 7a (126 mg, 0.2 mmol) was dissolved in dry dichloromethane under argon and cooled by ice. Dicyclohexylcarbodiimide (0.5 g) was added with 5 mg of hydroxybenzotriazole. Reaction mixture was stirred at 0° C. for 30 minutes and then 1,3-diaminopropane (7.4 mg, 0.1 mmol) was added. Reaction mixture was stirred 30 minutes at 0° C. and 48 hours at room temperature. Acetic acid (0.2 ml) was added, stirred 1 hour, dicyclohexylurea was filtered off, product was isolated by column chromatography on silica gell with dichloromethane contains 5–10% of methanol. Yield of compound 23 is 96 mg (73.97%).

B. PREPARATION OF SAPPHYRIN TRIMERS

The inventors used the same coupling procedures as described above for the sapphyrin dimers. Thus sapphyrin monoacid 7a (189 mg, 0.3 mmol) was coupled (DCC method, 0.75 g) with tris(2-aminoethyl)amine (14.6 mg, 0.1 mmol) giving 160 mg (80.73%) of compound 24.

FAB MS m/e (rel. intensity) 1983 (36, [MH]$^+$), 1982 (32, [M]$^+$). HRMS Calcd. for C$_{126}$H$_{153}$N$_{19}$O$_3$: 1980.240296. Found 1980.240289.

EXAMPLE 10

PREPARATION OF SAPPHYRIN POLYMERS (CLASS I)

For the preparation of this class of polymers, sapphyrins with ethylene units could be used, as prepared by the elimination of acetoxy derivative, as well as sapphyrin bis acid, sapphyrin diamino and dihydroxyderivatives. Sapphyrins bearing covalently attached nucleobases could also be used for the polymerization reactions.

Radical polymerization may be catalyzed by dibenzoylperoxide, or bisazaisobutyronitril in inert solvent at temperature 120°–200° C.

Polycondensation reaction:

3,12,13,22-Tetraethyl-8,17-bis(carboxyethyl)-2,7,18,23-tetramethylsapphyrin 2a (1 mmol) and 1,1'-carbonyldiimidazole (1.1 mmol) were mixed in diphenylether for 1 hour, then 3,12,13,22-tetraethyl-8,17-diaminoethyl-2,7,18,23-tetramethylsapphyrin 25 (1 mmol) was added and reaction heated at 190°–250° C. for 2 hours. After cooling dichloromethane was added, polymeric sapphyrin structure 26A (where X=NH) was filtered off, washed with water (50 ml) and methanol (50 ml).

Polymeric sapphyrin was obtained also with using sulfolan, hexamethylphosphortriamide as a solvent. The reaction could be also carried out without solvent.

The same procedure was used for the sapphyrin dialcohol as a starting compound for the reaction with sapphyrin diacid structure 26B (where X=O).

To synthesize structure 27, it is contemplated that one would employ standard phosphoramidate chemistry.

EXAMPLE 11

SYNTHESIS OF POLYMER SUPPORTED SAPPHYRINS (CLASS II)

3,8,17,22-Tetraethyl-12-(carboxyethyl)-2,7,13,18,23-pentamethylsapphyrin structure, structure 28.

(0.63 g, 1 mmol) of 7a was converted to acid chloride as described hereinabove, oxalylchloride with DMF catalyst. A solution of this sapphyrin acid chloride in dry dichloromethane was then slowly added to a suspension of the benzhydrylamine hydrochloride polymer bound (BHA resin, α-aminodiphenylmethane hydrochloride polymer bound; polystyrene crosslinked with 2% divinylbenzene, α-aminobenzylated hydrochloride-0.7 mmol amine/g resin; 100–200 mesh), 1 g in 100 ml of dry dichloromethane, with 2 ml of dry pyridine. The reaction mixture was stirred at room temperature for 3 days. The polymeric material was filtered off, washed 5 times with dichloromethane (5×30 ml), 5 times with water (5×20 ml), 5 times with methanol (5×20 ml) and with dichloromethane (20 ml). The polymeric products were deep green in color as a result of the covalently attached sapphyrins, elemental analysis (a most important determination of bonded sapphyrin is an increase in nitrogen content as compared to the starting polymeric material) showed, that 85% of amino groups are attached to sapphyrin, structure 28.

The sapphyrin acid 7a (63 mg, 0.1 mmol), described hereinabove, was converted to its corresponding acid chloride. A solution of this acid chloride in dry dichloromethane was then added, under argon, to a suspension of aminomethyl-polystyrene (benzylamine polymer bound; copolymer of styrene and divinylbenzene, aminomethylated; 1.1 mmol amine/g resin) 500 mg in 50 ml of dry dichloromethane, with 0.5 ml of dry pyridine. The reaction mixture was stirred at room temperature for 7 days, and the resin was filtered off and washed as previously described. Elemental analysis was used to determine the quantity (loading level) of the attached sapphyrin. It was found that ca. 15% of the amino groups of the polymeric support were attached to sapphyrin, 29.

The same reaction starting with 200 mg of the above-specified aminomethyl-polystyrene gave 42% saturation in terms of amino groups bound to sapphyrin.

The same type of procedure was used for sapphyrin bis acid. For the connection of the sapphyrin mono acid with covalently bonded nucleobase, the amino functionalized polymer used as the solid support and either 1,1'-carbonyldiimidazole or 1-(3-dimethylaminopropyl)-3-ethylcarbodiimide were used as the acid activating agents as appropriate.

Sapphyrin bis amino derivative 25 (0.1 mmol) was dissolved in dry dimethylformamide and added to chloromethylated styrene-divinylbenzene resin (0.8 mmol Cl/g resin), 250 mg, together with 500 mg potassium carbonate. The reaction mixture was stirred and heated at 110° C. for 24 hours. After cooling to room temperature a solid material was filtered off, washed with water (250 ml), methanol (100 ml), and dichloromethane (100 ml). After drying, elemental analysis showed (as determined by a decrease in Cl content and an increase in N content) that 21% of the chloromethyl groups were transformed to sapphyrin-aminomethyl groups.

EXAMPLE 12

SELECTIVE NUCLEOTIDE TRANSPORT BY SAPPHYRIN-NUCLEOBASE CONJUGATES

As discussed above, the sapphyrin molecule itself, which remains monoprotonated in the ca. $3.5 \leq pH \leq 10$ regime,[5,18] is ineffective as a GMP carrier at pH 7, even in the presence of a large excess of C-Tips.[18] Therefore, sapphyrin systems in which nucleotide recognition units were appended directly onto the phosphate-chelating core, were synthesized, as described in the preceding examples.

Transport studies were carried out, using a standard[20] Aq I—$CH_2Cl_2$—$A_q$ II liquid membrane cell, using the sapphyrin cytosine conjugates represented by structures 10 and 20. Both 10 and 20 were found to be able to effect the selective through-membrane transport of GMP at, or near, neutral pH (Table 3).

TABLE 3

| Initial Nucleotide Transport Rates ($k_T$) for carriers 10 and 20. | | | | | | |
|---|---|---|---|---|---|---|
| Carrier[a] $k_G/k_C$ | (pH)[b] | Aq. I | Aq. II | $k_T$ CMP | $k_T$ GMP | $k_T$ AMP | $k_G/k_A$ |
| | | | | ($10^{-9}$ mol/cm$^2 \cdot$ h)[c] | | | |
| 10 | 6.15 | $H_2O$ | 0.12 | 12.0 | 1.57 | 7.6 | 100 |
| 10 | 7.05 | $H_2O$ | 0.0005 | 0.011 | 0.001 | 11 | 22 |
| 10 | 6.70 | 10 mM NaOH | 0.30 | 12.3 | 2.82 | 4.4 | 41 |
| 10 | 7.05 | 10 mM NaOH | 0.16 | 7.08 | 0.74 | 9.6 | 44 |
| 20 | 6.15 | $H_2O$ | 0.16 | 1.01 | 0.73 | 1.4 | 6.3 |
| 20 | 7.05 | 10 mM NaOH | 0.049 | 1.15 | 0.36 | 3.2 | 24 |
| none | 6.15 | $H_2O$ | $<10^{-4}$ | $<10^{-4}$ | | $<10^{-4}$ | dd |
| sap[e] | 7.0 | 10 mM NaOH | $<10^{-4}$ | $<10^{-4}$ | | 0.004 | |

TABLE 3-continued

Initial Nucleotide Transport Rates ($k_T$) for carriers 10 and 20.

| Carrier[a] $k_G/k_C$ | (pH)[b] Aq. I | Aq. II | $k_T$ CMP | $k_T$ GMP $(10^{-9}\ mol/cm^2 \cdot h)$[c] | $k_T$ AMP | $k_G/k_A$ |
|---|---|---|---|---|---|---|

[a] 0.1 mM in dichloromethane
[b] The source phase, Aq I, contained a 1:1:1 ratio of AMP, CMP, and GMP at a 10 mM conc. (in each). The initial pH was adjusted by the careful addition of $NaOH_{aq}$.
[c] Transport experiments were performed in a manner similar to those reported in refs. 14 and 5. Values reported are the average of three independent measurements; estimated error <5%.
[d] Not determined.
[e] Control experiment using 3,8,12,13,17,22-hexaethyl-2,7,18,23-tetramethylsapphyrin (0.1 mM) as the putative carrier.

As can be seen from Table 3, both 10 and 20 are able to effect the selective through-membrane transport of GMP at, or near, neutral pH. Using the standard[14] detection system, a quantitative analysis of uridine 5'-monophosphate (UMP) in Aq II could not be made. In qualitative control experiments, it was confirmed, however, that carrier 20 caused no apparent increase in the rate of through-membrane UMP transport at pH 6.7.

Interestingly, in all cases, receptor 20 displays a higher selectivity for GMP (by a factor of 8–100 relative to either AMP or CMP), than its congener 10. Further, better through-transport efficiency is always observed when the receiving phase (Aq II) is kept highly basic. Finally, a significant drop off in efficiency, for both 10 and 20, is observed as the initial pH of Aq I is increased from 6.15 to 7.05.

The above results are considered consistent with a model wherein complexation between the monoprotonated form of the receptor and the monobasic ($[ROPO_3H]^-$) form of GMP takes place at the Aq I—$CH_2Cl_2$ interface to produce a neutral, organic-soluble, supramolecular complex such as that depicted in FIG. 4C. This model is in accord with X-ray diffraction data in which the 2:1 complex formed between monobasic phenyl phosphate and diprotonated sapphyrin was analyzed in the solid state. One phenyl phosphate is bound on the "top" face of the macrocycle to each of three pyrroles, while the other phosphate is bound to two pyrroles on the "bottom" side.

This model, and the structure presented in FIG. 4C, provides a simple rationale for the experimental findings: First, decreased selectivity would be expected upon the introduction of "extra" cytosine chelating subunits, since this would result in an increase in number of possible hydrogen bonding interactions and an incumbent loss in required substrate specificity. Second, higher through-transport rates would be observed in those cases where the receiving phase is kept basic since sapphyrin deproteination and facilitated product release at the $CH_2Cl_2$—$A_q$ II interface would necessarily be favored. Finally, a decrease in through-transport rate is predicted since a lower concentration of the putative substrate, monobasic GMP (the $[ROPO_3H]^-$ form) in Aq I, would be expected as the second phosphate-centered ionization constant of GMP (pKa=ca. 6.7[21]) is first approached and then surpassed (charge neutralization as a requirement for efficient carrier mediated transport is known as Fick's First Law).

That some transport occurs even at pH 7.05 is thus considered a reflection of the fact that, under the conditions of the experiment, binding of monobasic GMP is enhanced relative to that of the dibasic ($[ROPO_3]^{2-}$) form and that this binding enhancement, in turn, serves to augment the effective concentration of this monanionic (and hence readily neutralizable) species in the organic membrane phase.

EXAMPLE 13

SAPPHYRIN-DNA INTERACTIONS

The present inventors have discovered that sapphyrin binds to double- and single-stranded DNA and RNA, and furthermore, that it does so in a novel and unexpected manner.

A. Sapphyrin Binds to DNA

The first evidence for sapphyrin DNA binding came from the observation that an excess of sapphyrin, which is green in solution, can rapidly and specifically precipitate green DNA fibers. The inventors propose that this binding and precipitation is due to the chelation of the polyanionic sugar-phosphate backbone of DNA. This leads to charge neutralization and through the resulting hydrophobic effects, the DNA falls out of solution. Such precipitation effects have not been reported for other DNA binding compounds which are known to either intercalate or groove bind with DNA.

Further evidence that sapphyrin binds to DNA was provided by CD spectroscopy, a technique that can detect chirality. Sapphyrin is an achiral macrocycle that shows no significant CD spectra by itself in solution. However, in the presence of DNA, a sapphyrin CD spectrum was induced. This is consistent with relatively rigid binding to DNA, a chiral macromolecule, which places sapphyrin in a chiral environment and yields the observed induced CD effect.

In addition, UV-Visible spectroscopy provides still further evidence that sapphyrin binds DNA. Upon addition of a large excess of DNA, changes in the visible absorption spectrum occur. The Soret-like transition that occurs at 410 nm is red-shifted by approximately 12 nm. This is taken as evidence that DNA is interacting directly with the sapphyrin macrocycle.

Finally, the inventors have determined that sapphyrin exhibits enhanced fluorescence in the presence of DNA. Sapphyrin alone shows only minimal fluorescence in aqueous buffered solution, but has been shown to either dimerize or aggregate in polar solvents resulting in a quenching of the sapphyrin fluorescence. The fluorescence enhancement effect discovered by the inventors is thus considered to be the result of binding to DNA which breaks up the dimers/aggregates and creates "monomeric" sapphyrins bound to DNA. Using this fluorescence enhancement as measurement of binding, the lower limit of the apparent binding constant has been estimated to be approximately $10^6\ M^{-1}$.

B. Sapphyrin-DNA Binding is not Intercalation or Groove Binding

Unwinding of double helical DNA has traditionally been accepted as a signature of DNA intercalators. Based on the apparent binding constant obtained using fluorescence spectroscopy, the inventors conducted topoisomerase-based unwinding studies using concentrations of sapphyrin where the sapphyrin macrocycle was significantly bound to the DNA. In such studies, no sapphyrin-mediated DNA unwinding was detected, leading to the conclusion that sapphyrin cannot be intercalating.

Preliminary results have indicated that nearly identical visible absorption changes can be observed when sapphyrin is titrated with either double-stranded DNA or single-stranded DNA. As single-stranded DNA contains no higher order structure, such as a major or minor groove, and the interaction appears to be spectroscopically identical between the two types of DNA, this data demonstrates that sapphyrin cannot be groove binding.

C. Sapphyrin Binds to the Phosphate Backbone of DNA

Recent X-ray crystallographic evidence has shown that the sapphyrin macrocycle can bind both monobasic phosphoric acid and monobasic phenyl phosphate. The inventors conducted a study aimed to link this solid state evidence to the interaction between sapphyrin and DNA which occurs in solution. They found that, in solution, spectroscopic similarities exist between sapphyrin in the presence of DNA and sapphyrin in the presence of diethyl phosphate. The latter is a simple phosphate that compares with the phosphates used in the X-ray crystallographic studies.

UV-visible spectral shifts comparable to those obtained with DNA can be observed when sapphyrin is titrated with diethyl phosphate. With diethyl phosphate, the Soret-like transition is red-shifted by approximately 9 nm. In addition, fluorescence enhancement in the presence of diethyl phosphate can be observed as in the case with DNA. The only structural similarity between this simple phosphate and the DNA is the phosphate anion and, when taken in conjunction with the X-ray crystallographic data, these spectroscopic techniques provide evidence for the novel mode of DNA binding proposed by the present inventors.

D. Porphyrins and Sapphyrins Interact Differently with DNA

To demonstrate that sapphyrins interact differently with DNA than their nearest relatives, porphyrins, the inventors synthesized a porphyrin 30 which was functionalized in a similar manner as the sapphyrin 1. Spectroscopically, these two molecules act very differently in the presence of DNA. Neither an induced CD effect nor any significant shifts in the visible absorption spectrum are observed with the functionalized porphyrin in the presence of DNA. In contrast to the fluorescence enhancement of sapphyrin, the porphyrin shows a decrease in fluorescence intensity in the presence of DNA.

The novel findings described in this example form the basis for even further uses of sapphyrin and sapphyrin derivatives as tools in the research or clinical laboratory. A particularly important application contemplated by the present inventors is to use sapphyrin, or derivatives or polymers thereof, in recovering DNA samples, for example, after electrophoresis. This may be applied as a general technique, or adapted for more specific DNA recognition and recovery by employing functionally derivatized sapphyrins, such as specific sapphyrin-nucleobase or -oligonucleobase conjugates. It is particularly contemplated that silica-supported sapphyrin may be employed in a "DNA catch" method to recover DNA samples from agarose gels.

EXAMPLE 14

SAPPHYRIN, DERIVATIVES AND CONJUGATES AS THERAPEUTIC AGENTS

The discoveries embodied by the present invention may be advantageously exploited in further scientific research, and importantly, in the development of new methods and compositions for treating various human diseases including cancer. Sapphyrins and their derivatives are envisioned to be of use in a wide variety of clinical embodiments, including the binding, delivery and cellular transport of nucleotide derivatives, such as antiviral agents. The sapphyrin-sugar derivatives have the added potential of more specific cellular targeting according to sugar recognition by specific receptors. Sapphyrins and modified sapphyrins also have potential for use directly as chemotherapeutics.

Sapphyrin may also be used as a delivery agent for the intracellular targeting of any drug that has a phosphate group. Of course, given the synthetic methodology disclosed herein, it is contemplated that the sapphyrin may be derivatized by the introduction of further groups to the periphery of the macrocycle, which groups would add the specificity and/or selectivity of the sapphyrin-drug interaction. Sapphyrin-drug interactions of this sort may be based upon either non-covalent interactions, or alternatively, may employ a covalent bond that is cleaved on exposure to the intracellular environment In particular embodiments, oligomers or polymers of sapphyrin or sapphyrin-nucleobase conjugates are envisioned to be of use in antisense technology. Such polymers will be of use both in the delivery and transport of oligonucleotides ("oligos"), and in enhancing their effectiveness once inside the target cell. The enhancing effect is based upon the newly discovered properties of sapphyrin in binding to the phosphate portions of nucleic acids. This property will increase the affinity of the antisense construct for its target, and reduce diffusion which generally limits the effectiveness of an antisense molecule. This dual transport and binding role of sapphyrin-oligonucleotide conjugates in anti-sense treatments is particularly advantageous in that no other method or combination of methods available have a DNA (or RNA) affinity component.

The newly-discovered interaction between sapphyrin and DNA, in which sapphyrin acts as a chelate for the phosphate backbone of DNA, is particularly important. The binding constant of unmodified sapphyrin for DNA has been determined to be on the order of $10^6$ $M^{-1}$, and evidence shows that the mode of DNA binding is not intercalation or groove binding. The inventors will extend these findings and create, using all the available experimental evidence, computer models of the sapphyrin-DNA interaction. These models will allow the design and engineering of covalently linked multimeric sapphyrin molecules with increased affinity and specificity.

These second generation multimeric sapphyrin-based constructs should have a DNA affinity high enough to interfere with biological processes such as transcription and translation. It is contemplated that this will ultimately lead to the development of sapphyrin-based therapeutic agents for use in treating a variety of human diseases, including cancer.

Sapphyrin molecules themselves are also contemplated for use directly as chemotherapeutic agents. Currently available chemotherapeutics generally have complex structures, or complicated modes of interaction with their targets, that preclude systematic improvement. The development of a novel class of DNA binding compounds, namely the sapphyrins of the present invention, therefore creates important new opportunities for the development and use of novel therapeutic agents.

Due to the unique mode of sapphyrin-DNA interaction, the sapphyrin molecule possesses an unrivaled ability to act as a general DNA binding platform. Binding can also be modified so as to adjust both target cell specificity and degree of interaction with the DNA. For sapphyrins, importantly, the basic site of interaction with the DNA involves the interior of the sapphyrin macrocycle, so that the exterior positions $R_1$–$R_{10}$ can be substantially modified without significantly disrupting the DNA binding interaction. These exterior positions can be used to systematically adjust features such as solubility, membrane permeability and cell selectivity. Furthermore, groups designed to modulate interaction with DNA can be attached to the exterior of the sapphyrins including alkylating functions (bromoacetamido groups, epoxides etc.) to provide covalent attachment to DNA or ene-diyne moieties to allow for double stranded DNA cleavage.

Another advantage of the sapphyrin system is that the DNA binding motif can be extended to multimeric structures, including the several described in the present application, in which multiple sapphyrins covalently linked together can bind to DNA simultaneously and thus strengthen the entire interaction. This feature will allow a modular approach in which the appropriate number (2–10) of sapphyrin molecules is attached in a single molecule, perhaps with different sapphyrin units containing sapphyrin derivatives with different groups attached that control such important properties such as solubility, target cell specificity and DNA modification ability.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. For example, other macrocyclic, positively-charged entities can be envisioned as binding to phosphate-containing species such as nucleotides, oligonucleotides and DNA by means of the same or similar oriented electrostatic interactions described herein. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

1. Sessler, J. L.; Burrel, A. K. *Topics in Current Chemistry*, 1991, 161, 177–273.

2. V. J. Bauer, D. L. J. Clive, D. Dolphin, J. B. Paine, III, F. L. Harris, M. M. King, J. Loder, S. -W. C. Wang, R. B. Woodward, *J. Am. Chem. Soc.* 105 1983 6429–6436.

3. M. J. Broadhurst, R. Grigg, A. W. Johnson, *J. Chem. Soc.*, Perkin Trans. 1 1972, 2111–2116.

4. (a) J. L. Sessler, M. J. Cyr, V. Lynch, E. McGhee, J. A. Ibers, *J. Am. Chem. Soc.* 112 1990 2810–2813. (b) M. Shionoya, H. Furuta, V. Lynch, A. Harriman, J. L. Sessler, *J. Am. Chem. Soc.* 114 1992, 5714–5722.

5. H. Furuta, M. J. Cyr, J. L. Sessler, J. L. *J. Am. Chem. Soc.* 113 1991 6677–6678.

6. J. L. Sessler, M. J. Cyr, A. K. Burrell, *Synlett.* 1991 127–133.

7. Robins, R. K. *Chemical and Engineering News* January 27, 1986, 28–40.

8. "*Approaches to Antiviral Agents*, Harden M R. Ed; VCH Publishers: Deerfield Beach, Fla., 1985.

9. Holy, A. in *Approaches to Antiviral Agents*, Harden, M. R. (Ed.), VCH Publishers, Deerfield Beach, Fla., 1985, pp. 101–134.

10. (a) Tabushi, I.; Kobuke, Y.; Imuta, J. *J. Am. Chem. Soc.* 1981, 103, 6152–6157. (b) Kimura, E. *Top. Curt. Chem.* 1985, 128, 113–141. (c) Schmidtchen, F. P. *Top. Curt. Chem.* 1986, 132, 101–133. (d) Lehn, J. -M. *Angew. Chem., Int. Ed. Engl.* 1988, 27, 89–112. (e) Marecek, J. F.; Fischer, P. A.; Burrows, C. *J. Tetrahedron Lett.* 1988, 29, 6231–6234. (f) Schmidtchen, F. P. *Tetrahedron Lett.* 1989, 30, 4493–4496. (g) Mertes, M. P.; Mertes, K. B. *Acc. Chem. Res.* 1990, 23, 413–418. (h) Hosseini, W.; Blacker, A. J.; Lehn, J. -M. *J. Am. Chem. Soc.* 1990, 112, 3896–3904. (i) Kimura, E.; Kuramoto, Y.; Koike, T.; Fujioka, H.; Kodama, M. *J. Org. Chem.* 1990, 55, 42–46. (j) Aoyama, Y.; Nonaka, S.; Motomura, T.; Toi, H.; Ogoshi, H. *Chem. Lett.* 1991, 1241–1244. (k) Claude, S.; Lehn, J. -M; Schmidt, F.; Vigneron, J. -P. *J. Chem. Soc., Chem. Commun.* 1991, 1182–1185. (l) Deslongchamps, G.; Galán, A.; de Mendoza, J.; Rebek, J., Jr. *Angew. Chem., Int. Ed. Engl.* 1992, 31, 61–63. (m) Dixon, R. P.; Geib, S. J.; Hamilton, A. D. *J. Am. Chem. Soc.* 1992, 114, 365–366. (n) Ariga, K.; Anslyn, E. V. *J. Org. Chem.* 1992, 57, 417–419. (o) Muehldorf, A. V.; Van Engen, D.; Warner, J. C.; Hamilton, A. D. *J. Am Chem. Soc.* 1988, 110, 6561–6562. (p) Adrian, J. C.; Wilcox, C. S. *J. Am. Chem. Soc.* 1989, 111, 8055–8057. (q) Benzing, T.; Tjivikua, T.; Wolfe, J.; Rebek, J., Jr. *Science*, 1988, 242, 266–268. (r) Seel, C.; Vögtle, F. *Angew. Chem. Int. Ed. Engl.* 1991, 30, 442–444. (s) Goodman, M. S.; Rose, S. D. *J. Am. Chem. Soc.* 1991, 113, 9380–9382. (t) Lindsey, J. S.; Kearney, P. C.; Duff, R. J.; Tjivikua, T.; Rebek, J., Jr. *J. Am. Chem. Soc.* 1988, 110, 6575–6577. (u) Ogoshi, H.; Hatekeyama, H.; Kotani, J.; Kawashima, A.; Kuroda, Y. *J. Am. Chem. Soc.* 1991, 113, 8181–8183.

11. A. K. Burrell, J. L. Sessler, M. J. Cyr, E. McGhee, J. A. Ibers, *Angew. Chem.* 103 1991 83–85; *Angew. Chem. Int. Ed. Engl.* 30 (1991) 91–93.

12. J. L. Sessler, D. Ford, M. J. Cyr, H. Furuta, *J. Chem. Soc., Chem. Commun.* 1991, 1733–1735.

13. *The Biochemistry of the Nucleic Acids*, 10th ed., Adams, R. L. P.; Knowler, J. T.; Leader, D. P. (Eds.), Chapman and Hall, New York, 1986.

14. Furuta, H.; Furuta, K.; Sessler, J. L. *J. Am. Chem. Soc.* 1991, 113, 4706–4707.

15. Cell Surface Carbohydrate Chemistry, Ed. R. E. Harmon, Academic Press, NY, 1978, p. 225, G. A. Jarnieson: Surface Glycoproprteins of Normal and Abnormal Platelets p. 311: B. Paul, W. Korytnyk: Cell Surface as a target for chemotherapy. Potential inhibitors of Biosynthesis of Protein-Carbohydrate Linkage in Glycoproteins.

16. R. J. Bernacki, M. Sharma, N. K, Poter, Y. Rustum, B. Paul, W, Korytnyk: *J. Supramol. Structure* 7, 235–250 1977.

17. Sessler, J. L.; Morishima, T.; Lynch, V. *Angew. Chem., Int. Ed. Eng.* 1991, 30, 977–980.

18. Furuta, H.; Morishima, T.; Král, V.; Sessler, J. L., *Supramolec. Chem.*, in press.

19. Sessler, J. L.; Magda, D.; Furuta, H. *J. Org. Chem.* 1992, 57, 818–826.

20. Tsukube, H. in *Liquid Membranes: Chemical Applications*, Araki, T.; Tsukube, H. (Eds.), CRC Press, Boca Raton, 1990, pp. 27–50.

21. Phillips, R.; Eisenberg, P.; George, P.; Rutman, R. J. *J. Biol. Chem.* 1965, 240, 4393–4397.

What is claimed is:

1. A sapphyrin derivative having the structure:

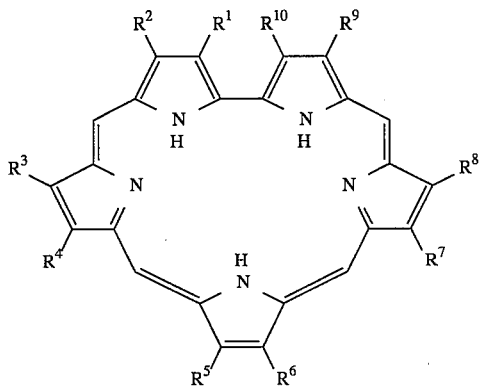

each of $R^1$–$R^{10}$ being H, alkyl, alkene, alkyne, halide, alkyl halide, hydroxyalkyl, glycol, polyglycol, thiol, alkyl thiol, aminoalkyl, carboxyalkyl, alkoxyalkyl, aryloxyalkyl, alkyloxycarbonyl, aryloxycarbonyl, aldehyde, ether, ketone, carboxylic acid, phosphate, phosphonate, sulfate, phosphate substituted alkyl, phosphonate substituted alkyl, or sulfate substituted alkyl, such that the total number of carbon atoms in each substituent R is less than or equal to 10; and wherein at least one of $R^1$–$R^{10}$ are of the formula $(CH_2)_n$—A—$(CH_2)_m$—B, wherein A is $CH_2$, O, S, NH or $NR^{11}$, wherein $R^{11}$ is alkyl, alkene, alkyne, halide, alkyl halide, hydroxyalkyl, glycol, polyglycol, thiol, alkyl thiol, substituted alkyl, phosphate, phosphonate, sulfate, phosphate substituted alkyl, phosphonate substituted alkyl, sulfate substituted alkyl, COO, CONH, CSNH, $CONR^{11}$; and B is a nucleobase, modified nucleobase, oligonucleotide or polynucleotide; and n and m are integers of less than or equal to 10 or zero.

2. The sapphyrin derivative of claim 1, wherein n is an integer of less than or equal to 6 or zero, and m is an integer of less than or equal to 4 or zero.

3. The sapphyrin-nucleobase conjugate of claim 1, wherein B is an adenine, cytosine, guanine, thymidine, uridine or inosine base, nucleotide or nucleoside.

4. The sapphyrin-nucleobase conjugate of claim 1, wherein B is a nucleotide or nucleoside derivative or analogue.

5. The sapphyrin-nucleobase conjugate of claim 4, wherein the analogue is an antimetabolite.

6. The sapphyrin-nucleobase conjugate of claim 5, wherein the antimetabolite is one selected from Table 2.

7. The sapphyrin-nucleobase conjugate of claim 4, wherein the derivative is a protected nucleobase with protecting group $R^{12}$ on amino group of nucleobases, where $R^{12}$ is 9-fluorenylmethyl carbonyl, benzyloxycarbonyl, 4-methoxyphenacyloxycarbonyl, t-butyl oxycarbonyl, 1-adamantyloxycarbonyl, benzoyl, N-triphenylmethyl or N-di-(4-methoxyphenyl)phenylmethyl; and n is an integer from 1 to 6 and m is an integer from 1 to 4.

8. The sapphyrin-nucleobase conjugate of claim 1, wherein only one R group is substituted with the nucleobase-containing substituent.

9. The sapphyrin-nucleobase conjugate of claim 8, wherein the nucleobase-containing substituent is composed of 1 to 10 nucleobase units.

10. The sapphyrin-nucleobase conjugate of claim 9 wherein the nucleobase-containing substituent has two nucleobase units.

11. The sapphyrin-nucleobase conjugate of claim 9, wherein the nucleobase-containing substituent has one nucleobase unit.

12. The sapphyrin-nucleobase conjugate of claim 1, wherein two R groups are substituted with the nucleobase-containing substituent.

13. The sapphyrin-nucleobase conjugate of claim 12, wherein the nucleobase containing substituents are each composed of from 1 to 10 nucleobase units.

14. The sapphyrin-nucleobase conjugate of claim 1, further defined as having structure 9 of FIG. 4.

15. The sapphyrin-nucleobase conjugate of claim 1 further defined as having structure 9 of FIG. 4A-2.

16. The sapphyrin-nucleobase conjugate of claim 1, further defined as having structure 10 of FIG. 4A-3.

17. The sapphyrin-nucleobase conjugate of claim 1, further defined as having structure 11 of FIG. 4A-4.

18. The sapphyrin-nucleobase conjugate of claim 1, further defined as having structure 12 of FIG. 4A-5.

19. The sapphyrin-nucleobase conjugate of claim 1, further defined as having structure 13 of FIG. 4A-6.

20. The sapphyrin-nucleobase conjugate of claim 1, further defined as having structure 14 of FIG. 4A-6.

21. The sapphyrin-nucleobase conjugate of claim 1, further defined as having structure 15 of FIG. 4A-7

22. The sapphyrin-nucleobase conjugate of claim 1, further defined as having structure 16 of FIG. 4B-2.

23. The sapphyrin-nucleobase conjugate of claim 1, further defined as having structure 17 of FIG. 4B-3.

24. The sapphyrin-nucleobase conjugate of claim 1, further defined as having structure 18 of FIG. 4B-3.

25. The sapphyrin-nucleobase conjugate of claim 1, further defined as having structure 19 of FIG. 4B-4.

26. The sapphyrin-nucleobase conjugate of claim 1, further defined as having structure 20 of FIG. 4B-5.

\* \* \* \* \*

UNITED STATES PATENT AND TRADEMARK OFFICE
CERTIFICATE OF CORRECTION

PATENT NO. : 5,457,195

DATED : October 10, 1995

INVENTOR(S) : Jonathan L. Sessler; Brent L. Iverson; Vladimir Král; Kevin Shreder; and Hiroyuki Furuta It is certified that error appears in the above-identified patent and that said Letters Patent is hereby corrected as shown below:

In claim 1, column 41, line 36, please delete "modified nucleobase, oligonucleotide or polynucleotide".

Signed and Sealed this

Second Day of July, 1996

Attest:

BRUCE LEHMAN

Attesting Officer

Commissioner of Patents and Trademarks

Disclaimer

5,457,195—Jonathan L. Sessler; Brent L. Iverson; Vladimir Kral; Kevin Shreder, all of Austin, Tex.; Hiroyuki Furuta, Mitsuyoshi, Japan. SAPPHYRIN DERIVATIVES AND CONJUGATES. Patent dated Oct. 10, 1995. Disclaimer filed Feb. 20, 1997, by the assignee, Board of Regents, The University Of Texas System.

Hereby enters this disclaimer to claim 14 of said patent.
*(Official Gazette,* June 17, 1997)

UNITED STATES PATENT AND TRADEMARK OFFICE
CERTIFICATE OF CORRECTION

PATENT NO : 5,457,195
DATED : October 10, 1995
INVENTOR(S) : Sessler, *et al.*

It is certified that error appears in the above-identified patent and that said Letters Patent is hereby corrected as shown below:

At column 1, lines 4-5, please delete the first sentence that reads: "The government owns rights in the present invention pursuant to NIH grant AI 28845" and replace it with the following paragraph:

-- The government may own certain rights in the present invention pursuant to one or more of the following: National Institutes of Health Grants CA68682 and AI28845; and National Science Foundation Grants CHE8552768 and CHE9122161.--

Signed and Sealed this

Sixth Day of June, 2000

Attest:

Q. TODD DICKINSON

Attesting Officer

*Director of Patents and Trademarks*